US012110516B2

(12) United States Patent
Nirantar et al.

(10) Patent No.: US 12,110,516 B2
(45) Date of Patent: *Oct. 8, 2024

(54) THERMOSTABLE TERMINAL DEOXYNUCLEOTIDYL TRANSFERASE

(71) Applicants: Illumina, Inc., San Diego, CA (US); Illumina Singapore Pte. Ltd., Singapore (SG); National University of Singapore, Singapore (SG)

(72) Inventors: Saurabh Rajendra Nirantar, Singapore (SG); Jasmine Puay Suan Chua, Singapore (SG); Sergio Peisajovich, San Diego, CA (US); Wen Shan Yew, Singapore (SG); Maybelle Darlene Kho Go, Singapore (SG)

(73) Assignees: Illumina, Inc., San Diego, CA (US); Illumina Singapore Pte. Ltd., Singapore (SG); National University of Singapore, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/317,721

(22) Filed: May 11, 2021

(65) Prior Publication Data

US 2021/0355460 A1    Nov. 18, 2021

Related U.S. Application Data

(60) Provisional application No. 63/023,734, filed on May 12, 2020.

(51) Int. Cl.
C12N 9/12    (2006.01)

(52) U.S. Cl.
CPC .... *C12N 9/1264* (2013.01); *C12Y 207/07031* (2013.01)

(58) Field of Classification Search
None
See application file for complete search history.

(56) References Cited

U.S. PATENT DOCUMENTS

| | | |
|---|---|---|
| 10,059,929 B2 | 8/2018 | Efcavitch et al. |
| 10,583,415 B2 | 3/2020 | Banyai et al. |
| 2009/0280535 A1 | 11/2009 | Wang |
| 2018/0023108 A1 | 1/2018 | Chen et al. |
| 2019/0390178 A1 | 12/2019 | Champion et al. |
| 2021/0009969 A1 | 1/2021 | Tubbs et al. |
| 2021/0355518 A1 | 11/2021 | Nirantar et al. |
| 2022/0025421 A1 | 1/2022 | Ee et al. |

FOREIGN PATENT DOCUMENTS

| | | |
|---|---|---|
| GB | 2553274 | 3/2018 |
| WO | WO2004018497 | 3/2004 |
| WO | WO2014162307 | 10/2014 |
| WO | WO2016064880 | 4/2016 |
| WO | WO2016128731 | 8/2016 |
| WO | WO2017216472 | 12/2017 |
| WO | WO2018217689 | 11/2018 |
| WO | WO2019094524 | 5/2019 |
| WO | WO2020081985 | 4/2020 |
| WO | WO2020161480 | 8/2020 |
| WO | WO2021116270 | 6/2021 |
| WO | WO2021231477 | 11/2021 |
| WO | WO2021231483 | 11/2021 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Guo et al. (H. Guo et al., "Protein Tolerance to Random Amino Acid Change", PNAS 101(25): 9205-9210, Jun. 2004).*
Baranello et al., "DNA Break Mapping Reveals Topoisomerase II Activity Genome-Wide," International Journal of Molecular Sciences 2014, 15, 13111-13122.
Barthel et al., "Enhancing Terminal Deoxynucleotidyl Transferase Activity on Substrates with 30 Terminal Structures for Enzymatic De Novo DNA Synthesis," Genes 2020, 11(102), in 9 pages.
Beaucage & Caruthers, "Deoxynucleoside Phosphoramidites—A New Class of Key Intermediates for Deoxypolynucleotide Synthesis," Tetrahedron Letters 1981, 22(20), 1859-1862.
Bentley et al., "Accurate whole human genome sequencing using reversible terminator chemistry," Nature 2008, 456, in 7 pages.
Bertocci et al., "Nonoverlapping Functions of DNA Polymerases Mu, Lambda, and Terminal Deoxynucleotidyltransferase during Immunoglobulin V(D)J Recombination In Vivo," Immunity 2006, 25, 31-41.
Bollum et al., "Thermal Conversion of Nonpriming Deoxyribonucleic Acid to Primer," The Journal of Biological Chemistry 1959, 234(10), 2733-2734.
Bollum et al., "Calf Thymus Polymerase," The Journal of Biological Chemistry 1960, 235(8), 2399- 2403.
Bollum, "Terminal Deoxynucleotidyl Transferase," The Enzymes 1974, 10, 145-171.
Bornholt et al., "A DNA-Based Archival Storage System," ASPLOS 2016, 637-649.
Boule et al., "Comparison of the Two Murine Deoxynucleotidyltransferase Terminal Isoforms," The Journal of Biological Chemistry 2000, 275(37), 28984-28988.

(Continued)

*Primary Examiner* — Richard G Hutson
(74) *Attorney, Agent, or Firm* — Sheppard, Mullin, Richter & Hampton LLP

(57) ABSTRACT

Disclosed herein include recombinant terminal deoxynucleotidyl transferases (TdTs). In some embodiments, the recombinant TdT comprises an amino acid sequence that is at least 80% identical to a bovine TdT, wherein the recombinant TdT comprises one or more amino acid substitution mutations at one or more positions functionally equivalent to Glu191, Lys193, Glu194, Asp242, Lys287, Phe296, Met299, Thr342, and His421 in the bovine TdT.

23 Claims, 18 Drawing Sheets

Specification includes a Sequence Listing.

(56) References Cited

OTHER PUBLICATIONS

Bowers et al., "Virtual Terminator nucleotides for next generation DNA sequencing," Nat Methods 2009, 6(8), 593-595.
Caruthers, "The Chemical Synthesis of DNA/RNA: Our Gift to Science," The Journal of Biological Chemistry 2013, 288(2), 1420-1427.
Chen et al., "The History and Advances of Reversible Terminators Used in New Generations of Sequencing Technology," Genomics Proteomics Bioinformatics 2013, 11, 34-40.
Chua et al., "Evolving a Thermostable Terminal Deoxynucleotidyl Transferase," ACS Synthetic Biology 2020, 9, 1725-1735.
Church et al., "Next-Generation Digital Information Storage in DNA," Sciencexpress 2012, in 2 pages.
Delarue et al., "Crystal structures of a template-independent DNA polymerase: murine terminal deoxynucleotidyltransferase," The EMBO Journal 2002, 21(3), 427-439.
Durowoju et al., "Differential Scanning Calorimetry—A Method for Assessing the Thermal Stability and Conformation of Protein Antigen," Journal of Visualized Experiments 2017, 121, in 8 pages.
Dymond et al., "Synthetic chromosome arms function in yeast and generate phenotypic diversity by design," Nature 2013, 477(7365), 471-476.
Extance, "Digital DNA; Could the Molecule known for storing genetic information also store the world's data?" Nature 2016, 537, 22-24.
Gavrieli et al., "Identification of Programmed Cell Death In Situ via Specific Labeling of Nuclear DNA Fragmentation," The Journal of Cell Biology 1992, 119(3), 493-501.
Gibson et al., "Creation of a Bacterial Cell Controlled by a Chemically Synthesized Genome," Science 2010, 329(5987), 52-56.
Goldman et al., "Toward practical high-capacity low-maintenance storage of digital information in synthesized DNA," Nature 2013, 494(7435), 77-80.
Gorczyca et al., "Detection of DNA Strand Breaks in Individual Apoptic Cells by in Situ Terminal Deoxynucleotidyl Transferase and Nick Translation Assays," Cancer Research 1993, 53, 1945-1951.
Hottin & Marx, "Structural Insights into the Processing of Nucleobase-Modified Nucleotides by DNA Polymerases," American Chemical Society 2016, 49, 418-427.
Hu et al., "A TdT-mediated cascade signal amplification strategy based on dendritic DNA matrix for label-free multifunctional electrochemical biosensing," Biosensors and Bioelectronics 2015, 63, 331-338.
Hutchinson et al., "Design and synthesis of a minimal bacterial genome," Science 2016, 351(6280), in 12 pages.
Hutter et al., "Labeled Nucleoside Triphosphates With Reversibly Terminating Aminoalkoxyl Groups," Nucleosides, Nucleotides and Nucleic Acids 2010, 29, 879-895.
Huynh and Partch, "Analysis of protein stability and ligand interactions by thermal shift assay," Current Protocols in Protein Science 2015, 79, in 19 pages.
International Search Report and Written Opinion dated Aug. 26, 2021 in PCT Patent Application No. PCT/US2021/031852.
International Search Report and Written Opinion dated Nov. 11, 2021 in PCT Patent Application No. PCT/US2021/031843.
Jarchow-Choy et al., "Fluorescent xDNA nucleotides as efficient substrates for a template-independent polymerase," Nucleic Acids Research 2011, 39(4), 1586-1894.
Jensen & Davis, "Template-Independent Enzymatic Oligonucleotide Synthesis (TiEOS): Its History, Prospects, and Challenges," Biochemistry 2018, in 12 pages.
Ju et al., "Four-color DNA sequencing by synthesis using cleavable fluorescent nucleotide reversible terminators," PNAS 2006, 103(52), 19635-19640.
Juárez et al., "A specific loop in human DNA polymerase mu allows switching between creative and DNA-instructed synthesis," Nucleic Acids Research 2006, 34(16), 4572-4582.

Kato et al., "Deoxynucleotide-polmerizing Enzymes of Calf Thymus Gland," The Journal of Biological Chemisty 1987, 242(11), 2780-2789.
Kelley et al., "The Phyre2 web portal for protein modelling, prediction and analysis," Nature Protocols 2015, 10(6), 845-858.
Lazinski & Camilli, "Homopolymer tail-mediated ligation PCR: a streamlined and highly efficient method for DNA cloning and library construction," BioTechniques 2013, 54(1), 25-34.
Lee et al., "Terminator-free template-independent enzymatic DNA synthesis for digital information storage," Nature Communications 2019, 10(2283), in 12 pages.
Lee et al., "Enzymatic DNA synthesis for digital information storage," bioRxiv 2018, in 31 pages.
Leproust et al., "Synthesis of high-quality libraries of long (150mer) oligonucleotides by a novel depurination controlled process," Nucleic Acids Research 2010, 38(8), 2522-2540.
Liang et al., "Synthetic biology: putting synthesis into biology," WIREs Syst Biol Med 2011, 3, 7-20.
Loh'h et al., "Structural evidence for an in trans base selection mechanism involving Loop1 in polymerase u at an NHEJ double-strand break junction," The Journal of Biological Chemistry 2019, 294(27), 10579-10595.
Loc'h , "Terminal deoxynucleotidyltransferase: the story of an untemplated DNA polymerase capable of DNA bridging and templated synthesis across strands," Current Opinion in Structural Biology 2018, 53, 22-31.
Moon et al., "The X Family Portrait: Structural Insights into Biological Functions of X Family Polymerases," DNA Repair 2007, 6(12), 1709-1725.
Motea & Berdis, "Terminal Deoxynucleotidyl Transferase: The Story of a Misguided DNA Polymerase," Biochimica et Biophysica Acta 2010, 1804(5), 1151-1166.
Musil et al., "FireProt: web server for automated design of thermostable proteins," Nucleic Acids Research 2017, 45, W393-W399.
Ostrov et al., "Design, synthesis, and testing toward a 57-codon genome," Science 2016, 353(6301), 819-822.
Palluk et al., "De novo DNA synthesis using polymerase-nucleotide conjugates," Nature Biotechnology 2018, 1-6.
Peng et al., "TELP, a sensitive and versatile library construction method for next-generation sequencing," Nucleic Acids Research 2014, 43(6), e35, in 13 pages.
Pina-Anguilar et al., "Revival of Extinct Species Using Nuclear Transfer: Hope for the Mammoth, True for the Pyrenean Ibex, But Is It Time for "Conservation Cloning"?," Cloning and Stem Cells 2009, 11(3), in 6 pages.
Richardson et al., "Design of a synthetic yeast genome," Science 2017, 355, 1040-1044.
Romain et al., "Conferring a template-dependent polymerase activity to terminal deoxynucleotidyltransferase by mutations in the Loop1 region," Nucleic Acids Research 2009, 37(14), 4642-4656.
Rosa et al., "Meltdown: A Tool to Help in the Interpretation of Thermal Melt Curves Acquired by Differential Scanning Fluorimetry," Journal of Biomolecular Screening 2015, 20(7), 898-905.
Ruparel et al., "Design and synthesis of a 3'-O-allyl photocleavable fluorescent nucleotide as a reversible terminator for DNA sequencing by synthesis," PNAS 2005, 102(17), 5932-5937.
Sarac & Hollenstein, "Terminal Deoxynucleotidyl Transferase in the Synthesis and Modification of Nucleic Acids," ChemBioChem 2019, 20, 860-871.
Sharma et al., "Terminal deoxynucleotidyl transferase dUTP nick end labeling (TUNEL) assay using bench top flow cytometer for evaluation of sperm DNA fragmentation in fertility laboratories: protocol, reference values, and quality control," The Journal of Assisted Reproduction and Genetics 2016, 33, 291-300.
Slavičková et al., "Additions of Thiols to 7-Vinyl-7-deazaadenine Nucleosides and Nucleotides. Synthesis of Hydrophobic Derivatives of 2'-Deoxyadenosine, dATP and DNA, " The Journal of Organic Chemistry 2016, 81, 11115-11125.
Tauraitė et al., "Modified Nucleotides as Substrates of Terminal Deoxynucleotidyl Transferase," Molecules 2017, 22(672), in 16 pages.

(56) References Cited

OTHER PUBLICATIONS

Tjong et al., "Amplified On-Chip Fluorescence Detection of DNA Hybridization by Surface-Initiated Enzymatic Polymerization," Analytical Chemistry 2011, 5153-5159.
Tjong et al., Direct Fluorescence Detection of RNA on Microarrays by Surface-Initiated Enzymatic Polymerization, Analytical Chemistry 2013, 85, 426-433.
Woolly Mammoth Revival, "Why Bring Back the Woolly Mammoth?" Revive & Restore 2021, in 3 pages. http://reviverestore.org/projects/woolly-mammoth/.
Yang et al., "Mutational Analysis of Residues in the Nucleotide Binding Domain of Human Terminal Deoxynucleotidyl Transferase," The Journal of Biological Chemistry 1994, 269(16), 11859-11868.
Yazdi et al., "Portable and Error-Free DNA-Based Data Storage," Scientific Reports 2017, 7(5011), 1-6.
International Search Report and Written Opinion dated Jan. 24, 2022 in PCT Patent Application No. PCT/US2021/031843.
Jena Bioscience, "Azide-PEG4-aminoallyl-dUTP Data Sheet", 2020, in 1 page.
Sørensen et al., "Enzymatic Ligation of Large Biomolecules to DNA", ACS NANO 2013, 7(9), 8098-8104.
Winz et al., "Site-specific one-pot triple click labeling for DNA and RNA", Chemical Communications 2018, 54(83), 11781-11784.
Deshpande et al., "Enzymatic synthesis and modification of high molecular weight DNA using terminal deoxynucleotidyl transferase," Methods Enzymol 2019, 627, 163-188.
Hayes et al., "Combining computational and experimental screening for rapid optimization of protein properties," PNAS 2002, 99(25), 15926-15931.
Motea & Berdis, "Terminal Deoxynucleotidyl Transferase: The Story of a Misguided DNA Polymerase," Biochim Biophys Acta 2010, 1804(5), 1151-1166.
Miura et al. "Triazole linking for preparation of a next-generation sequencing library from single-stranded DNA," Nucleic acids research 46.16 (2018): e95.

\* cited by examiner

|  |  |  | His tag | Thrombin cleavage site | SUMO fragment |  |
|---|---|---|---|---|---|---|

SEQ ID NO: 14  SUMO-TdT    1    MGSSHHHHHH  HHSSGLVPRG  SASMSDSEVN  QEAKPEVKPE  VKPETHINLK  VSDGSSEIFF  60

SEQ ID NO: 1   SUMO-TdT    61   KIKKTTPLRR  LMEAFAKRQG  KEMDSLRFLY  DGIRIQADQT  PEDLDMEDND  IIEAHREQIG  120

SEQ ID NO: 1   SUMO-TdT    121  LMRTDYSATP  NPGFQKTPPL  AVKKISQYAC  QRKTTLNNYN  HIFTDAFEIL  AENS F  NE  180
Amino Acids 139-  Bovine TdT  139  RTDYSATP   NPGFQKTPPL  AVKKISQYAC  QRKTTLNNYN  HIFTDAFEIL  AENS F  NE  194
520 of SEQ ID                                                                              175    177
NO: 12                                                                                     191 193 178
                                                                                                   194

SUMO-TdT    181  VSYVTFMRAA  SVLKSLPFTI  ISMKDTEGIP  CLGDKVKCII  EEIIEGESS   EVKAVLNDER  240
               Bovine TdT  197  VSYVTFMRAA  SVLKSLPFTI  ISMKDTEGIP  CLGDKVKCII  EEIIEGESS   EVKAVLNDER  256
                                                                                 226
                                                                                 242

SUMO-TdT    241  YQSFKLFTSV  FGVGLKTSEK  WFRMGFRSLS  IMSDKTLK    TK QKAGFLY  YEDLVSCVTR  300
               Bovine TdT  257  YQSFKLFTSV  FGVGLKTSEK  WFRMGFRSLS  IMSDKTLK    TK QKAGFLY  YEDLVSCVTR  316
                                                                   271 280      283
                                                                   287 296      299

SUMO-TdT    301  AEAEAVGVLV  KEAVWAFLPD  AFVTMGGFR   RGKKIGHDVD  FLITSPGSAE  DEEQLLPKVI  360
               Bovine TdT  317  AEAEAVGVLV  KEAVWAFLPD  AFVTMGGFR   RGKKIGHDVD  FLITSPGSAE  DEEQLLPKVI  376
                                                       326
                                                       342

SUMO-TdT    361  NLWEKKGLLL  YYDLVESTFE  KFKLPSRQVD  TLDHFQKCFL  ILKL HQRVD  SSKSNQQEGK  420
               Bovine TdT  377  NLWEKKGLLL  YYDLVESTFE  KFKLPSRQVD  TLDHFQKCFL  ILKL HQRVD  SSKSNQQEGK  436
                                                                                405
                                                                                421

SUMO-TdT    421  TWKAIRVDLV  MCPYENRAFA  LLGWTGSRQF  ERDIRRYATH  ERKMMLDNHA  LYDKTKRVFL  480
               Bovine TdT  437  TWKAIRVDLV  MCPYENRAFA  LLGWTGSRQF  ERDIRRYATH  ERKMMLDNHA  LYDKTKRVFL  496

SUMO-TdT    481  KAESEEEIFA  HLGLDYIEPW  ERNA  504
               Bovine TdT  497  KAESEEEIFA  HLGLDYIEPW  ERNA  520

FIG. 1

\*: 0.01 < p-value ≤ 0.05
\*\*: 0.001 < p-value ≤ 0.01
\*\*\*: p-value ≤ 0.001

| Reaction temp. (°C) | 25 | | | | | | | | | | | |
|---|---|---|---|---|---|---|---|---|---|---|---|---|
| Enzyme | NEB TdT | | | | WT TdT | | | | TdT3-2 | | | |
| dCTP | Yes | | | No | Yes | | | No | Yes | | | No |
| Reaction duration (min) | 5 | 10 | 20 | 20 | 5 | 10 | 20 | 20 | 5 | 10 | 20 | 20 |

| Reaction temp. (°C) | 36 | | | | | | | | | | | |
|---|---|---|---|---|---|---|---|---|---|---|---|---|
| Enzyme | NEB TdT | | | | WT TdT | | | | TdT3-2 | | | |
| dCTP | Yes | | | No | Yes | | | No | Yes | | | No |
| Reaction duration (min) | 5 | 10 | 20 | 20 | 5 | 10 | 20 | 20 | 5 | 10 | 20 | 20 |

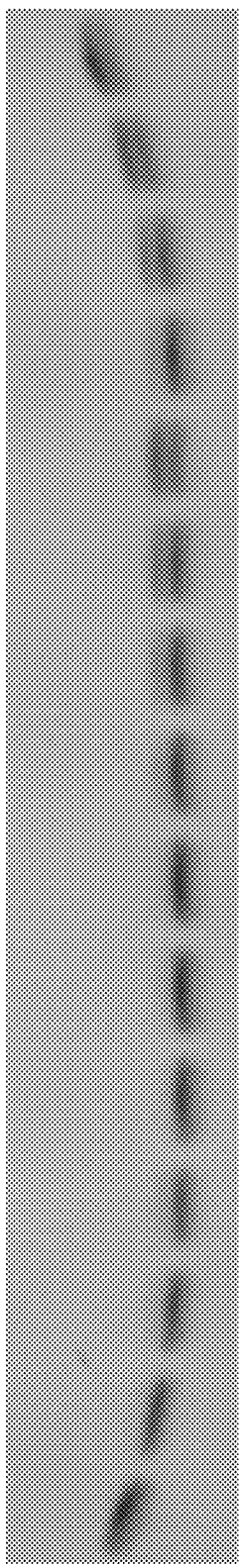
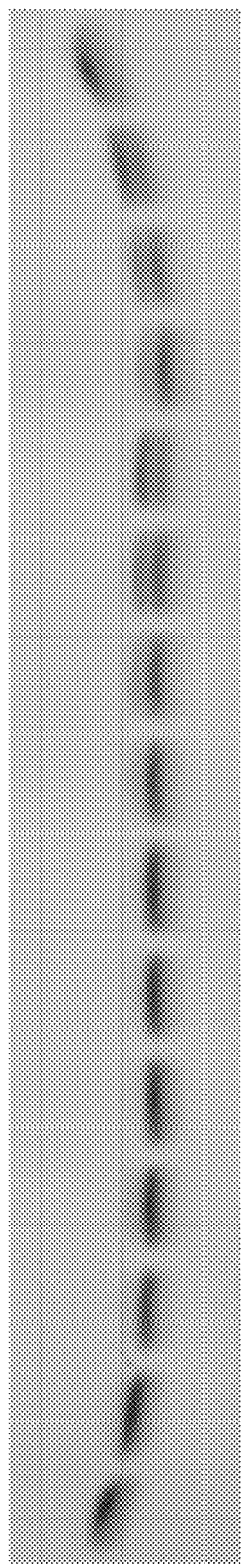
FIG. 12

THERMOSTABLE TERMINAL DEOXYNUCLEOTIDYL TRANSFERASE

CROSS-REFERENCE TO RELATED APPLICATIONS

This application claims the benefit of priority to U.S. Provisional Patent Application No. 63/023,734, filed May 12, 2020, the content of which is incorporated herein by reference in its entirety.

PARTIES TO A JOINT RESEARCH AGREEMENT

The claimed invention was made by, on behalf of, and/or in connection with one or more of the following parties to a joint research agreement: Illumina Singapore Pte. Ltd. and National University of Singapore. The joint research agreement was in effect on or before the date the claimed invention was made, and the claimed invention was made as a result of activities undertaken within the scope of the joint research agreement.

REFERENCE TO SEQUENCE LISTING

The present application is being filed along with a Sequence Listing in electronic format. The Sequence Listing is provided as a file entitled Sequences_Listing_47CX-311971-US, created May 11, 2021, which is 56 kilobytes in size. The information in the electronic format of the Sequence Listing is incorporated herein by reference in its entirety.

BACKGROUND

Field

The present disclosure relates generally to the field of recombinant proteins for example recombinant terminal deoxynucleotidyl transferase.

Description of the Related Art

Terminal deoxynucleotidyl transferase (TdT) catalyzes template free incorporation of arbitrary nucleotides onto single-stranded DNA. However, wild-type (WT) TdT is not optimized for the incorporation of 3' modified nucleotides. Furthermore, TdT is marginally stable, so evolution for the ability for 3' block incorporation will likely lead to an unstable mutant as most mutations lead to a drop in thermostability. Hence there is a need for a thermostable TdT variant that can serve as the starting point for evolution of a mutant which enables efficient incorporation of 3'-modified nucleotides.

SUMMARY

Disclosed herein include embodiments of a recombinant terminal deoxynucleotidyl transferase (TdT). In some embodiments, the recombinant TdT comprises an amino acid sequence that is at least 80% identical to SEQ ID NO: 1, wherein the recombinant TdT comprises one or more amino acid substitution mutations at one or more positions functionally equivalent to Glu191, Lys193, Glu194, Asp242, Lys287, Phe296, Met299, Thr342, and His421 in the Bos taurus TdT of SEQ ID NO: 12.

In some embodiments, the amino acid substitution mutation at the position functionally equivalent to Glu191 in the Bos taurus TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Glu191 can comprise a mutation to a nonpolar amino acid, a hydrophobic amino acid, an aliphatic amino acid, or a branched-chain amino acid. The amino acid substitution mutation at the position functionally equivalent to Glu191 in the Bos taurus TdT of SEQ ID NO: 12 can be Glu191Ala, Glu191Arg, Glu191Asn, Glu191Asp, Glu191Cys, Glu191Gln, Glu191Gly, Glu191His, Glu191Ile, Glu191Leu, Glu191Lys, Glu191Met, Glu191Phe, Glu191Pro, Glu191Ser, Glu191Thr, Glu191Trp, Glu191Tyr, or Glu191Val. The amino acid substitution mutation at the position functionally equivalent to Glu191 in the Bos taurus TdT of SEQ ID NO: 12 can be Glu191Ala, Glu191Gly, Glu191Ile, Glu191Leu, Glu191Met, or Glu191Val. The amino acid substitution mutation at the position functionally equivalent to Glu191 in the Bos taurus TdT of SEQ ID NO: 12 can be Glu191Val.

In some embodiments, the amino acid substitution mutation at the position functionally equivalent to Lys193 in the Bos taurus TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Lys193 in the Bos taurus TdT of SEQ ID NO: 12 can comprise a mutation to a polar amino acid or a hydrophilic amino acid. The amino acid substitution mutation at the position functionally equivalent to Lys193 in the Bos taurus TdT of SEQ ID NO: 12 can be Lys193Ala, Lys193Arg, Lys193Asn, Lys193Asp, Lys193Cys, Lys193Gln, Lys193Glu, Lys193Gly, Lys193His, Lys193Ile, Lys193Leu, Lys193Met, Lys193Phe, Lys193Pro, Lys193Ser, Lys193Thr, Lys193Trp, Lys193Tyr, or Lys193Val. The amino acid substitution mutation at the position functionally equivalent to Lys193 in the Bos taurus TdT of SEQ ID NO: 12 can be Lys193Asn, Lys193Gln, Lys193Ser, or Lys193Thr. The amino acid substitution mutation at the position functionally equivalent to Lys193 in the Bos taurus TdT of SEQ ID NO: 12 can be Lys193Asn.

In some embodiments, the amino acid substitution mutation at the position functionally equivalent to Glu194 in the Bos taurus TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Glu194 in the Bos taurus TdT of SEQ ID NO: 12 can comprise a mutation to a nonpolar amino acid, a hydrophobic amino acid, an aliphatic amino acid, or a branched-chain amino acid. The amino acid substitution mutation at the position functionally equivalent to Glu194 in the Bos taurus TdT of SEQ ID NO: 12 can be Glu194Ala, Glu194Arg, Glu194Asn, Glu194Asp, Glu194Cys, Glu194Gln, Glu194Gly, Glu194His, Glu194Ile, Glu194Leu, Glu194Lys, Glu194Met, Glu194Phe, Glu194Pro, Glu194Ser, Glu194Thr, Glu194Trp, Glu194Tyr, or Glu194Val. The amino acid substitution mutation at the position functionally equivalent to Glu194 in the Bos taurus TdT of SEQ ID NO: 12 can be Glu194Ala, Glu194Gly, Glu194Ile, Glu194Leu, Glu194Met, or Glu194Val. The amino acid substitution mutation at the position functionally equivalent to Glu194 in the *Bos taurus* TdT of SEQ ID NO: 12 can be Glu194Gly.

In some embodiments, the amino acid substitution mutation at the position functionally equivalent to Asp242 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Asp242 in the *Bos taurus* TdT of SEQ ID NO: 12 can comprise a mutation to a polar amino acid or an aromatic amino acid. The amino acid substitution mutation at the position functionally equivalent to Asp242 in the *Bos taurus* TdT of SEQ ID NO: 12 can be Asp242Ala, Asp242Arg, Asp242Asn, Asp242Cys, Asp242Gln, Asp242Glu, Asp242Gly, Asp242His, Asp242Ile, Asp242Leu, Asp242Lys, Asp242Met, Asp242Phe, Asp242Pro, Asp242Ser, Asp242Thr, Asp242Trp, Asp242Tyr, or Asp242Val. The amino acid substitution mutation at the position functionally equivalent to Asp242 in the *Bos taurus* TdT of SEQ ID NO: 12 can be Asp242Asn, Asp242Gln, Asp242Phe, Asp242Ser, Asp242Thr, Asp242Trp, or Asp242Tyr. The amino acid substitution mutation at the position functionally equivalent to Asp242 in the *Bos taurus* TdT of SEQ ID NO: 12 can be Asp242Tyr.

In some embodiments, the amino acid substitution mutation at the position functionally equivalent to Lys287 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Lys287 in the *Bos taurus* TdT of SEQ ID NO: 12 can comprise a mutation to a polar amino acid, a negatively charged amino acid or a hydrophilic amino acid. The amino acid substitution mutation at the position functionally equivalent to Lys287 in the *Bos taurus* TdT of SEQ ID NO: 12 can be Lys287Ala, Lys287Arg, Lys287Asn, Lys287Asp, Lys287Cys, Lys287Gln, Lys287Glu, Lys287Gly, Lys287His, Lys287Ile, Lys287Leu, Lys287Met, Lys287Phe, Lys287Pro, Lys287Ser, Lys287Thr, Lys287Trp, Lys287Tyr, or Lys287Val. The amino acid substitution mutation at the position functionally equivalent to Lys287 in the *Bos taurus* TdT of SEQ ID NO: 12 can be Lys287Asp or Lys287Glu. The amino acid substitution mutation at the position functionally equivalent to Lys287 in the *Bos taurus* TdT of SEQ ID NO: 12 can be Lys287Glu.

In some embodiments, the amino acid substitution mutation at the position functionally equivalent to Phe296 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Phe296 in the *Bos taurus* TdT of SEQ ID NO: 12 can comprise a mutation to a nonpolar amino acid, a hydrophobic amino acid, an aliphatic amino acid, or a branched-chain amino acid. The amino acid substitution mutation at the position functionally equivalent to Phe296 in the *Bos taurus* TdT of SEQ ID NO: 12 can be Phe296Ala, Phe296Arg, Phe296Asn, Phe296Asp, Phe296Cys, Phe296Gln, Phe296Glu, Phe296Gly, Phe296His, Phe296Ile, Phe296Leu, Phe296Lys, Phe296Met, Phe296Pro, Phe296Ser, Phe296Thr, Phe296Trp, Phe296Tyr, or Phe296Val. The amino acid substitution mutation at the position functionally equivalent to Phe296 in the *Bos taurus* TdT of SEQ ID NO: 12 can be Phe296Ala, Phe296Gly, Phe296Ile, Phe296Leu, Phe296Met, or Phe296Val. The amino acid substitution mutation at the position functionally equivalent to Phe296 in the *Bos taurus* TdT of SEQ ID NO: 12 can be Phe296Leu.

In some embodiments, the amino acid substitution mutation at the position functionally equivalent to Met299 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Met299 in the *Bos taurus* TdT of SEQ ID NO: 12 can comprise a mutation to a polar amino acid, a positively charged amino acid, or a hydrophilic amino acid. The amino acid substitution mutation at the position functionally equivalent to Met299 in the *Bos taurus* TdT of SEQ ID NO: 12 can be Met299Ala, Met299Arg, Met299Asn, Met299Asp, Met299Cys, Met299Gln, Met299Glu, Met299Gly, Met299His, Met299Ile, Met299Leu, Met299Lys, Met299Phe, Met299Pro, Met299Ser, Met299Thr, Met299Trp, Met299Tyr, or Met299Val. The amino acid substitution mutation at the position functionally equivalent to Met299 in the *Bos taurus* TdT of SEQ ID NO: 12 can be Met299Arg, Met299His, or Met299Lys. The amino acid substitution mutation at the position functionally equivalent to Met299 in the *Bos taurus* TdT of SEQ ID NO: 12 can be Met299Lys.

In some embodiments, the amino acid substitution mutation at the position functionally equivalent to Thr342 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Thr342 in the *Bos taurus* TdT of SEQ ID NO: 12 can comprise a mutation to a polar amino acid, an aliphatic amino acid, or a hydrophilic amino acid. The amino acid substitution mutation at the position functionally equivalent to Thr342 in the *Bos taurus* TdT of SEQ ID NO: 12 can be Thr342Ala, Thr342Arg, Thr342Asn, Thr342Asp, Thr342Cys, Thr342Gln, Thr342Glu, Thr342Gly, Thr342His, Thr342Ile, Thr342Leu, Thr342Lys, Thr342Met, Thr342Phe, Thr342Pro, Thr342Ser, Thr342Trp, Thr342Tyr, or Thr342Val. The amino acid substitution mutation at the position functionally equivalent to Thr342 in the *Bos taurus* TdT of SEQ ID NO: 12 can be Thr342Asn, Thr342Cys, Thr342Gln, Thr342Pro, or Thr342Ser. The amino acid substitution mutation at the position functionally equivalent to Thr342 in the *Bos taurus* TdT of SEQ ID NO: 12 can be Thr342Ser.

In some embodiments, the amino acid substitution mutation at the position functionally equivalent to His421 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to His421 in the *Bos taurus* TdT of SEQ ID NO: 12 can comprise a mutation to a polar amino acid, an aliphatic amino acid, or a hydrophilic amino acid. The amino acid substitution mutation at the position functionally equivalent to His421 in the *Bos taurus* TdT of SEQ ID NO: 12 can be His421Ala, His421Arg, His421Asn, His421Asp, His421Cys, His421Gln, His421Glu, His421Gly, His421Ile, His421Leu, His421Lys, His421Met, His421Phe, His421Pro, His421 Ser, His421Thr, His421Trp, His421Tyr, or His421Val. The amino acid substitution mutation at the position functionally equivalent to His421 in the *Bos taurus* TdT of SEQ ID NO: 12 can be His421Asn, His421Cys, His421Gln, His421Pro, His421Ser, or His421Thr. The amino acid substitution mutation at the position functionally equivalent to His421 in the *Bos taurus* TdT of SEQ ID NO: 12 can be His421Pro.

In some embodiments, the recombinant TdT comprises two or more amino acid substitution mutations at two or more positions functionally equivalent to Glu191, Lys193, Glu194, Asp242, Lys287, Phe296, Met299, Thr342, and His421 in the *Bos taurus* TdT of SEQ ID NO: 12. The two or more amino acid substitution mutations at the two or more positions functionally equivalent to Glu191, Lys193, Glu194, Asp242, Lys287, Phe296, Met299, Thr342, and His421 in the *Bos taurus* TdT of SEQ ID NO: 12 can comprise two or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises three or more amino acid substitution mutations at three or more positions functionally equivalent to Glu191, Lys193, Glu194, Asp242, Lys287, Phe296, Met299, Thr342, and His421 in the *Bos taurus* TdT of SEQ ID NO: 12. The three or more amino acid substitution mutations at the three or more positions functionally equivalent to Glu191, Lys193, Glu194, Asp242, Lys287, Phe296, Met299, Thr342, and His421 in the *Bos taurus* TdT of SEQ ID NO: 12 can comprise three or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises four or more amino acid substitution mutations at four or more positions functionally equivalent to Glu191, Lys193, Glu194, Asp242, Lys287, Phe296, Met299, Thr342, and His421 in the *Bos taurus* TdT of SEQ ID NO: 12. The four or more amino acid substitution mutations at the four or more positions functionally equivalent to Glu191, Lys193, Glu194, Asp242, Lys287, Phe296, Met299, Thr342, and His421 in the *Bos taurus* TdT of SEQ ID NO: 12 can comprise four or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises five or more amino acid substitution mutations at five or more positions functionally equivalent to Glu191, Lys193, Glu194, Asp242, Lys287, Phe296, Met299, Thr342, and His421 in the *Bos taurus* TdT of SEQ ID NO: 12. The five or more amino acid substitution mutations at the five or more positions functionally equivalent to Glu191, Lys193, Glu194, Asp242, Lys287, Phe296, Met299, Thr342, and His421 in the *Bos taurus* TdT of SEQ ID NO: 12 can comprise five or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises six or more amino acid substitution mutations at six or more positions functionally equivalent to Glu191, Lys193, Glu194, Asp242, Lys287, Phe296, Met299, Thr342, and His421 in the *Bos taurus* TdT of SEQ ID NO: 12. The six or more amino acid substitution mutations at the six or more positions functionally equivalent to Glu191, Lys193, Glu194, Asp242, Lys287, Phe296, Met299, Thr342, and His421 in the *Bos taurus* TdT of SEQ ID NO: 12 can comprise six or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises seven or more amino acid substitution mutations at seven or more positions functionally equivalent to Glu191, Lys193, Glu194, Asp242, Lys287, Phe296, Met299, Thr342, and His421 in the *Bos taurus* TdT of SEQ ID NO: 12. The seven or more amino acid substitution mutations at the seven or more positions functionally equivalent to Glu191, Lys193, Glu194, Asp242, Lys287, Phe296, Met299, Thr342, and His421 in the *Bos taurus* TdT of SEQ ID NO: 12 can comprise seven or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises eight or more amino acid substitution mutations at eight or more positions functionally equivalent to Glu191, Lys193, Glu194, Asp242, Lys287, Phe296, Met299, Thr342, and His421 in the *Bos taurus* TdT of SEQ ID NO: 12. The eight or more amino acid substitution mutations at the eight or more positions functionally equivalent to Glu191, Lys193, Glu194, Asp242, Lys287, Phe296, Met299, Thr342, and His421 in the *Bos taurus* TdT of SEQ ID NO: 12 can comprise eight or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises eight amino acid substitution mutations at eight positions functionally equivalent to Lys193, Glu194, Asp242, Lys287, Phe296, Met299, Thr342, and His421 in the *Bos taurus* TdT of SEQ ID NO: 12. The eight amino acid substitution mutations at the eight positions functionally equivalent to Lys193, Glu194, Asp242, Lys287, Phe296, Met299, Thr342, and His421 in the *Bos taurus* TdT of SEQ ID NO: 12 can be Lys193Asn, Glu194Gly, Asp242Tyr, Lys287Glu, Phe296Leu, Met299Lys, Thr342Ser, and His421Pro, respectively.

In some embodiments, the recombinant TdT comprises nine amino acid substitution mutations at positions functionally equivalent to Glu191, Lys193, Glu194, Asp242, Lys287, Phe296, Met299, Thr342, and His421 in the *Bos taurus* TdT of SEQ ID NO: 12. The nine amino acid substitution mutations at the positions functionally equivalent to Glu191, Lys193, Glu194, Asp242, Lys287, Phe296, Met299, Thr342, and His421 in the *Bos taurus* TdT of SEQ ID NO: 12 can be Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises an amino acid sequence that is at least 85% identical to SEQ ID NO: 1. The recombinant TdT comprises an amino acid sequence that can be at least 90% identical to SEQ ID NO: 1. The recombinant TdT comprises an amino acid sequence that can be at least 95% identical to SEQ ID NO: 1. The recombinant TdT comprises an amino acid sequence that can be at least 95% identical to SEQ ID NO: 11. The recombinant TdT comprises an amino acid sequence that can be at least 80% identical to SEQ ID NO: 12.

In some embodiments, the recombinant TdT is stable at a temperature of 47° C. or higher. The recombinant TdT can be stable at a temperature of 50° C. or higher. The recombinant TdT can be stable at a temperature of 55° C. or higher. The recombinant TdT can be stable at a temperature of 58° C. or higher. In some embodiments, the terminal deoxynucleotidyl transferase activity of the recombinant TdT is at least 80%, 85%, 90%, 95%, 100%, 105%, 110%, 115%, or 120%, of the terminal deoxynucleotidyl transferase activity of the Bos taurus TdT of SEQ ID NO: 12 at a same test temperature. The test temperature can be 37° C., 47° C., 50° C., 55° C., or 58° C.

In some embodiments, the recombinant TdT comprises a small ubiquitin-like modifier (SUMO) fragment. The SUMO fragment comprises an amino acid sequence that can be at least 80% identical to SEQ ID NO: 13. The recombinant TdT can comprise the SUMO fragment on the N-terminus of the recombinant TdT. The recombinant TdT can comprise an amino acid sequence that is at least 80% identical to SEQ ID NO: 14. The recombinant TdT can comprise an amino acid sequence that is at least 80% identical to SEQ ID NO: 15. The recombinant TdT can comprise the SUMO fragment on the C-terminus of the recombinant TdT.

Disclosed herein include embodiments of a polynucleotide encoding a recombinant terminal deoxynucleotidyl transferase (TdT) of the present disclosure. Disclosed herein include embodiments of an expression vector comprising a polynucleotide encoding a recombinant terminal deoxynucleotidyl transferase (TdT) of the present disclosure. Disclosed herein include embodiments of a host cell comprising a recombinant terminal deoxynucleotidyl transferase of the present disclosure. Disclosed herein include embodiments of a host cell comprising a polynucleotide encoding a recombinant terminal deoxynucleotidyl transferase (TdT) of the present disclosure. Disclosed herein include embodiments of a host cell comprising an expression vector comprising a polynucleotide encoding a recombinant terminal deoxynucleotidyl transferase of the present disclosure.

Disclosed herein include kits. In some embodiments, a kit comprises: a recombinant terminal deoxynucleotidyl transferase (TdT) of the present disclosure; and instructions for using the recombinant terminal deoxynucleotidyl transferase. In some embodiments, a kit comprises: a polynucleotide encoding a recombinant terminal deoxynucleotidyl transferase of the present disclosure; and instructions for using the polynucleotide and/or the recombinant terminal deoxynucleotidyl transferase. In some embodiments, a kit comprises: an expression vector comprising a polynucleotide encoding a recombinant terminal deoxynucleotidyl transferase of the present disclosure; and instructions for using the expression vector, the polynucleotide, and/or the recombinant terminal deoxynucleotidyl transferase. In some embodiments, a kit comprises: a host cell comprising a recombinant terminal deoxynucleotidyl transferase of the present disclosure, a polynucleotide encoding the recombinant terminal deoxynucleotidyl transferase, an expression vector comprising the polynucleotide encoding the recombinant terminal deoxynucleotidyl transferase, or a combination thereof; and instructions for using the recombinant terminal deoxynucleotidyl transferase, the polynucleotide, the expression vector, the host cell, or a combination thereof.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 1 shows a non-limiting exemplary sequence alignment of SUMO-TdT (SEQ ID NO: 14) with amino acids 139-520 (SEQ ID NO: 1) of Bos taurus TdT (SEQ ID NO: 12). SUMO-TdT refers to a recombinant TdT that contains amino acids 139-520 of Bos taurus TdT at amino acid positions 123-504 and an N-terminal SUMO-tag (SEQ ID NO: 13) at amino acid positions 22-119. The positions of the substitution mutations in SUMO-TdT (and TdT variants thereof) identified herein and corresponding positions in Bos taurus TdT are highlighted.

FIG. 3A is a non-limiting exemplary schematic illustration of FRET reaction to detect incorporation of Cy5-dCTP by active TdT onto an oligo with FAM dye on a nucleotide two bases away from 3'-OH (2bA FAM). FIG. 3B shows a preliminary test of the schematic illustration in FIG. 3A to detect purified TdT activity which corresponds to increase of Cy5 emission at 670 nm with FAM excitation wavelength of 450 nm. FIG. 3C is a non-limiting exemplary schematic illustration showing at high concentration, endogenous nucleases in the cell lysate degrade the oligo substrate. Dilution of the lysate disproportionately lowers nuclease activity compared to TdT, allowing detection of TdT activity. Scissors symbol refers to nuclease. Star symbol refers to active TdT. FIG. 3D is a gel image showing the results of various dilutions of TdT expressing cell lysates in TdT buffer, incubated with 5' FAM-tagged oligo (FAM20) and dCTP. Higher bands indicative of TdT activity (boxed) are seen only at 50× and 500× dilution, while lower dilution leads to degradation by endogenous nucleases (below blue line). FIG. 3E is a non-limiting exemplary plot showing the results of the 96 well Plate FRET assay with SUMO-TdT and empty plasmid using 50× diluted cell lysate. Higher FRET signal at 670 nm was observed for cell lysates expressing SUMO-TdT (red lines) but not those with an empty plasmid (blue lines), suggesting that this assay could be used to screen for active TdT.

FIG. 4A is a non-limiting exemplary plot of emission wavelength scans of oligo 1bA FAM with TAMRA-dCTP in the presence or absence of TdT. The decrease in FAM's emission at 520 nm was low which suggests inefficient transfer of energy to TAMRA dye. FIG. 4B is a non-limiting exemplary plot of emission wavelength scans of oligo 2bA FAM with TAMRA-dCTP in the presence or absence of TdT. With incubation with TdT, the decrease in emission signal from FAM and gain of emission signal from TAMRA seems to be the best among the four oligos examined. FIG. 4C is a non-limiting exemplary plot of emission wavelength scans of oligo 5bA FAM with TAMRA-dCTP in the presence or absence of TdT. The decrease of FAM's emission signal and gain of TAMRA's emission signal when TdT was present were lower than that shown in FIG. 4B. FIG. 4D is a non-limiting exemplary plot of emission wavelength scans of oligo 10bA FAM with TAMRA-dCTP in the presence or absence of TdT. There was no difference in emission signal of FAM and TAMRA between presence and absence of TdT.

FIG. 5A is a non-limiting exemplary plot of emission wavelength scans of 2bA FAM oligo and TAMRA-dCTP in the presence or absence of TdT. Emission wavelengths were scanned from 480 nm to 700 nm with excitation at 450 nm. 2bA oligo did not show strong signal at 575 nm which corresponds to emission of TAMRA acceptor dye. FIG. 5B is a non-limiting exemplary plot of emission wavelength scans of 2bA FAM oligo and Cy5-dCTP in the presence or absence of TdT. Emission wavelengths were scanned from 480 nm to 700 nm with excitation at 450 nm. There was an increase of signal at 670 nm when TdT was present. This suggests successful detection of active TdT using FAM and Cy5 FRET pairs. FIG. 5C is a non-limiting exemplary plot of emission wavelength scans of 2bA FAM oligo and Cy3-dCTP in the presence or absence of TdT. Emission wavelengths were scanned from 530 nm to 700 nm with excitation at 500 nm. Oligo with Cy3 dye labelled on a base two bases from 3'-OH was incubated with Cy5-dCTP and TdT. There was a lower gain of signal at 670 nm compared to that in FIG. 5B.

FIG. 7A is a non-limiting exemplary histogram showing a comparison of the FRET activity of SUMO-TdT and mutants TdT1-1 and TdT1-2. Unheated treatment refers to no heat treatment of cell lysate prior to incorporation reaction, and heated treatment refers to cell lysate heated at 47° C. for 1 min prior to reaction. FRET readout of SUMO-TdT, TdT1-1, TdT1-2 between $15^{th}$ min and $30^{th}$ of the reaction time course were recorded, and the average values were displayed in the histogram above. Analysis using Student's T-Test with unequal variance was performed, which shows that the average FRET readout of SUMO-TdT, TdT1-1 and TdT1-2 is significantly different. Average activity ratio of TdT1-1 and TdT1-2 were calculated by dividing average heated FRET reading by average unheated FRET reading. TdT1-1 and TdT1-2 retained higher activity after heat treatment. Both are significantly higher than SUMO-TdT. FIG. 7B is a non-limiting exemplary histogram showing the second round of screening with heat treatment at 50° C. for 1 min identified mutants TdT2-1, TdT2-2, TdT2-3 and TdT2-4 which had significantly higher FRET values and activity ratio than parent TdT1-1. FIG. 7C is a non-limiting exemplary histogram showing the third round of screen using parent template TdT1-1 identified TdT3-1 to have significantly higher FRET readout and activity ratio than TdT1-1 after heat treatment at 55° C. FIG. 7D is a non-limiting exemplary histogram showing the third round of screen using parent template TdT1-3 (hybrid of TdT1-1 and TdT1-2), TdT3-2 was identified to have significantly higher FRET readout and retained significantly higher proportion of activity than TdT1-3 after 1 min heat treatment at 58° C.

FIG. 8A is a non-limiting exemplary gel image showing purification of SUMO-TdT and TdT3-2. The yield of urified SUMO-TdT and TdT3-2 was 8.5 mg/L culture and 14.1 mg/L culture respectively. SDS-PAGE gel of 1 µg of each dialyzed purified SUMO-TdT and TdT3-2. The expected size of SUMO-TdT is 57.9 kD and TdT3-2 is 57.7 kD. Major bands around 58 kD ladder were observed for both SUMO-TdT and TdT3-2 which corresponds to the respective proteins. The positions of the major bands suggest successful purification of SUMO-TdT and TdT3-2 via Nickel IMAC and Q Sepharose® (a crosslinked, beaded-form of agarose) IEX chromatography. FIG. 8B is a non-limiting exemplary gel image showing nuclease test to examine presence of nuclease contamination for purified SUMO-TdT and TdT3-2. Single stranded oligo substrate of 35 bases was incubated with individually with SUMO-TdT and TdT3-2. Samples were visualized on TBE-Urea gel. Bands observed smaller than 35 bases would suggest presence of nucleases in the protein sample that degrades the single stranded oligo substrate. Lane 3 is a control to demonstrate the expected observation of degraded DNA products when nucleases were present. Comparing lane 3, 4 and 5, there is much lesser smaller sized bands observed in lane 4 and 5. This suggests minimum nucleases were present in purified SUMO-TdT and TdT3-2.

FIG. 9A is a non-limiting exemplary plot of differential scanning calorimetry (DSC) of purified SUMO-TdT and TdT3-2. The peak of the graph corresponds to transition midpoint ($T_m$ or melting temperature) of the protein where 50% of the protein is unfolded. SUMO-TdT's average $T_m$ was 40.2° C. and TdT3-2's was 50.7° C. FIG. 9B is a non-limiting exemplary plot of differential scanning fluorimetry (DSF) of purified SUMO-TdT and TdT3-2. The peak observed in the graph of the negative derivative of F350 nm/F330 nm against temperature corresponds to the $T_m$ of the proteins. SUMO-TdT's average $T_m$ was 43.5° C. and TdT3-2 was 53.1° C. FIG. 9C is a non-limiting exemplary plot of the results of SYPRO Orange thermal shift assay of purified SUMO-TdT and TdT3-2. SYPRO Orange dye binds nonspecifically to hydrophobic regions in unfolded proteins. The peak observed in the –dRFU/temperature against temperature graph corresponds to the $T_m$ of SUMO-TdT and TdT3-2. The SUMO-TdT average $T_m$ was 41.5° C. and TdT3-2 was 51.5° C. FIG. 9D is a non-limiting exemplary plot of first derivative of CD Ellipticity at 222 nm as a function of temperature. The peak observed in the graph corresponds to the $T_m$ of the proteins. SUMO-TdT's average $T_m$ was 45.7° C. and TdT3-2 was 52.5° C.

(FIG. 10B) 36° C. FIG. 10C shows TdT3-2 can incorporate dCTP onto 5' FAM labelled oligo for 20 minutes at 47° C. as observed from higher sized bands DNA products, while NEB TdT and SUMO-TdT were denatured within 5 minutes. FIG. 10D shows only TdT3-2 was active at 58° C., albeit for less than 5 minutes. NEB TdT and SUMO-TdT were denatured.

FIG. 12 is a non-limiting exemplary gel graph showing ddCTP being incorporated onto FAM-tagged oligo with NEB TdT and TdT3-2. Intensity of the bands were analyzed using Bio-Rad Image Lab software and plotted using Graph-Pad. TdT3-2 incorporated more ddCTP than NEB TdT as observed by higher intensity +1 bands. At elevated temperature of 50° C., TdT3-2 incorporated more ddCTP than at 37° C. as observed by increased proportion of +1 bands at 50° C.

DETAILED DESCRIPTION

Figure 2:
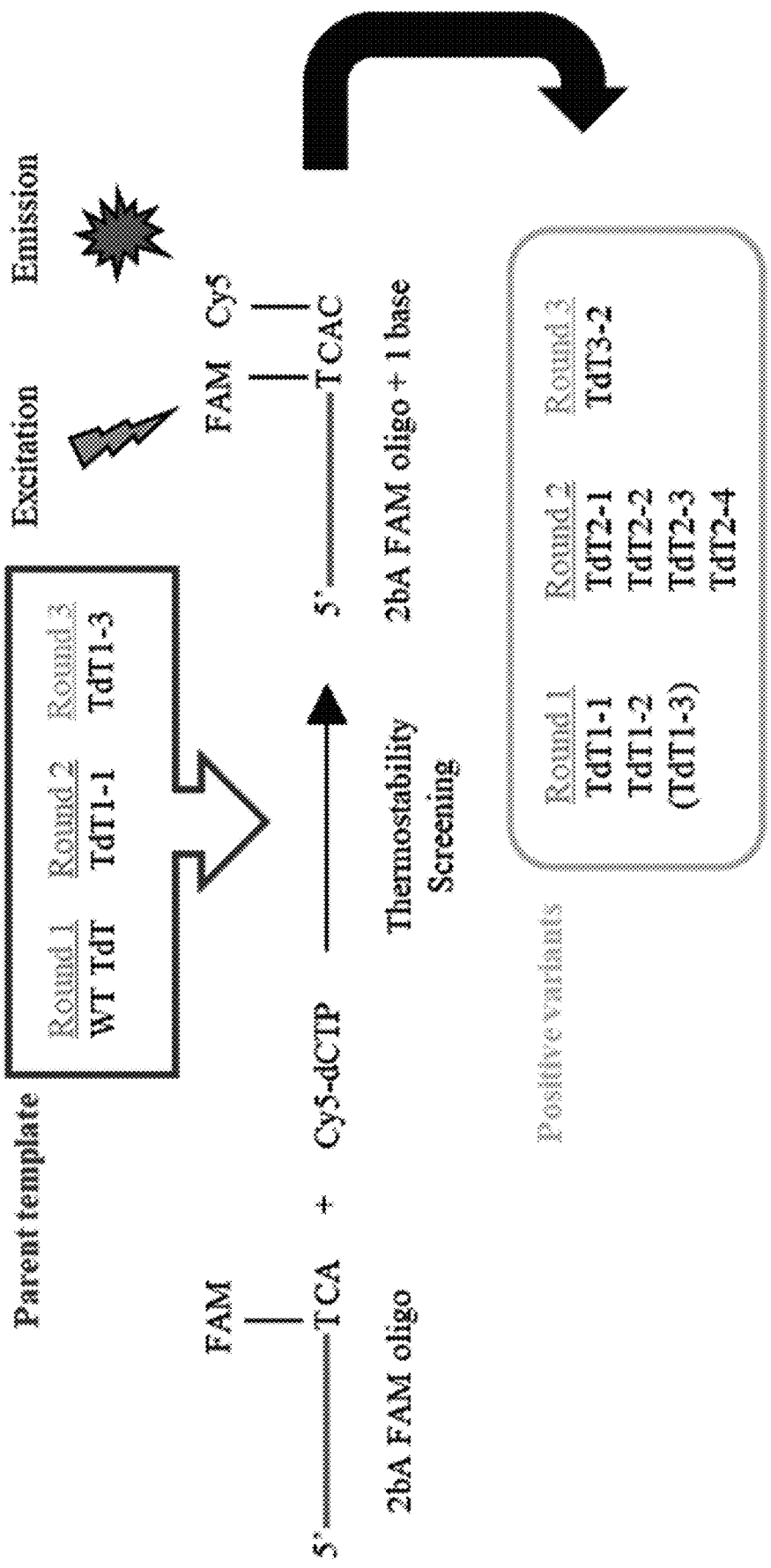
FIG. 2 is a non-limiting exemplary schematic illustration of FRET reaction to detect incorporation of Cy5-dCTP by active TdT onto an oligo with FAM dye on a nucleotide two bases away from 3'-OH (2bA FAM). The first round of screening used SUMO-TdT (which is a recombinant bovine TdT with the first 138 amino acids of the bovine TdT deleted and contains an N-terminal SUMO-tag which improves solubility and expression) as the parent template identified mutants TdT1-1 and TdT1-2 as thermostable. The second round of screening used TdT1-2 as the parent template and was conducted with heat treatment of 50° C. for 1 min and four thermostable mutants were identified (TdT2-1, TdT2-2, TdT2-3, TdT2-4). The third round of screening used TdT1-1 and TdT1-3 as the parent templates with different combinations of the mutations found in TdT2-1, TdT2-2, TdT2-3 and TdT2-4 and identified TdT3-2 as thermostable.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Sequencing by synthesis technology has enabled the discovery of vast quantities of information about the underlying source code of life. In order to fully benefit from this information, it is necessary to create fully synthetic genes and genomes to test whether the understanding derived from sequencing can be used to create new systems predictably. For instance, it has been demonstrated the construction of synthetic organisms using genomes constructed using chemically synthesized oligos. Similarly, efforts to create synthetic yeast and E. coli with only 57 instead of 64 codons or even to regenerate extinct organisms (refs 6 and 7) represent the next step forward in biological engineering.

However, this effort is hindered by the fact that current oligonucleotide and gene synthesis methods rely on chemical synthesis using phosphoramidite chemistry. This method imposes many limitations like a maximum size of less than 200 bp due to deletions and side-reactions, as well the use and generation of environmentally harmful organic chemicals and waste products. As a result, the cost of genome scale construction runs into the millions of dollars, which represents a major obstacle.

Wild-type terminal deoxynucleotidyl transferase is quite unstable and is not optimized for enzymatic oligonucleotide and gene synthesis using step wise incorporation of a single 3' blocked nucleotide into a growing ssDNA strand and deprotection. Engineered TdT that can accept 3' blocked nucleotides as well as with increased activity and robustness is needed.

Terminal deoxynucleotidyl transferase (TdT) catalyzes template free incorporation of arbitrary nucleotides onto single-stranded DNA. TdT has been widely used in biotechnology and clinical applications. One possible use is the synthesis of long de novo DNA molecules by TdT-mediated iterative incorporation of a 3' reversibly blocked nucleotide, followed by deblocking. However, wild-type (WT) TdT is not optimized for the incorporation of 3' modified nucleotides, and TdT engineering is hampered by the fact that TdT is marginally stable and only present in mesophilic organisms. A thermostable TdT variant can serve as backbone for subsequent evolutions to enable efficient incorporation of 3'-modified nucleotides. A thermostable variant would be a good starting point for such an effort, as evolution to incorporate bulky modified nucleotides generally results in lowered stability. In addition, a thermostable TdT would also be useful in situations where DNA secondary structures inhibit WT activity, as higher temperature could be used to melt dsDNA. An assay described in the present disclosure was developed to identify thermostable TdT variants. After screening about 10,000 TdT mutants, a variant, named TdT3-2, that was 10° C. more thermostable than SUMO-TdT and preserved the catalytic properties of the WT enzyme, was identified. Any recombinant TdT disclosed herein can be used as a scaffold for evolution of TdT that can incorporate 3' blocked nucleotides onto single-stranded DNA.

Some embodiments of a recombinant terminal deoxynucleotidyl transferase (TdT) are provided herein. In some embodiments, the recombinant TdT comprises an amino acid sequence that is at least 80% identical to SEQ ID NO: 1, wherein the recombinant TdT comprises one or more amino acid substitution mutations at one or more positions functionally equivalent to Glu191, Lys193, Glu194, Asp242, Lys287, Phe296, Met299, Thr342, and His421 in the Bos taurus TdT of SEQ ID NO: 12. Disclosed herein include embodiments of a polynucleotide encoding the recombinant terminal deoxynucleotidyl transferase. Disclosed herein include embodiments of an expression vector comprising the polynucleotide encoding the recombinant terminal deoxynucleotidyl transferase. Disclosed herein include embodiments of a host cell comprising the recombinant terminal deoxynucleotidyl transferase. Disclosed herein include embodiments of a host cell comprising a polynucleotide encoding the recombinant terminal deoxynucleotidyl transferase. Disclosed herein include embodiments of a host cell comprising an expression vector comprising a polynucleotide encoding the recombinant terminal deoxynucleotidyl.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using a sequence comparison algorithm or by visual inspection.

The phrase "substantially identical," in the context of two nucleic acids or polypeptides (e.g., DNAs encoding a protein, or the amino acid sequence of a protein) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. The "substantial identity" can exist over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN) are available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm, by the homology alignment algorithm, by the search for similarity method, by computerized implementations of these algorithms, or by visual inspection. One example of an algorithm that is suitable for determining percent sequence identity and sequence similarity is the BLAST algorithm. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Amino acids at "functionally equivalent" amino acid positions can have the same functional role in the proteins (e.g., enzymes). Generally, functionally equivalent substitution mutations in two or more different proteins occur at homologous amino acid positions in the amino acid sequences of the proteins. Hence, used herein of the term "functionally equivalent" also encompasses mutations that are "positionally equivalent" or "homologous" to a given mutation, regardless of whether or not the particular function of the mutated amino acid is known. It is possible to identify positionally equivalent or homologous amino acid residues in the amino acid sequences of two or more different proteins on the basis of sequence alignment and/or molecular modelling.

Terminal Deoxynucleotidyl Transferase Engineering

Terminal deoxynucleotidyl transferase (TdT) is one of the first DNA polymerases discovered in mammals. TdT has template-independent activity. TdT's template-independent activity can increase the diversity of the body's antibody repertoire. TdT can catalyze addition of nucleotides onto a single-stranded DNA primer that is at least three nucleotides long in the presence of divalent metal ions. As a member of the X Family of DNA polymerase, TdT is most similar to Pol µ, a template-dependent DNA polymerase. Without being bound by any particular theory, having a sequence similarity of 42% to Pol µ, the factor contributing to the difference between TdT and Pol µ in template dependency has been attributed to the presence of a flexible loop (named Loop1).

Destabilization of Loop1 in TdT has been shown to confer it a template-dependent activity. Switching of Loop1 between TdT and Pol μ can led to partial alteration of DNA substrate preference.

With TdT's unique activity, TdT has been used in the clinical and biotechnology fields. One use of TdT is in the TUNEL assay. In the TUNEL assay, DNA fragments from apoptotic cells are detected by TdT catalyzed incorporation of fluorophore-tagged nucleotides onto the exposed DNA fragments. TdT can also be used in methods to detect low amounts of DNA and RNA for virus detection and diagnosis of genetic diseases.

Being a template-independent DNA polymerase, TdT is an ideal candidate for enzymatic DNA synthesis. Nucleotide conjugated TdT has been used to enable single incorporation on a DNA initiator. TdT's potential for de novo DNA synthesis could also be leveraged to enable data storage in DNA. DNA has the advantages of a prodigiously high information density and low maintenance storage; $10^{15}$-$10^{20}$ bytes of data per gram of DNA for hundreds of years while preserving the quality of data. TdT mediated synthesis of stretches of homopolymers and transitions between these have been used to encode digital data. However, these methods have some inherent disadvantages such as a complicated synthesis process or generation of heterogenous products. An alternative way to generate arbitrary DNA sequence enzymatically would be to use TdT to incorporate reversibly 3' blocked nucleotides, such as 3'-O-blocked nucleotides, including 3'-O-amino blocked nucleotides and 3'-O-azidomethyl blocked nucleotides. No user-friendly DNA synthesis instrument using enzymatic synthesis methods has been launched.

Wild-type (WT) TdT is unable to incorporate bulky 3'-blocked nucleotides due to steric clashes. TdT could be engineered to accept reversibly blocked nucleotides used in sequencing, such as sequencing by synthesis. However, engineering TdT to incorporate reversibly blocked nucleotides is difficult. This is partly because TdT is a mesophilic polymerase with $T_m$ around 40° C. and with marginal stability. Mutations conferring a desired activity can often be destabilizing. Thus, to obtain a more stable initial construct for further engineering, the thermal stability of TdT needs to be improved first.

In addition, enzymatic DNA synthesis may need to overcome the formation of strong DNA secondary structures, such as hairpins, as the lengths of DNA products increase. One potential solution is to elevate the temperature of enzymatic DNA synthesis process. However, the optimum temperature of WT TdT is approximately 37° C., with an unfolding $T_m$ around 40° C. Engineering a thermostable TdT will therefore help minimize the formation of secondary DNA structure during de novo DNA synthesis, by enabling synthesis at higher temperature.

Disclosed herein include TdT variants (also referred to herein as TdT mutants and recombinant TdTs) that were evolved to have improved thermostability. A fluorescence-based TdT activity assay that could be implemented in cell lysates following incubation of increasing temperatures was developed (FIGS. 2 and 3). Secondly, expression and purification protocols were optimized to obtain adequate yields for WT and mutant enzymes. Third, the thermostability of the TdT variants were verified by DSC, DSF, SYPRO Orange thermal shift assay and CD. Finally, kinetic characterization of a thermostabilized TdT mutant, referred to herein as TdT3-2, was performed to demonstrate that gain of thermostability did not occur at the expense of the enzyme's activity.

Recombinant Terminal Deoxynucleotidyl Transferase Sequence

Disclosed herein include embodiments of a recombinant terminal deoxynucleotidyl transferase (TdT). In some embodiments, the recombinant TdT comprises an amino acid sequence that is, or is about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, identical to a bovine or *Bos taurus* TdT (e.g., SEQ ID NO: 12), or a fragment thereof (e.g., SEQ ID NO: 12). In some embodiments, the recombinant TdT comprises an amino acid sequence that is at least, at least about, at most or at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, identical to a bovine or *Bos taurus* TdT (e.g., SEQ ID NO: 12), or a fragment thereof (e.g., SEQ ID NO: 12). For example, the recombinant TdT comprises an amino acid sequence that is at least 85% identical to SEQ ID NO: 1. The recombinant TdT comprises an amino acid sequence that can be at least 90% identical to SEQ ID NO: 1. The recombinant TdT comprises an amino acid sequence that can be at least 95% identical to SEQ ID NO: 1.

In some embodiments, the recombinant TdT comprises an amino acid sequence with a sequence identity above a sequence identity threshold to a fragment of a bovine or *Bos taurus* TdT, such as amino acids 139-520 of *Bos taurus* TdT (e.g., SEQ ID NO: 1). FIG. 1 shows the sequence of amino acids 139-520 of *Bos taurus* TdT. For example, the recombinant terminal deoxynucleotidyl transferase (TdT) can comprise an amino acid sequence that is at least 80% identical to SEQ ID NO: 1. In some embodiments, the recombinant TdT comprises an amino acid sequence with a sequence identity above a sequence identity threshold to a variant of a bovine or *Bos taurus* TdT, or a variant of a bovine or *Bos taurus* TdT fragment (e.g., SEQ ID NO: 11). For example, the recombinant TdT can comprise an amino acid sequence that can be at least 95% identical to SEQ ID NO: 11.

Substitution Mutations

The recombinant TdT can comprise one or more amino acid substitution mutations at one or more positions functionally equivalent to Glu191, Lys193, Glu194, Asp242, Lys287, Phe296, Met299, Thr342, and His421 in the *Bos taurus* TdT (e.g., SEQ ID NO: 12). Each amino acid substitution mutation can be an amino acid substitution mutation to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

Each amino acid substitution mutation can be a substitution mutation to a nonpolar amino acid, a polar amino acid, a positively charged amino acid, a negatively charged amino acid, a hydrophobic amino acid, an aromatic amino acid, an aliphatic amino acid, a small amino acid, a hydrophilic amino acid, or a branched-chain amino acid. A nonpolar amino acid can be, for example, alanine, cysteine, glycine, isoleucine, leucine, methionine, phenylalanine, proline, tryptophan, or valine. A polar amino acid can be, for example, aspartic acid, glutamic acid, arginine, histidine, lysine, asparagine, glutamine, serine, threonine, or tyrosine.

A polar amino acid can be, for example, an acidic polar amino acid, a basic polar amino acid, or a non-acidic non-basic polar amino acid. A basic polar amino acid or positively charged amino acid can be, for example, arginine, histidine, or lysine. An acidic amino acid or negatively charged amino acid can be, for example, aspartic acid or glutamic acid. A non-acidic non-basic amino acid can be, for example, asparagine, glutamine, serine, threonine, or tyrosine. A hydrophobic amino acid can be, for example, isoleucine, leucine, methionine, phenylalanine, tryptophan, tyrosine, or valine. An aromatic amino acid can be, for example, histidine, phenylalanine, tryptophan, or tyrosine. An aliphatic (non-aromatic) amino acid can be, for example, isoleucine, leucine, methionine, or valine. A small amino acid can be, for example, alanine, glycine, proline, or serine. A hydrophilic amino acid can be, for example, arginine, asparagine, aspartic acid, glutamine, glutamic acid, histidine, lysine, serine, or threonine. A branched-chain amino acid can be, for example, isoleucine, leucine, valine.

In some embodiments, the amino acid substitution mutation at the position functionally equivalent to Glu191 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Glu191 can comprise a mutation to a nonpolar amino acid, a hydrophobic amino acid, an aliphatic amino acid, or a branched-chain amino acid. The amino acid substitution mutation at the position functionally equivalent to Glu191 in the *Bos taurus* TdT of SEQ ID NO: 12 can be an amino acid substitution mutation to alanine, arginine, asparagine, aspartic acid, cysteine, glutamine, glycine, histidine, isoleucine, leucine, lysine, methionine, phenylalanine, proline, serine, threonine, tryptophan, tyrosine, or valine. The amino acid substitution mutation at the position functionally equivalent to Glu191 in the *Bos taurus* TdT of SEQ ID NO: 12 can be an amino acid substitution mutation to alanine, glycine, isoleucine, leucine, methionine, or valine. The amino acid substitution mutation at the position functionally equivalent to Glu191 in the *Bos taurus* TdT of SEQ ID NO: 12 can be Glu191Ala, Glu191Arg, Glu191Asn, Glu191Asp, Glu191Cys, Glu191Gln, Glu191Gly, Glu191His, Glu191Ile, Glu191Leu, Glu191Lys, Glu191Met, Glu191Phe, Glu191Pro, Glu191Ser, Glu191Thr, Glu191Trp, Glu191Tyr, or Glu191Val. The amino acid substitution mutation at the position functionally equivalent to Glu191 in the *Bos taurus* TdT of SEQ ID NO: 12 can be Glu191Ala, Glu191Gly, Glu191Ile, Glu191Leu, Glu191Met, or Glu191Val. The amino acid substitution mutation at the position functionally equivalent to Glu191 in the *Bos taurus* TdT of SEQ ID NO: 12 can be Glu191Val. The recombinant TdT can comprise an amino acid sequence with a sequence identity above a sequence identity threshold to SEQ ID NO: 2.

In some embodiments, the amino acid substitution mutation at the position functionally equivalent to Lys193 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Lys193 in the *Bos taurus* TdT of SEQ ID NO: 12 can comprise a mutation to a polar amino acid or a hydrophilic amino acid. The amino acid substitution mutation at the position functionally equivalent to Lys193 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, methionine, phenylalanine, proline, serine, threonine, tryptophan, tyrosine, or valine. The amino acid substitution mutation at the position functionally equivalent to Lys193 in the *Bos taurus* TdT of SEQ ID NO: 12 can be an amino acid substitution mutation to asparagine, glutamine, serine, or threonine. The amino acid substitution mutation at the position functionally equivalent to Lys193 in the *Bos taurus* TdT of SEQ ID NO: 12 can be Lys193Ala, Lys193Arg, Lys193Asn, Lys193Asp, Lys193Cys, Lys193Gln, Lys193Glu, Lys193Gly, Lys193His, Lys193Ile, Lys193Leu, Lys193Met, Lys193Phe, Lys193Pro, Lys193Ser, Lys193Thr, Lys193Trp, Lys193Tyr, or Lys193Val. The amino acid substitution mutation at the position functionally equivalent to Lys193 in the *Bos taurus* TdT of SEQ ID NO: 12 can be Lys193Asn, Lys193Gln, Lys193Ser, or Lys193Thr. The amino acid substitution mutation at the position functionally equivalent to Lys193 in the *Bos taurus* TdT of SEQ ID NO: 12 can be Lys193Asn. The recombinant TdT can comprise an amino acid sequence with a sequence identity above a sequence identity threshold to SEQ ID NO: 3.

In some embodiments, the amino acid substitution mutation at the position functionally equivalent to Glu194 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Glu194 in the *Bos taurus* TdT of SEQ ID NO: 12 can comprise a mutation to a nonpolar amino acid, a hydrophobic amino acid, an aliphatic amino acid, or a branched-chain amino acid. The amino acid substitution mutation at the position functionally equivalent to Glu194 in the *Bos taurus* TdT of SEQ ID NO: 12 can be an amino acid substitution mutation to alanine, arginine, asparagine, aspartic acid, cysteine, glutamine, glycine, histidine, isoleucine, leucine, lysine, methionine, phenylalanine, proline, serine, threonine, tryptophan, tyrosine, or valine. The amino acid substitution mutation at the position functionally equivalent to Glu194 in the *Bos taurus* TdT of SEQ ID NO: 12 can be an amino acid substitution mutation to alanine, glycine, isoleucine, leucine, methionine, or valine. The amino acid substitution mutation at the position functionally equivalent to Glu194 in the *Bos taurus* TdT of SEQ ID NO: 12 can be Glu194Ala, Glu194Arg, Glu194Asn, Glu194Asp, Glu194Cys, Glu194Gln, Glu194Gly, Glu194His, Glu194Ile, Glu194Leu, Glu194Lys, Glu194Met, Glu194Phe, Glu194Pro, Glu194Ser, Glu194Thr, Glu194Trp, Glu194Tyr, or Glu194Val. The amino acid substitution mutation at the position functionally equivalent to Glu194 in the *Bos taurus* TdT of SEQ ID NO: 12 can be Glu194Ala, Glu194Gly, Glu194Ile, Glu194Leu, Glu194Met, or Glu194Val. The amino acid substitution mutation at the position functionally equivalent to Glu194 in the *Bos taurus* TdT of SEQ ID NO: 12 can be Glu194Gly. The recombinant TdT can comprise an amino acid sequence with a sequence identity above a sequence identity threshold to SEQ ID NO: 4.

In some embodiments, the amino acid substitution mutation at the position functionally equivalent to Asp242 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Asp242 in the *Bos taurus* TdT of SEQ ID NO: 12 can comprise a mutation to a polar amino acid or an aromatic amino acid. The amino acid substitution mutation at the position functionally equivalent to Asp242 in the *Bos taurus* TdT of SEQ ID NO: 12 can be an amino acid substitution mutation to alanine, arginine, asparagine, cysteine, glutamine, glutamic acid, glycine, histidine, isoleucine, leucine, lysine, methionine, phenylalanine, proline, serine, threonine, tryptophan, tyrosine, or valine. The amino acid substitution mutation at the position functionally equivalent to Asp242 in the *Bos taurus* TdT of SEQ ID NO: 12 can be an amino acid substitution mutation amino acid substitution mutation at the position functionally equivalent to Asp242 in the *Bos taurus* TdT of SEQ ID NO: 12 can be Asp242Ala, Asp242Arg, Asp242Asn, Asp242Cys, Asp242Gln, Asp242Glu, Asp242Gly, Asp242His, Asp242Ile, Asp242Leu, Asp242Lys, Asp242Met, Asp242Phe, Asp242Pro, Asp242Ser, Asp242Thr, Asp242Trp, Asp242Tyr, or Asp242Val. The amino acid substitution mutation at the position functionally equivalent to Asp242 in the *Bos taurus* TdT of SEQ ID NO: 12 can be Asp242Asn, Asp242Gln, Asp242Phe, Asp242Ser, Asp242Thr, Asp242Trp, or Asp242Tyr. The amino acid substitution mutation at the position functionally equivalent to Asp242 in the *Bos taurus* TdT of SEQ ID NO: 12 can be Asp242Tyr. The recombinant TdT can comprise an amino acid sequence with a sequence identity above a sequence identity threshold to SEQ ID NO: 5.

In some embodiments, the amino acid substitution mutation at the position functionally equivalent to Lys287 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Lys287 in the *Bos taurus* TdT of SEQ ID NO: 12 can comprise a mutation to a polar amino acid, a negatively charged amino acid or a hydrophilic amino acid. The amino acid substitution mutation at the position functionally equivalent to Lys287 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, methionine, phenylalanine, proline, serine, threonine, tryptophan, tyrosine, or valine. The amino acid substitution mutation at the position functionally equivalent to Lys287 in the *Bos taurus* TdT of SEQ ID NO: 12 can be an amino acid substitution mutation to aspartic acid or glutamic acid. The amino acid substitution mutation at the position functionally equivalent to Lys287 in the *Bos taurus* TdT of SEQ ID NO: 12 can be Lys287Ala, Lys287Arg, Lys287Asn, Lys287Asp, Lys287Cys, Lys287Gln, Lys287Glu, Lys287Gly, Lys287His, Lys287Ile, Lys287Leu, Lys287Met, Lys287Phe, Lys287Pro, Lys287Ser, Lys287Thr, Lys287Trp, Lys287Tyr, or Lys287Val. The amino acid substitution mutation at the position functionally equivalent to Lys287 in the *Bos taurus* TdT of SEQ ID NO: 12 can be Lys287Asp or Lys287Glu. The amino acid substitution mutation at the position functionally equivalent to Lys287 in the *Bos taurus* TdT of SEQ ID NO: 12 can be Lys287Glu. The recombinant TdT can comprise an amino acid sequence with a sequence identity above a sequence identity threshold to SEQ ID NO: 6.

In some embodiments, the amino acid substitution mutation at the position functionally equivalent to Phe296 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Phe296 in the *Bos taurus* TdT of SEQ ID NO: 12 can comprise a mutation to a nonpolar amino acid, a hydrophobic amino acid, an aliphatic amino acid, or a branched-chain amino acid. The amino acid substitution mutation at the position functionally equivalent to Phe296 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, lysine, methionine, proline, serine, threonine, tryptophan, tyrosine, or valine. The amino acid substitution mutation at the position functionally equivalent to Phe296 in the *Bos taurus* TdT of SEQ ID NO: 12 can be an amino acid substitution mutation to alanine, glycine, isoleucine, leucine, methionine, or valine. The amino acid substitution mutation at the position functionally equivalent to Phe296 in the *Bos taurus* TdT of SEQ ID NO: 12 can be Phe296Ala, Phe296Arg, Phe296Asn, Phe296Asp, Phe296Cys, Phe296Gln, Phe296Glu, Phe296Gly, Phe296His, Phe296Ile, Phe296Leu, Phe296Lys, Phe296Met, Phe296Pro, Phe296Ser, Phe296Thr, Phe296Trp, Phe296Tyr, or Phe296Val. The amino acid substitution mutation at the position functionally equivalent to Phe296 in the *Bos taurus* TdT of SEQ ID NO: 12 can be Phe296Ala, Phe296Gly, Phe296Ile, Phe296Leu, Phe296Met, or Phe296Val. The amino acid substitution mutation at the position functionally equivalent to Phe296 in the *Bos taurus* TdT of SEQ ID NO: 12 can be Phe296Leu. The recombinant TdT can comprise an amino acid sequence with a sequence identity above a sequence identity threshold to SEQ ID NO: 7.

In some embodiments, the amino acid substitution mutation at the position functionally equivalent to Met299 in the *Bos taurus* TdT of SEQ ID NO: 12 comprises a mutation to a polar amino acid, a positively charged amino acid, or a hydrophilic amino acid. a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Met299 in the *Bos taurus* TdT of SEQ ID NO: 12 can comprise a mutation to a polar amino acid, a positively charged amino acid, or a hydrophilic amino acid. The amino acid substitution mutation at the position functionally equivalent to Met299 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, lysine, phenylalanine, proline, serine, threonine, tryptophan, tyrosine, or valine. The amino acid substitution mutation at the position functionally equivalent to Met299 in the *Bos taurus* TdT of SEQ ID NO: 12 can be an amino acid substitution mutation to arginine, arginine, histidine, or lysine. The amino acid substitution mutation at the position functionally equivalent to Met299 in the *Bos taurus* TdT of SEQ ID NO: 12 can be Met299Ala, Met299Arg, Met299Asn, Met299Asp, Met299Cys, Met299Gln, Met299Glu, Met299Gly, Met299His, Met299Ile, Met299Leu, Met299Lys, Met299Phe, Met299Pro, Met299Ser, Met299Thr, Met299Trp, Met299Tyr, or Met299Val. The amino acid substitution mutation at the position functionally equivalent to Met299 in the *Bos taurus* TdT of SEQ ID NO: 12 can be Met299Arg, Met299His, or Met299Lys. The amino acid substitution mutation at the position functionally equivalent to Met299 in the *Bos taurus* TdT of SEQ ID NO: 12 can be Met299Lys. The recombinant TdT can comprise an amino acid sequence with a sequence identity above a sequence identity threshold to SEQ ID NO: 8.

In some embodiments, the amino acid substitution mutation at the position functionally equivalent to Thr342 in the *Bos taurus* TdT of SEQ ID NO: 12 comprises a mutation to a polar amino acid, an aliphatic amino acid, or a hydrophilic amino acid. a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Thr342 in the *Bos taurus* TdT of SEQ ID NO: 12 can comprise a mutation to a polar amino acid, an aliphatic amino acid, or a hydrophilic amino acid. The amino acid substitution mutation at the position functionally equivalent to Thr342 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, lysine, methionine, phenylalanine, proline, serine, tryptophan, tyrosine, or valine. The amino acid substitution mutation at the position functionally equivalent to Thr342 in the *Bos taurus* TdT of SEQ ID NO: 12 can be an amino acid substitution mutation to asparagine, cystine, glutamine, proline, or serine. The amino acid substitution mutation at the position functionally equivalent to Thr342 in the *Bos taurus* TdT of SEQ ID NO: 12 can be Thr342Ala, Thr342Arg, Thr342Asn, Thr342Asp, Thr342Cys, Thr342Gln, Thr342Glu, Thr342Gly, Thr342His, Thr342Ile, Thr342Leu, Thr342Lys, Thr342Met, Thr342Phe, Thr342Pro, Thr342Ser, Thr342Trp, Thr342Tyr, or Thr342Val. The amino acid substitution mutation at the position functionally equivalent to Thr342 in the *Bos taurus* TdT of SEQ ID NO: 12 can be Thr342Asn, Thr342Cys, Thr342Gln, Thr342Pro, or Thr342Ser. The amino acid substitution mutation at the position functionally equivalent to Thr342 in the *Bos taurus* TdT of SEQ ID NO: 12 can be Thr342Ser. The recombinant TdT can comprise an amino acid sequence with a sequence identity above a sequence identity threshold to SEQ ID NO: 9.

In some embodiments, the amino acid substitution mutation at the position functionally equivalent to His421 in the *Bos taurus* TdT of SEQ ID NO: 12 comprises a mutation to a polar amino acid, an aliphatic amino acid, or a hydrophilic amino acid. a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to His421 in the *Bos taurus* TdT of SEQ ID NO: 12 can comprise a mutation to a polar amino acid, an aliphatic amino acid, or a hydrophilic amino acid. The amino acid substitution mutation at the position functionally equivalent to His421 in the *Bos taurus* TdT of SEQ ID NO: 12 can be an amino acid substitution mutation to alanine, arginine, asparagine, aspartic acid, cysteine, glutamine, glutamic acid, glycine, isoleucine, leucine, lysine, methionine, phenylalanine, proline, serine, threonine, tryptophan, tyrosine, or valine. The amino acid substitution mutation at the position functionally equivalent to His421 in the *Bos taurus* TdT of SEQ ID NO: 12 can be an amino acid substitution mutation to asparagine, cystine, glutamine, proline, serine, or threonine. The amino acid substitution mutation at the position functionally equivalent to His421 in the *Bos taurus* TdT of SEQ ID NO: 12 can be His421Ala, His421Arg, His421Asn, His421Asp, His421Cys, His421Gln, His421Glu, His421Gly, His421Ile, His421Leu, His421Lys, His421Met, His421Phe, His421Pro, His421Ser, His421Thr, His421Trp, His421Tyr, or His421Val. The amino acid substitution mutation at the position functionally equivalent to His421 in the *Bos taurus* TdT of SEQ ID NO: 12 can be His421Asn, His421Cys, His421Gln, His421Pro, His421Ser, or His421Thr. The amino acid substitution mutation at the position functionally equivalent to His421 in the *Bos taurus* TdT of SEQ ID NO: 12 can be His421Pro. The recombinant TdT can comprise an amino acid sequence with a sequence identity above a sequence identity threshold to SEQ ID NO: 10.

In some embodiments, the recombinant TdT comprises two or more amino acid substitution mutations at two or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise three or more amino acid substitution mutations at three or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise four or more amino acid substitution mutations at four or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise five or more amino acid substitution mutations at five or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise six or more amino acid substitution mutations at six or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise seven or more amino acid substitution mutations at seven or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise eight or more amino acid substitution mutations at eight or more positions functionally equivalent to Glu191, Lys193, Glu194, Asp242, Lys287, Phe296, Met299, Thr342, and His421 in the *Bos taurus* TdT of SEQ ID NO: 12.

In some embodiments, the two or more amino acid substitution mutations at the two or more positions functionally equivalent to Glu191, Lys193, Glu194, Asp242, Lys287, Phe296, Met299, Thr342, and His421 in the *Bos taurus* TdT of SEQ ID NO: 12 comprise two or more of Glu191Val, Lys193Asn, Glu194Gly, Asp242Tyr, Lys287Glu, Phe296Leu, Met299Lys, Thr342Ser, and His421Pro, respectively. The three or more amino acid substitution mutations at the three or more positions functionally equivalent to Glu191, Lys193, Glu194, Asp242, Lys287, Phe296, Met299, Thr342, and His421 in the *Bos taurus* TdT of SEQ ID NO: 12 can comprise three or more of Glu191Val, Lys193Asn, Glu194Gly, Asp242Tyr, Lys287Glu, Phe296Leu, Met299Lys, Thr342Ser, and His421Pro, respectively. The four or more amino acid substitution mutations at the four or more positions functionally equivalent to Glu191, Lys193, Glu194, Asp242, Lys287, Phe296, Met299, Thr342, and His421 in the *Bos taurus* TdT of SEQ ID NO: 12 can comprise four or more of Glu191Val, Lys193Asn, Glu194Gly, Asp242Tyr, Lys287Glu, Phe296Leu, Met299Lys, Thr342Ser, and His421Pro, respectively. The five or more amino acid substitution mutations at the five or more positions functionally equivalent to Glu191, Lys193, Glu194, Asp242, Lys287, Phe296, Met299, Thr342, and His421 in the *Bos taurus* TdT of SEQ ID NO: 12 can comprise five or more of Glu191Val, Lys193Asn, Glu194Gly, Asp242Tyr, Lys287Glu, Phe296Leu, Met299Lys, Thr342Ser, and His421Pro, respectively. The six or more amino acid substitution mutations at the six or more positions functionally equivalent to Glu191, Lys193, Glu194, Asp242, Lys287, Phe296, Met299, Thr342, and His421 in the *Bos taurus* TdT of SEQ ID NO: 12 can comprise six or more of Glu191Val, Lys193Asn, Glu194Gly, Asp242Tyr, Lys287Glu, Phe296Leu, Met299Lys, Thr342Ser, and His421Pro, respectively. The seven or more amino acid substitution mutations at the seven or more positions functionally equivalent to Glu191, Lys193, Glu194, Asp242, Lys287, Phe296, Met299, Thr342, and His421 in the *Bos taurus* TdT of SEQ ID NO: 12 can comprise seven or more of Glu191Val, Lys193Asn, Glu194Gly, Asp242Tyr, Lys287Glu, Phe296Leu, Met299Lys, Thr342Ser, and His421Pro, respectively. The eight or more amino acid substitution mutations at the eight or more positions functionally equivalent to Glu191, Lys193, Glu194, Asp242, Lys287, Phe296, Met299, Thr342, and His421 in the *Bos taurus* TdT of SEQ ID NO: 12 can comprise Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises eight amino acid substitution mutations at eight positions functionally equivalent to Lys193, Glu194, Asp242, Lys287, Phe296, Met299, Thr342, and His421 in the *Bos taurus* TdT of SEQ ID NO: 12. The eight amino acid substitution mutations at the eight positions functionally equivalent to Lys193, Glu194, Asp242, Lys287, Phe296, Met299, Thr342, and His421 in the *Bos taurus* TdT of SEQ ID NO: 12 can be Lys193Asn, Glu194Gly, Asp242Tyr, Lys287Glu, Phe296Leu, Met299Lys, Thr342Ser, and His421Pro, respectively. In some embodiments, the recombinant TdT comprises nine amino acid substitution mutations at positions functionally equivalent to Glu191, Lys193, Glu194, Asp242, Lys287, Phe296, Met299, Thr342, and His421 in the *Bos taurus* TdT of SEQ ID NO: 12. The nine amino acid substitution mutations at the positions functionally equivalent to Glu191, Lys193, Glu194, Asp242, Lys287, Phe296, Met299, Thr342, and His421 in the *Bos taurus* TdT of SEQ ID NO: 12 can be Glu191Val, Lys193Asn, Glu194Gly, Asp242Tyr, Lys287Glu, Phe296Leu, Met299Lys, Thr342Ser, and His421Pro, respectively.

Thermal Stability

The recombinant TdT can be thermally stable. The recombinant TdT can be stable at different temperatures in different embodiments. In some embodiments, the recombinant TdT can be stable at a temperature of, or of about, 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or higher. For example, the recombinant TdT can be stable at a temperature of 47° C. or higher. The recombinant TdT can be stable at a temperature of 50° C. or higher. The recombinant TdT can be stable at a temperature of 55° C. or higher. The recombinant TdT can be stable at a temperature of 58° C. or higher. The recombinant TdT can be stable at a temperature of at least, of at least about, of at most, or of at most about, 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or a number or a range between any two of these values.

Activity

The terminal deoxynucleotidyl transferase activity of the recombinant TdT can be higher than, or lower than, a bovine or *Bos taurus* TdT, or a fragment thereof. In some embodiments, the terminal deoxynucleotidyl transferase activity of the recombinant TdT is, or is about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, or more, of the terminal deoxynucleotidyl transferase activity of the *Bos taurus* TdT of SEQ ID NO: 12, or of the recombinant TdT of SEQ ID NO: 14, at a same test temperature. In some embodiments, the terminal deoxynucleotidyl transferase activity of the recombinant TdT is at least, is at least about, is at most, or is at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, or a number or a range between any two of these values, of the terminal deoxynucleotidyl transferase activity of the *Bos taurus* TdT of SEQ ID NO: 12, or the recombinant TdT of SEQ ID NO: 14, at a same test temperature. For example, the terminal deoxynucleotidyl transferase activity of the recombinant TdT can be, or be at least 80%, 85%, 90%, 95%, 100%, 105%, 110%, 115%, or 120%, of the terminal deoxynucleotidyl transferase activity of the *Bos taurus* TdT of SEQ ID NO: 12, or the recombinant TdT of SEQ ID NO: 14, at a same test temperature.

The test temperature can be different in different embodiments. In some embodiments, the test temperature can be, or be about, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or higher. For example, the test temperature can be 37° C., 47° C., 50° C., 55° C., or 58° C. In some embodiments, the test temperature can be at least, be at least about, be at most, or be at most about, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or a number or a range between any two of these values.

Additional Components

In some embodiments, the recombinant TdT comprises a tag for purification, such as a His-tag or a glutathione S-transferase. The tag for purification can be on the N-terminal of the recombinant TdT, on the C-terminal of the recombinant TdT, or internal to the recombinant TdT. The recombinant TdT can comprise a protease cleavage sequence, such as LeuValProArg/GlySer (a thrombin cleavage site) or LeuGluValLeuPheGln/GlyPro (a PreScission Protease cleavage site) between the tag for purification and another component (e.g., a *Bos taurus* TdT fragment) or the rest of the recombinant TdT.

In some embodiments, the recombinant TdT comprises a small ubiquitin-like modifier (SUMO) protein, or a fragment thereof. The sequence of the SUMO protein, or a fragment thereof, in the recombinant TdT can be different in different embodiments. In some embodiments, the SUMO protein, or a fragment thereof, in the recombinant TdT comprises an amino acid sequence that is, or about, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, identical to a SUMO protein (e.g., suppressor of mif two 3, SMT3, in yeast), or a fragment thereof (e.g., a SUMO fragment comprising an amino sequence of SEQ ID NO: 13). For example, the SUMO fragment in the recombinant TdT can comprise an amino acid sequence that is at least 80% identical to SEQ ID NO: 13. In some embodiments, the SUMO protein, or a fragment thereof, in the recombinant TdT comprises an amino acid sequence that is, is at least about, is at most, or is at most about, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, identical to a SUMO protein (e.g., suppressor of mif two 3, SMT3, in yeast), or a fragment thereof (e.g., a SUMO fragment comprising an amino acid sequence of SEQ ID NO: 13).

The location of the SUMO fragment in the recombinant TdT can be different in different embodiments. In some embodiments, the recombinant TdT comprises the SUMO fragment on the N-terminus of the recombinant TdT. In some embodiments, the recombinant TdT comprises the SUMO fragment on the C-terminus of the recombinant TdT.

The recombinant TdT can comprise an amino acid sequence with a sequence identity of, or of about, a sequence identity threshold to a recombinant TdT comprising a SUMO fragment (e.g., a recombinant TdT with a SUMO fragment comprising an amino acid sequence of SEQ ID NO: 14, or SEQ ID NO: 15). The recombinant TdT can comprise an amino acid sequence with a sequence identity above, above about, below, or below about, a sequence identity threshold to a recombinant TdT comprising a SUMO fragment (e.g., SEQ ID NO: 14, or SEQ ID NO: 15). The recombinant TdT can comprise an amino acid sequence with a sequence identity of at least, at least about, at most, or at most about, a sequence identity threshold to a recombinant TdT comprising a SUMO fragment (e.g., SEQ ID NO: 14, or SEQ ID NO: 15). The sequence identity threshold can be different in different embodiments. In some embodiments, the sequence identity threshold is 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. For example, the recombinant TdT can comprise an amino acid sequence that is at least 80% identical to SEQ ID NO: 14. As another example, the recombinant TdT can comprise an amino acid sequence that is at least 80% identical to SEQ ID NO: 15.

Mutating Terminal Deoxynucleotidyl Transferase

Various types of mutagenesis can be used in the present disclosure, for example, to modify TdTs to produce variants, for example, in accordance with TdT models and model predictions, or using random or semi-random mutational approaches. In general, any available mutagenesis procedure can be used for making TdT mutants. Such mutagenesis procedures can include selection of mutant nucleic acids and polypeptides for one or more activity of interest (for example, enhanced seeding and/or amplification on a solid support). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting TdT for mutation can be any of those noted herein.

Mutagenesis can be guided by known information from a naturally occurring TdT molecule, or of a known altered or mutated TdT, for example, sequence, sequence comparisons, physical properties, crystal structure and/or the like as discussed herein. However, in another class of embodiments, modification can be essentially random (for example, as in classical or "family" DNA shuffling).

Making and Isolating Recombinant Terminal Deoxynucleotidyl Transferase

Generally, polynucleotides or nucleic acids encoding a recombinant TdT as presented herein can be made by cloning, recombination, in vitro synthesis, in vitro amplification and/or other available methods. A variety of recombinant methods can be used for expressing an expression vector that encodes a recombinant TdT as presented herein. Methods for making recombinant nucleic acids, expression and isolation of expressed products are known. A number of exemplary mutations and combinations of mutations, as well as strategies for design of desirable mutations, are described herein.

In addition, kits are commercially available for the purification of plasmids or other relevant nucleic acids from cells. Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, polynucleotides or nucleic acids presented herein can be "codon optimized, meaning that the polynucleotides or nucleic acids are synthesized to include codons that are preferred by the particular translation system being employed to express the recombinant TdT. For example, when it is desirable to express the recombinant TdT in a bacterial cell (or even a particular strain of bacteria), the polynucleotide or nucleic acid can be synthesized to include codons most frequently found in the genome of that bacterial cell, for efficient expression of the recombinant TdT. A similar strategy can be employed when it is desirable to express the recombinant TdT in a eukaryotic cell, e.g., the nucleic acid can include codons preferred by that eukaryotic cell.

A variety of protein isolation and detection methods are known and can be used to isolate recombinant TdTs, e.g., from recombinant cultures of cells expressing the recombinant TdTs presented herein. A variety of protein isolation and detection methods are known. A recombinant TdT can be isolated and detected as disclosed herein.

Nucleic Acids Encoding Recombinant Terminal Deoxynucleotidyl Transferase

Disclosed herein include embodiments of a polynucleotide encoding any recombinant terminal deoxynucleotidyl transferase (TdT) of the present disclosure. Disclosed herein include embodiments of an expression vector comprising a polynucleotide encoding any recombinant terminal deoxynucleotidyl transferase (TdT) of the present disclosure.

Further presented herein are nucleic acid molecules (e.g., polynucleotides) encoding the TdT presented herein. For any given altered TdT that is a mutant version of a TdT of a species for which the amino acid sequence and preferably also the wild type nucleotide sequence encoding the TdT is known, it is possible to obtain a nucleotide sequence encoding the mutant according to the basic principles of molecular biology. For example, given that the wild type nucleotide sequence encoding TdT is known, it is possible to deduce a nucleotide sequence encoding any given mutant version of TdT having one or more amino acid substitutions using the standard genetic code. Similarly, nucleotide sequences can readily be derived for mutant versions of TdT of other species. Nucleic acid molecules having the required nucleotide sequence may then be constructed using standard molecular biology techniques.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the TdT encoded therefrom in a suitable host. Incorporation of cloned DNA into a suitable expression vector for subsequent transformation of said cell and subsequent selection of the transformed cells are known.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein.

The nucleic acid molecule may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the TdT by higher eukaryotes may be optimized by including an enhancer sequence in the vector. Enhancers are cis-acting elements of DNA that act on a promoter to increase the level of transcription. Vectors will also generally include origins of replication in addition to the selectable markers.

Cells

Disclosed herein include embodiments of a host cell comprising any recombinant terminal deoxynucleotidyl transferase of the present disclosure. Disclosed herein include embodiments of a host cell comprising a polynucleotide encoding any recombinant terminal deoxynucleotidyl transferase (TdT) of the present disclosure. Disclosed herein include embodiments of a host cell comprising an expression vector comprising a polynucleotide encoding any recombinant terminal deoxynucleotidyl transferase of the present disclosure.

Kits

Disclosed herein include kits. In some embodiments, a kit comprises: a recombinant terminal deoxynucleotidyl transferase (TdT) of the present disclosure; and instructions for using the recombinant terminal deoxynucleotidyl transferase. In some embodiments, a kit comprises: a polynucleotide encoding a recombinant terminal deoxynucleotidyl transferase of the present disclosure; and instructions for using the polynucleotide and/or the recombinant terminal deoxynucleotidyl transferase. In some embodiments, a kit comprises: an expression vector comprising a polynucleotide encoding a recombinant terminal deoxynucleotidyl transferase of the present disclosure; and instructions for using the expression vector, the polynucleotide, and/or the recombinant terminal deoxynucleotidyl transferase. In some embodiments, a kit comprises: a host cell comprising a recombinant terminal deoxynucleotidyl transferase of the present disclosure, a polynucleotide encoding the recombinant terminal deoxynucleotidyl transferase, an expression vector comprising the polynucleotide encoding the recombinant terminal deoxynucleotidyl transferase, or a combination thereof; and instructions for using the recombinant terminal deoxynucleotidyl transferase, the polynucleotide, the expression vector, the host cell, or a combination thereof.

EXAMPLE

Some aspects of the embodiments discussed above are disclosed in further detail in the following example, which is not in any way intended to limit the scope of the present disclosure.

Example 1

Evolving a Thermostable Terminal Deoxynucleotidyl Transferase

Terminal deoxynucleotidyl transferase (TdT) catalyzes template free incorporation of arbitrary nucleotides onto single-stranded DNA. Due to this unique feature, TdT is widely used in biotechnology and clinical applications. One possible use is the synthesis of long de novo DNA molecules by TdT-mediated iterative incorporation of a 3' reversibly blocked nucleotide, followed by deblocking. However, wild-type (WT) TdT is not optimized for the incorporation of 3' modified nucleotides, and TdT engineering is hampered by the fact that TdT is marginally stable and only present in mesophilic organisms. This example describes evolving a thermostable TdT variant to serve as backbone for subsequent evolution to enable efficient incorporation of 3'-modified nucleotides. A thermostable variant would be a good starting point for such an effort, as evolution to incorporate bulky modified nucleotides generally results in lowered stability of TdT. In addition, a thermostable TdT would also be useful in cases where DNA secondary structures inhibit WT activity, as higher temperature could be used to melt dsDNA. An assay was developed to identify thermostable TdT variants. After screening about 10,000 TdT mutants, a mutant named TdT3-2 that was 10° C. more thermostable than SUMO-TdT, while preserving the TdT catalytic properties, was found.

Materials and Methods

Establishing a Plate-Based FRET Assay

Oligonucleotide 2bA FAM (5'-CGC TTG CAC AGG TGC GTT/iFluorT/CA-3', SEQ ID NO: 16), consist a fluorescein (FAM) dye on a T base two bases from 3'-OH was purchased from Integrated DNA Technologies (IDT, Coralville, Iowa, USA). Cy5-dCTP (NU-809-CY5) was purchased from JenaBioscience (Germany). Terminal transferase (NEB TdT) was purchased from New England Biolabs (NEB, Ipswich, Massachusatts, USA).

The gain of signal using FAM and Cy5 Förster or fluorescence resonance energy transfer (FRET) pairs was tested using 200 nM 2bA FAM oligo, 600 nM Cy5-dCTP, 20 U of NEB TdT in 1X TdT buffer (200 mM potassium acetate, 25 mM Tris, 0.01% (v/v) Triton® X-100 (2-[4-(2,4,4-trimethylpentan-2-yl)phenoxy]ethanol), 1 mM cobalt chloride, pH 7.2), with a final volume of 50 μL. A negative control without NEB TdT was included. The reaction samples were incubated at room temperature for 1 min for incorporation of Cy5-dCTP onto 2bA FAM oligo by TdT. The reaction was quenched by heating at 80° C. for 5 min. The samples were transferred to a black bottom 384-well plate (Greiner, Austria) for signal detection on Biotek Synergy H1 Hybrid Multi-mode reader (Winooski, VT USA). An excitation of 450 nm was set, and emission wavelengths were scanned from 480 nm to 700 nm.

SUMO-TdT in this disclosure refers to a recombinant TdT that contains amino acids 139-520 of a bovine (Bos taurus) TdT and an N-terminal SUMO-tag which improves solubility and expression. Table 1 shows the sequence of a SUMO-TdT. FIG. 1 shows a non-limiting exemplary sequence alignment of SUMO-TdT with amino acids 139-520 of Bos taurus TdT. pET28b plasmid carrying SUMO-TdT was transformed into E. coli BL21 (DE3) (NEB, USA) following the manufacturer's protocol and induced with 1 mM isopropyl-β-D-thiogalactopyranoside (IPTG) (Sigma, St. Louis, MO, USA) at 15° C. overnight in a shaker at 250 rpm. The induced cell lysate expressing TdT was aliquoted into four portions (undiluted, diluted 10 times, diluted 100 times and diluted 1000 times with 1×TdT buffer) and lysed using Q700 horn sonicator (Qsonica, Newtown, CT, USA). Oligo FAM20 (5'-/56-FAM/CGCTTGCACAGGTGCGTTCG-3', SEQ ID NO: 17) (IDT, USA) and Deoxycytidine triphosphate (dCTP (Invitrogen, Waltham, MA, USA)) was added to the lysed and diluted cell lysate, bringing final cell lysate dilution to 5 times, 50 times, 500 times and 5000 times. Samples were incubated at 37° C. for 1 min for incorporation of dCTP onto FAM20 by TdT. The reaction was quenched by heating the reaction solution at 80° C. for 5 min and addition of equal volume of 2×TBE-Urea sample buffer (Invitrogen, USA).

Quenched reaction samples were analyzed on 20% polyacrylamide gel. S2 glass plates (Apogee, Baltimore, MD, USA) were washed with Alconox and water before wiping with ethanol, water, 5% dichlorodimethylsilane (DCDMS) (Sigma, USA) and water. The plates were assembled with 0.8 mm spacer (Apogee, USA), gel sealing tapes (Apogee, USA) and binder clips. 0.2% (v/v) ammonium persulfate (APS) (Sigma, USA) and 0.2% (v/v) tetramethylethylenediamine (TEMED) (Bio-Rad, Hercules, CA, USA) solution in 1 mL water was prepared and poured into assembled glass plates. A 20% acrylamide solution (90 mL) was prepared by mixing 45 mL of 40% acrylamide/bis 19:1 solution (Bio-Rad, USA) and 45 mL water before adding 225 µL of 10% APS and 22.5 µL TEMED. The 20% acrylamide solution was loaded into glass plates with 50 mL syringe. A 32-well plastic comb of 0.8 mm thick (Apogee, USA) was inserted into the gel and allowed to polymerize for 1 h 30 min. The comb and gel tape were removed carefully before mounting the gel plates on a S2 Sequencing Gel Electrophoresis Apparatus (Biometra-Analytik Jena, Germany). The running buffer, 1× Tris/Borate (TBE) buffer, was poured at the top and bottom reservoir to about 3 cm above gel. Any gel fragments in the wells were removed. Pre-electrophoresis were carried out at 1700 V for 15 min to obtain a gel surface temperature of about 50° C. before loading the samples. A 15 µL of each quenched reaction sample were loaded into each well and run at 1700 V for 1 h 30 min. The gel was imaged on Bio-Rad Gel Doc XR+(USA) using Sybr Green exposure.

Figure 6:
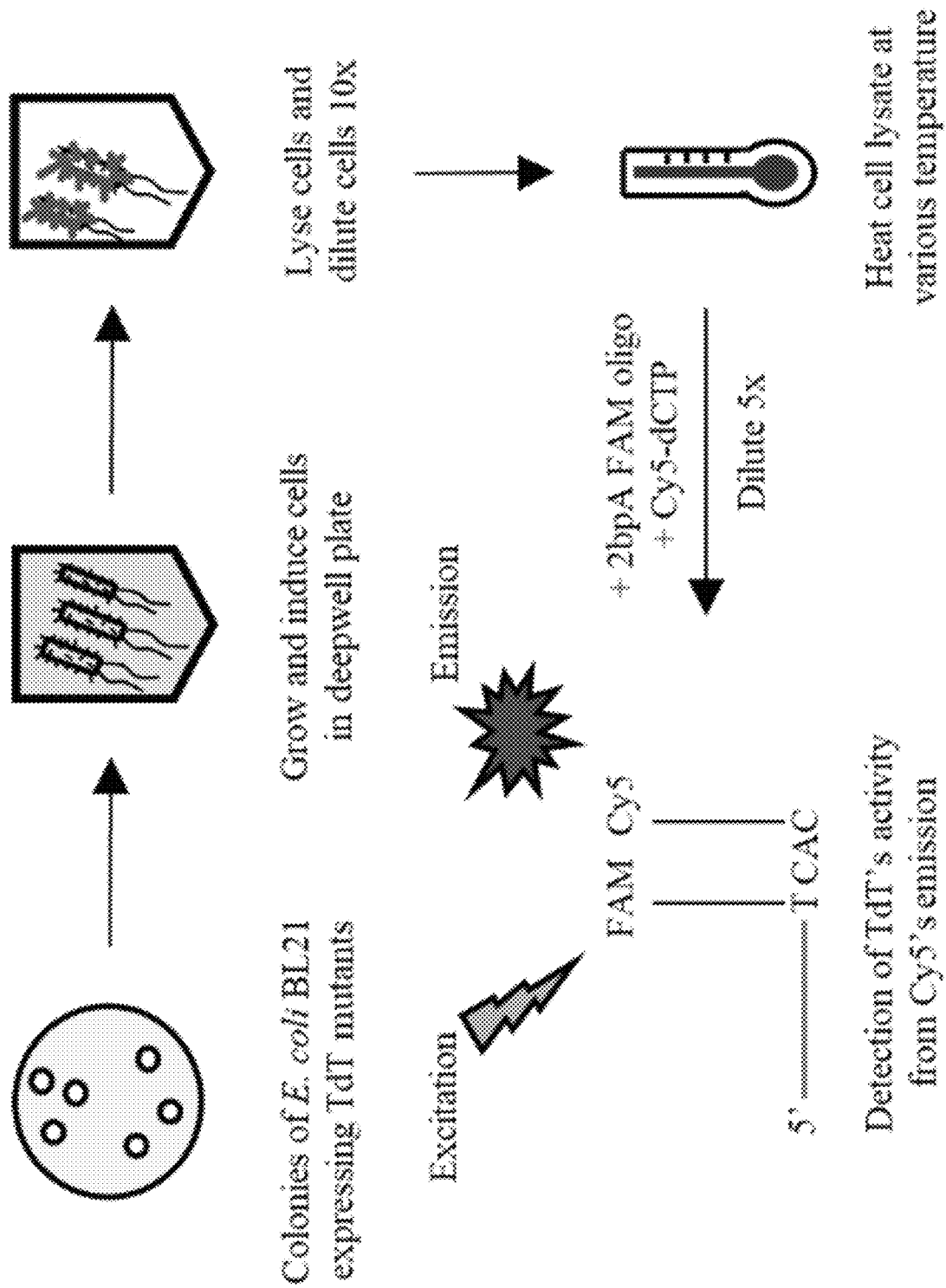
FIG. 6 is a schematic illustration showing a non-limiting exemplary methodology for TdT thermostability screen. Two serial dilution steps (10× and 5×) result in a net 50× diluted lysate.

A workflow of the plate-based FRET assay was established as shown in FIG. 6. To investigate the robustness of this assay, a blind test was carried out. *E. coli* BL21 (DE3) (New England Biolabs, USA) colonies expressing empty pET28b vector and SUMO-TdT were inoculated into 200 µL Luria Broth (LB) supplemented with 50 µg/mL kanamycin in each well of a 96-deepwell plate (Eppendorf, Germany), grown at 37° C. overnight, 250 rpm. Grown cultures were sub-cultured 100-fold into fresh 495 µL LB supplemented with 50 µg/ml kanamycin in new 96-deepwell plate and incubated at 24° C. for 4 h before inducing with 0.5 mM isopropyl β-d-1-thiogalactopyranoside (IPTG) at 24° C. for at least 16 h, 800 rpm. Induced cell lysate was diluted with 1×TdT buffer 10-fold in 0.2 mL PCR tube plate (AITbiotech, Singapore). The cell lysate was lysed using a horn sonicator with the following parameters: Amp 90, 3 min process time, 5 s pulse-on and 15 s pulse-off. A master mix of 24 µL containing 200 nM 2bA FAM oligo, 600 nM Cy5-dCTP and 1×TdT buffer were added into each well in a black 384-well plate. A suspension of lysed cells (6 µL) were added into each respective well. FRET signal detection was performed on PerkinElmer (Waltham, MA, USA) EnSpire Multimode plate reader for 30 min with excitation at 450 nm and emission detection at 670 nm.

Generation of TdT Mutant Library

SUMO-TdT plasmid was used as the backbone template for mutagenesis. Error-prone polymerase mutazyme II (Agilent Technologies, USA) was used to generate a library of an average of 2 to 5 mutations per gene length using gene primer 1 (5'-AAAAAACACCTGCGGCCTGGTGCCG-CGCGGCAGCGCTAGCATG-3', SEQ ID NO: 18) and gene primer 2 (5'-AAAAAACACCTGCGG-GATCCGGTACCGCGGCCGCCTA-3', SEQ ID NO: 19). The mutagenized pool was ligated into pET28b vector and transformed into *E. coli* 10-beta competent cells (New England Biolabs, USA) for amplification of the plasmids. Cells were recovered, scaled up in 50 mL LB supplemented with 50 µg/mL kanamycin and grown at 37° C. till $OD_{600\,nm}$~0.5 was achieved. Cell culture was harvested, and plasmids were extracted using Miniprep kit (Qiagen, Germany). The same process of mutagenesis was performed using TdT1-1 as parent template for second round of screen.

The mutant library for third round of screen used TdT1-1 and TdT1-3 as parent template for incorporation of different combination of mutations identified from TdT2-1, TdT2-2, TdT2-3 and TdT2-4. Primers used to introduce the mutations to parent templates:

Primer A:
(SEQ ID NO: 20)
5'-AATTCTGTGTTTAAWGRAAATGAAGTCTCTTATGTG-3'

Primer B:
(SEQ ID NO: 21)
5'-AGATCTCTGAGTRAAATAATGTCAGACAAAACCCTGAA-3'

Primer C:
(SEQ ID NO: 22)
5'-AGACAAAACCCTGAAATTMACAAAAAWGCAGAAAGCAGGAT-3'

Primer D:
(SEQ ID NO: 23)
5'-TTTGTCACCATGWCAGGAGGATTCCGCAG-3'

Primer E:
(SEQ ID NO: 24)
5'-GATTTTAAAATTGCMCCATCAGAGAGTAGACAGT-3'

Screening for Potentially Thermostable TdT Mutants

Amplified mutant library plasmids were transformed into expression strain *E. coli* BL21 (DE3). The recovered cells were plated on LB agar supplemented with 50 µg/mL kanamycin and incubated overnight at 37° C. Individual colonies were picked and inoculated into 200 µL LB supplemented with 50 µg/mL kanamycin in a 96-deepwell plate. The grown cell culture and downstream processes were carried out as stated above, under 'Establishing a plate-based FRET assay' (FIG. 6). The diluted and lysed cell lysate were subjected to different heat treatment before adding in 2bA FAM oligo and Cy5-dCTP.

For first round of screen with SUMO-TdT template-based mutant library, the diluted and lysed cell lysate were divided into two samples, one subjected to no heat treatment and the other subjected to 47° C. for 1 min. A library size of 2790 mutants was screened.

For second round of thermostability screen, TdT1-1 identified from round one was used as the template for mutagenesis. A library size of 7356 was screened with an aliquot of each cell lysate undergoing no heat treatment and the remaining aliquot subjected to heat treatment at 50° C. for 1 min.

One of the mutant libraries for third round of thermostability screen was created using degenerate primers each consisting either WT sequence or the mutations identified from the top four mutants from round two (TdT2-1, TdT2-2, TdT2-3 and TdT2-4) based on TdT1-1 template to give a combinatorial mixed pool. A library size of 736 was screened with an aliquot of each cell lysate samples subjected to no heat treatment and the remaining cell lysate subjected to 55° C. for 1 min. The same was done for TdT1-3 template-based mutant library, with an aliquot of each cell lysate samples subjected to no heat treatment and remaining aliquot subjected to 58° C. for 1 min.

The top mutant(s) from each library were identified; the genes were prepared for sequencing. The information on the mutations obtained were inserted into the parent plasmid and re-transformed into the expression *E. coli* strain. Approximately five or six colonies of the same mutant were selected, and a repeat of the FRET assay was done. Average data from average FRET signal from $15^{th}$ to $30^{th}$ min read for each mutant was obtained and plotted. The activity ratio for each TdT was obtained by dividing average FRET readout under heat treatment by average FRET readout under no heat treatment. Student's T-Test assuming unequal variance was done to determine the significance difference between the average FRET signal from parent TdT and mutant TdT.

Purification of TdT

Plasmids containing SUMO-TdT and TdT3-2 were expressed in E. coli BL21 (DE3). Each E. coli construct were grown in 6 L 2xYT broth (Bio Basic, Canada) supplemented with 50 μg/mL kanamycin. Cell culture were induced with 1 mM IPTG when $OD_{600nm}$ ~0.8. Induction was carried out at 15° C. for at least 16 h, at 250 rpm. Induced cells were harvested by centrifugation at 6500 rpm, 4° C.for 6 minutes using Beckman Coulter (Brea, CA, USA) JLA10.500 rotor in a 500 mL Beckman Coulter plastic container. The cell pellet was resuspended in a total of 120 mL binding buffer (20 mM Tris-HCl (pH 7.9), 500 mM NaCl and 5 mM imidazole) at 4° C. Resuspended cells were lysed using a microfluidizer (Microfluidics International Corporation, Westwood, MA, USA) with pressure of 20 000 psi for five passes. Supernatant was collected after centrifugation at 20 000 rpm, 4° C.for 20 min using Beckman Coulter JA25.5 rotor. A Chelating Sepharose® (a crosslinked, beaded-form of agarose) Fast Flow column (Pharmacia Biotech, Piscataway, NJ, USA) charged with $Ni^{2+}$ on AKTA Pure instrument (GE Healthcare Life Science, Chicago, IL, USA) was used to purify the His-tagged TdT from the supernatant. Samples from several fractions were analyzed on 15% sodium dodecyl sulfate polyacrylamide gel electrophoresis (SDS-PAGE) gel. Fractions containing the desired bands corresponding to TdT were pooled and dialyzed with Buffer 1 (20 mM Tris-HCl, pH 8, 100 mM NaCl, 100 mM histidine, 0.1 mM 2,2'-bipyridyl) using 10 kD molecular weight cutoff (MWCO)s dialysis membrane (Spectrum Chemical, USA) for at least 6 h at 4° C. Buffer 1 was changed to Buffer 2 (50 mM Tris-HCl, pH 8) for at least 4 h, 4° C., before loading the dialyzed proteins onto 10 mL Q Sepharose® (a crosslinked, beaded-form of agarose) column (GE Healthcare Life Sciences). Elution was done by (1 M NaCl) over 1 CV. Small aliquots of fractions with high $Abs_{280nm}$ on the chromatogram were analyzed on 15% SDS-PAGE gel. Fractions containing expected bands corresponding to respective TdT were pooled and dialyzed with protein storage buffer (20 mM Tris-HCl pH 8, 100 mM NaCl). Dialyzed proteins were aliquoted in small volume, frozen in liquid nitrogen and stored in −80°C.

Purified SUMO-TdT and TdT3-2 purity were analyzed via nuclease assay test. Each protein (0.5 μg) was incubated with 1 μg single stranded DNA (5'-TCTAGAGCCCGCCTAATCAGCGGGCTTTTTTTTAT-3', SEQ ID NO: 25) in 1x Tris/acetate (TA) buffer (30 mM Tris, 66 mM potassium acetate, 10 mM magnesium acetate, 0.5 mM DTT, pH 7.8) for 16 h at 37° C. Negative control using nuclease-free enzyme such as polymerase sample from Illumina, Inc. (San Diego, CA, USA) and positive control using DNaseI (New England Biolabs, USA) were included. Samples were visualized on 15% TBE-Urea gel (Invitrogen, USA).

Determining Thermostability of TdT3-2

Differential Scanning Calorimetry (DSC) (TA Instruments, New Castle, DE, USA) was performed to verify the thermostability of SUMO-TdT and TdT3-2. Temperature range of 20° C. to 80° C. and scan rate of 60° C./h were used. SUMO-TdT and TdT3-2 were diluted to about 1 mg/mL using 1xTdT buffer and 1 mL of each protein were loaded into DSC. Duplicates of each protein were loaded, and average of the heat capacity was plotted on a graph.

Nano-Differential Scanning Fluorimetry (DSF) (NanoTemper, Germany) was conducted to verify the thermostability of SUMO-TdT and TdT3-2. Excitation power were set at 14%, with scan rate at 60° C./h from 20° C. to 80° C. Fluorescence measurements were made at an excitation wavelength of 470 nm. DSF signal ratio F350/F330 were calculated from emitted intensities at 330 nm (F330) and 350 nm (F350). Light scattering measurement were made in parallel. Each protein sample (10 μL) of approximately 1 mg/mL were loaded into nanoDSF and duplicates of each sample were measured. The average of—first derivative of ratio F350/F330 was plotted.

SYPRO Orange thermal shift assay was performed to verify SUMO-TdT and TdT3-2 thermostability. Duplicates of each protein of 4 μg each, with final 5xSYPRO Orange dye (Life Technologies, Carlsbad, CA, USA) was used for the assay. Temperature range of 4° C. to 95° C. with 0.5° C. increment per 30 s were programmed. The change in relative fluorescence (RFU) over temperature (−dRFU/temperature) was obtained and the average was plotted against temperature.

Circular Dichroism (CD) as employed to assess the thermostability of SUMO-TdT and TdT3-2. Chirascan (Applied Photophysics, United Kingdom) Q100 with 0.1 mm manual quartz cuvette was used for this study. Protein unfolding was monitored at 198 nm-260 nm wavelengths as a function of temperature and 222 nm wavelength was used for the data analysis. The sample was diluted in 1xTdT buffer to the final protein concertation of 1.6 mg/ml. The temperature ramp set from 25° C. to 70° C. and 1° C./min rate and 0.2° C. tolerance. Instrument bandwidth was set to 1 nm with 1 second acquisition time per point. Two separate measurements were taken for each condition. The average of—first derivative of CD (222 nm) was plotted.

End-point assay were carried out to verify the activity of SUMO-TdT and TdT3-2 at 25° C., 36° C., 47° C. and 58° C. NEB TdT (5 Units) and purified SUMO-TdT and TdT3-2 (100 nM each) were incubated with 200 nM FAM oligo (5'-/56-FAM/ATTCAGGACGAGCCTCAGACC-3', SEQ ID NO: 26), 5 μM dCTP and 1xTdT buffer for 5 min, 10 min and 20 min at 25° C., 36° C., 47° C. and 58° C. Reactions were quenched by subjecting the samples to 90° C. for 5 min. Equal volume of 2xTBE-Urea sample buffer were added to each sample before heating at 80° C. for 5 min. The samples were visualized on 15 TBE-Urea gel (240 V, 62 min). The gels were imaged on Gel Doc XR+(Bio-Rad, USA).

Activity of commercial NEB TdT and TdT3-2 on blunt end DNA substrate was tested. Blunt end DNA substrate consisted of primer (5'-/56-FAM/TTTCGGTGGTCGCCGTATCCGC-3', SEQ ID NO: 27) and template (5'-GCGGATACGGCGACCACCGAGATCTACACTCTGAG/3Phos/-3', SEQ ID NO: 28) (IDT, USA). Double stranded DNA (ds DNA) products were prepared by heating a mixture of 4 μM DNA (primer to template, 1:3) and 1xTdT buffer at 95° C. for 5 min and allowed to cool to room temperature for at least 15 min. Enzymes (10 μL) and reaction mix (30 μL) were equilibrated to respective reaction temperature for 30 s. Enzymes were then aliquoted into the reaction mix, containing 200 nM ds DNA, 50 μM 2',3'-dideoxycytidine 5'-triphosphate (ddCTP) (JenaBioscience, Germany), 1xTdT buffer and 0.5 μM enzymes (or 25 U/20 μL reaction for NEB TdT), to 37° C. or 50° C. for 1 min, 2 min and 4 min. Samples (10 μL) at each time point were quenched by mixing with 8.3 μM displacer oligo and 2xTBE-Urea sample dye (Invitrogen, USA) (12 μL) and heated at 95° C. for 5 min before allowing to cool to room temperature. The displacer oligo (5'-TTTCTCAGAGTGTAGATCTCGGTGGTCGCCGTATCCGC/3Phos/-3', SEQ ID NO: 29) (IDT, USA) would anneal to the template and allow the primer to be displaced and exist as ssDNA, while the sample buffer and high temperature denature the enzyme.

Samples were visualized on 15 TBE-Urea gel (240 V, 68 min) and gels were imaged on Gel Doc. Quantification of the bands in each sample was completed using Image Lab software (Bio-Rad, USA). Reactions were done in duplicate and the average percentage of the primer with ddCTP incorporations were plotted using GraphPad (GraphPad Software, Inc., San Diego, CA, USA).

Kinetics Study of SUMO-TdT and TdT3-2

Reaction assays were set up with 200 nM FAM oligo, varying dCTP concentrations and 86 nM of SUMO-TdT and TdT3-2 in a final volume of 20 µL. Incorporation of dCTP by TdT were done at 37° C. for 15 s. Reactions were quenched by adding in 10 mM EDTA and equal total sample volume of 2×TBE-Urea sample buffer, heating at 80° C. for 5 minutes. The samples were loaded onto 15 TBE-Urea gel and allowed to run at 180 V for 1 h 30 minutes. Gels were imaged on Gel Doc XR+ and bands were analyzed on Image Lab. Band percentage of each band in a lane was obtained from the software and converted to amount of FAM oligo each band corresponds to. The size of the bands gave information on the number of incorporations of dCTP performed by the TdT and total turnover in nM for 20 µL reaction was calculated. The values obtained was converted to µM and the enzyme turnover rate in µM dCTP/s was obtained. The enzyme turnover rate was plotted against the concentration of dCTP in GraphPad Prism 8 using Michaelis-Menten analysis.

Kinetics of SUMO-TdT and TdT3-2 were also studied at 47° C. Reactions were set up with 200 nM FAM oligo, 173 nM SUMO-TdT and TdT3-2 and varying dCTP concentrations (final 20 µL). Incorporations of dCTP were carried out at 47° C. for 5 s. Subsequent quenching and analysis is the same as the kinetics performed at 37° C. in the paragraph above.

Modelling of TdT3-2 3D Structure

Amino acid sequence of TdT3-2 (Table 1) were input into Phyre2 web portal (http://www.sbg.bio.ic.ac.uk/phyre2/html/page.cgi?id=index). 'NORMAL' mode was selected. The 3D structure was modelled.

TABLE 1

Amino acid sequences of SUMO-TdT (bovine) and TdT3-2. The four underlined sequences in the SUMO-TdT (bovine) sequence are a His tag, a thrombin cleavage site, a SUMO fragment, and a bovine TdT fragment of amino acids 139-520. The four underlined sequences in the TdT3-2 sequence are a His tag, a thrombin cleavage site, a SUMO fragment, and a bovine TdT fragment of amino acids 139-520 with eight substitution mutations (E175V, K177N, E178G, D226Y, K271E, F280L, M283K, and H405P).

| Construct | Amino acid sequence |
|---|---|
| SUMO-TdT | MGSSHHHHHHGSGLVPRGSASMSDSEVNQEAKPEVKPEVKPETHINLKVS DGSSEIFFKIKKTTPLRRLMEAFAKRQGKEMDSLRFLYDGIRIQADQTPED LDMEDNDIIEAHREQIGGELMRTDYSATPNPGFQKTPPLAVKKISQYACQR KTTLNNYNHIFTDAFEILAENSEFKENEVSYVTFMRAASVLKSLPTIISMK DTEGIPCLGDKVKCIIEEIIEDGESSEVKAVLNDERYQSFKLFTSVFGVGLK TSEKWFRMGFRSLSKEVISDKTLKFTKMQKAGFLYYEDLVSCVTRAEAEA VGVLVKEAVWAFLPDAFVTMTGGFRRGKKIGHDVDFLITSPGSAEDEEQL LPKVINLWEKKGLLLYYDLVESTFEKFKLPSRQVDTLDHFQKCFLILKLHH QRVDSSKSNQQEGKTWKAIRVDLVMCPYENRAFALLGWTGSRQFERDIR RYATHERKMMLDNHALYDKTKRVFLKAESEEEIFAHLGLDYIEPWERNA (SEQ ID NO: 14) |
| TdT3-2 | MGSSHHHHHHGSGLVPRGSASMSDSEVNQEAKPEVKPEVKPETHINLKVS DGSSEIFFKIKKTTPLRRLMEAFAKRQGKEMDSLRFLYDGIRIQADQTPED LDMEDNDIIEAHREQIGGELMRTDYSATPNPGFQKTPPLAVKKISQYACQR KTTLNNYNHIFTDAFEILAENSVFNGNEVSYVTFMRAASVLKSLPFTIISMK DTEGIPCLGDKVKCIIEEIIEYGESSEVKAVLNDERYQSFKLFTSVFGVGLK TSEKWFRMGFRSLSEIMSDKTLKLTKKQKAGFLYYEDLVSCVTRAEAEAV GVLVKEAVWAFLPDAFVTMTGGFRRGKKIGHDVDFLITSPGSAEDEEQLL PKVINLWEKKGLLLYYDLVESTFEKFKLPSRQVDTLDHFQKCFLILKLPHQ RVDSSKSNQQEGKTWKAIRVDLVMCPYENRAFALLGWTGSRQFERDIRR YATHERKMMLDNHALYDKTKRVFLKAESEEEIFAHLGLDYIEPWERNA (SEQ ID NO: 15) |

Results and Discussion

Establishing a Plate-Based FRET Assay for the Detection of TdT Activity

Figure 3A:
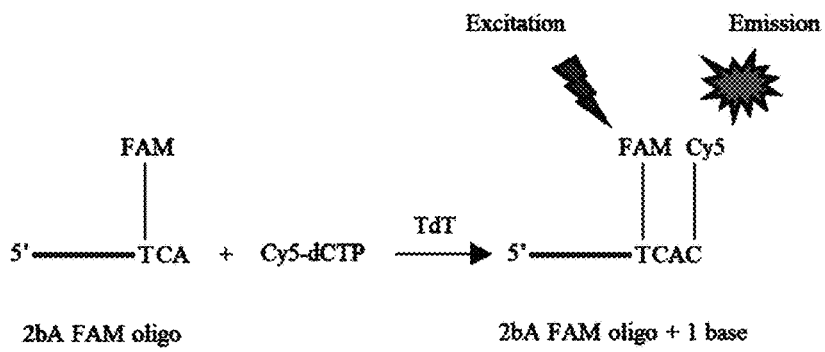
FIGS. 3A-3E show establishing FRET assay for the detection of TdT activity.
Figure 3B:
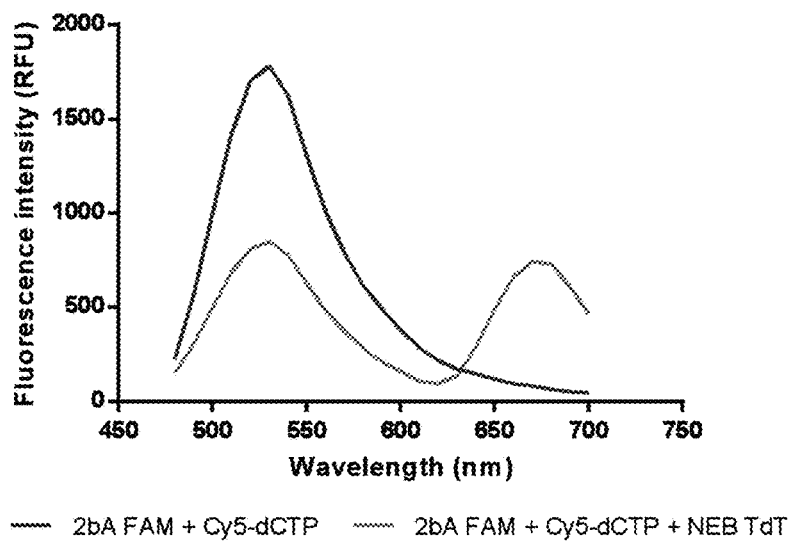

The high throughput assay to screen for thermostable TdT variants described in this example is a Förster resonance energy transfer (FRET)-based assay that determines TdT activity which covalently links a primer to a nucleotide (FIGS. 2 and 3A). Firstly, the optimal distance of the donor dye and acceptor dye needed to be determined. The FAM-TAMRA FRET pair was utilized, while varying the distance of the FAM from the 3' end. Having the FAM donor dye two bases away from the 3'end of the oligo gave the greatest decrease in FAM emission. However, the corresponding increase in emission from carboxytetramethylrhodamine (TAMRA) was low (FIG. 4, Table 2). To obtain a higher acceptor emission signal, different FRET pairs (FAM-Cy5 and Cy3-Cy5) were tested while the donor at the optimal 2 bases away from the 3' end were retained (FIG. 4, Table 3).

FAM-Cy5 provided the best increase in signal detected from acceptor Cy5's emission at 670 nm (FIG. 3B and FIGS. 5A-5C). A primer with FAM at 2 bases from the 3' end (2bA FAM) and Cy5-dCTP were used for subsequent screens for active TdT mutants (FIG. 3A).

empty plasmid (48 of each) were inoculated in a 96-deep-well plate and the respective lysates assayed after 50× dilution using the FRET assay previously developed. Cell lysates expressing SUMO-TdT have higher FRET readout and could be differentiated from the negative controls (FIG.

TABLE 2

Oligo and nucleotides investigated to identify optimum distance between FAM donor dye and TAMRA acceptor dye.

| Oligo | Sequence (5' to 3') | FAM dye distance from 3' end (bases) | Best FRET signal from given oligo and nucleotide combination |
|---|---|---|---|
| 1bA FAM | CGC TTG CAC AGG TGC GTTC/iFluorT/A (SEQ ID NO: 30) | 1 | |
| 2bA FAM | CGC TTG CAC AGG TGC GTT/iFluorT/CA (SEQ ID NO: 16) | 2 | X |
| 5bA FAM | CGC TTG CAC AGG TGC/iFluorT/ GTTCA (SEQ ID NO: 31) | 5 | |
| 10bA FAM | CGC TTG CAC A/iFluorT/GGTGC GTTCA (SEQ ID NO: 32) | 10 | |

TABLE 3

Oligo and nucleotides examined to select optimal FRET pairs for the detection of active TdT.

| Oligo | Sequence (5' to 3') | Dye on dCTP | Combination of oligo and nucleotides that gave best FRET detection for active TdT |
|---|---|---|---|
| 2bA FAM | CGC TTG CAC AGG TGC GTT/iFluorT/CA (SEQ ID NO: 16) | TAMRA | |
| 2bA FAM | CGC TTG CAC AGG TGC GTT/iFluorT/CA (SEQ ID NO: 16) | Cy5 | X |
| 2bA Cy3 | CGC TTG CAC AGG TGC GT/iCy3/TCA (SEQ ID NO: 33) | Cy5 | |

Figure 3C:
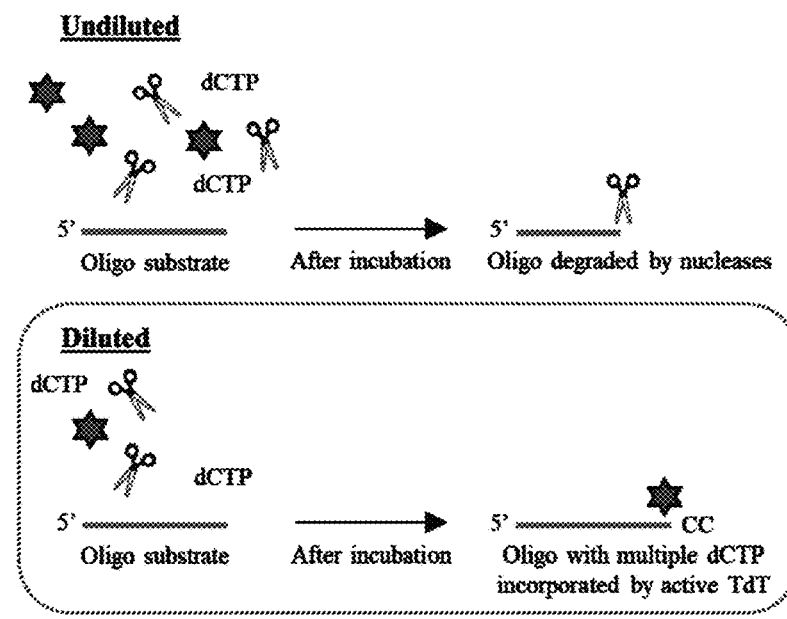
Figure 3D:
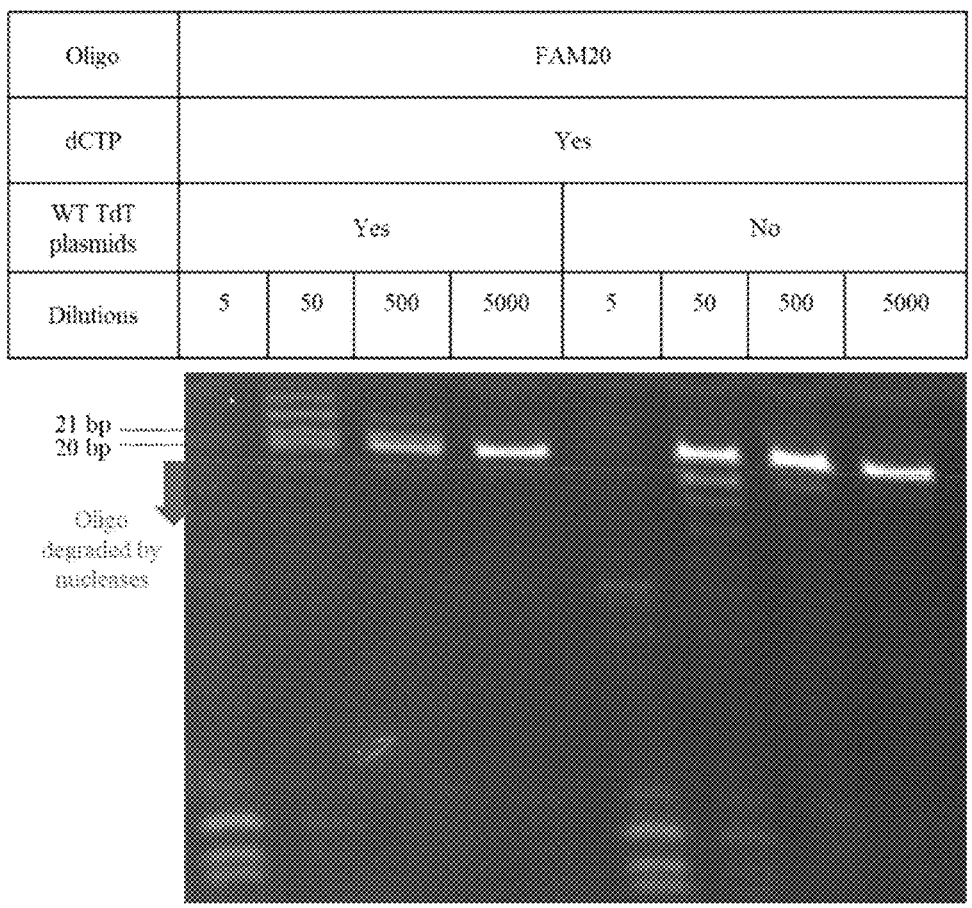
Figure 3E:
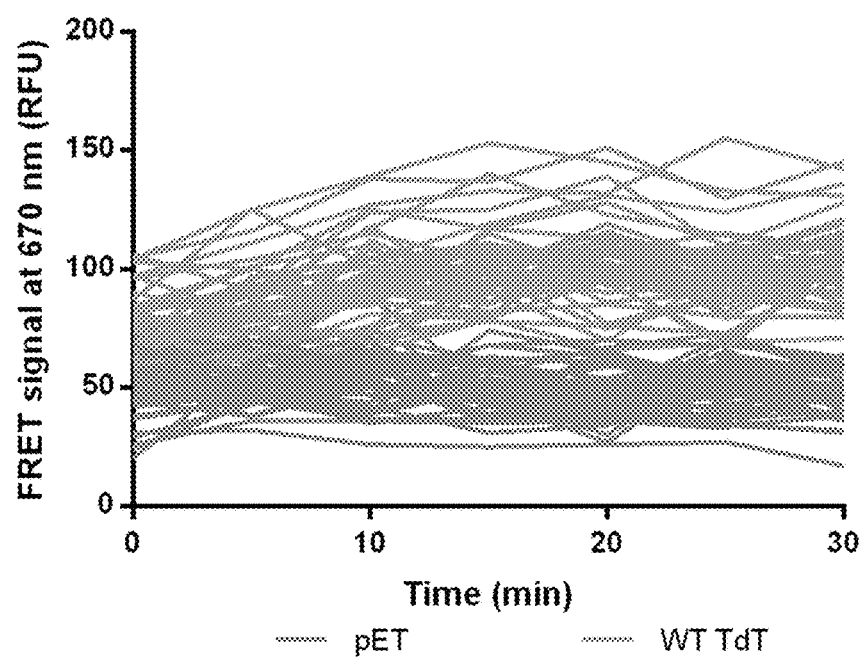
Figure 4A:
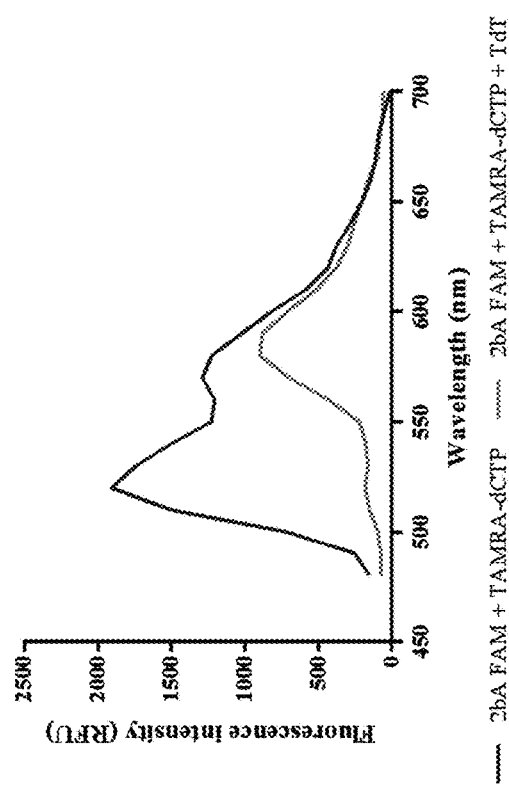
FIGS. 4A-4D show emission wavelength scans of different FAM-tagged oligo with TAMRA-dCTP with excitation at 450 nm.
Figure 4B:
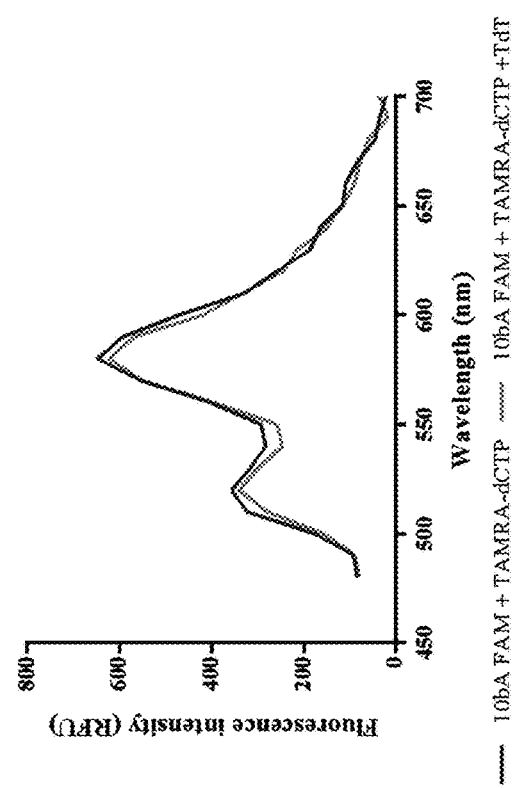
Figure 4C:
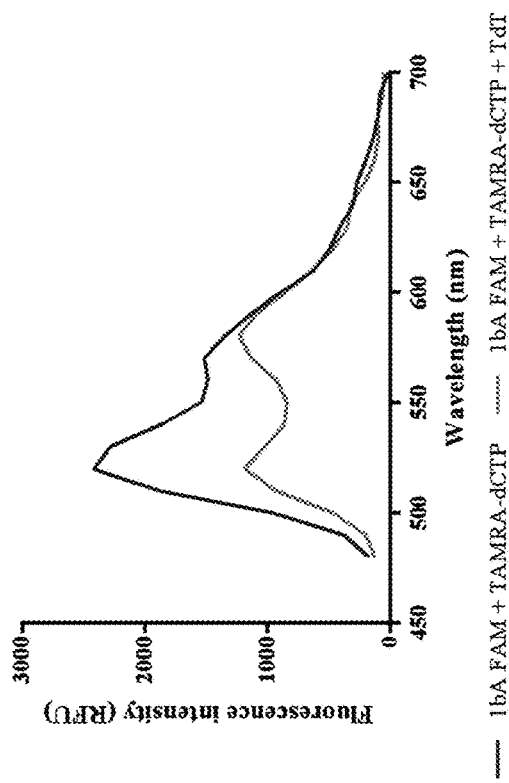
Figure 4D:
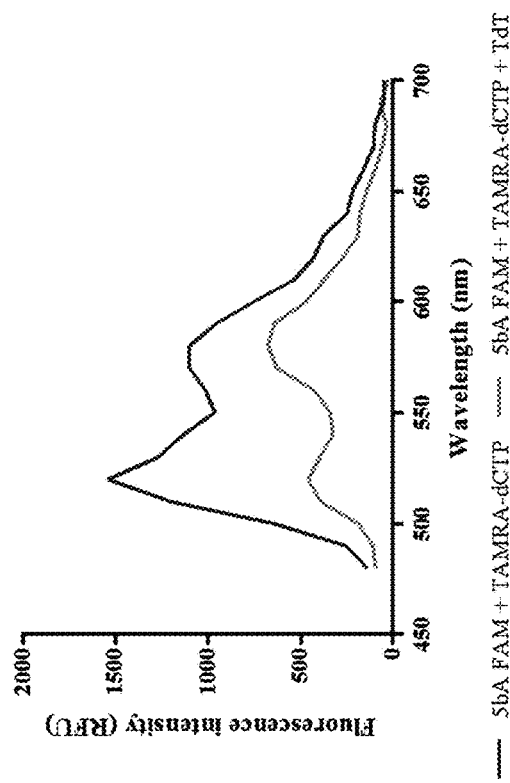
Figure 5A:
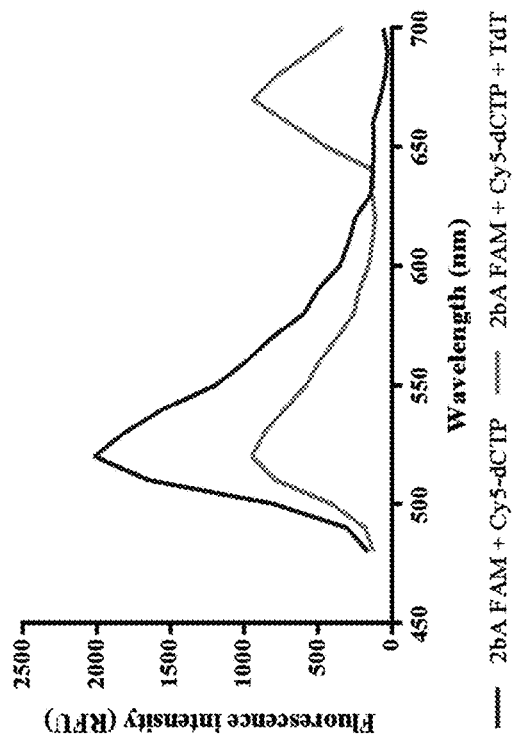
FIGS. 5A-5C show emission wavelength scans of different FRET pairs.
Figure 5B:
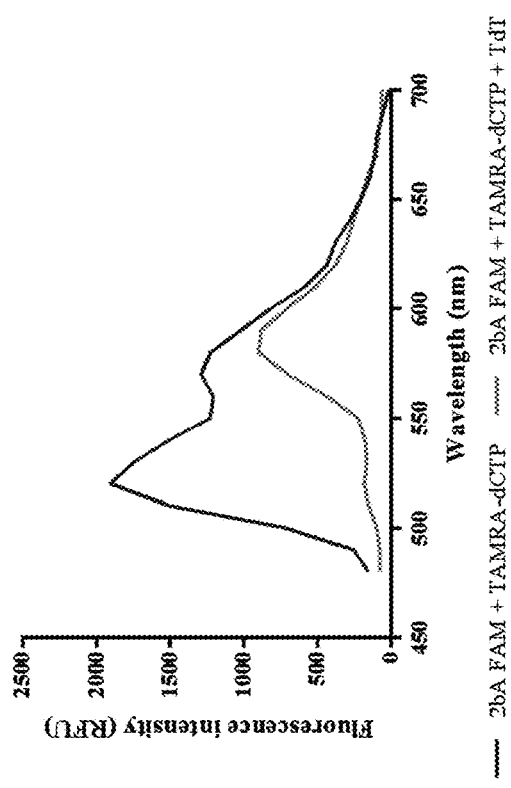
Figure 5C:
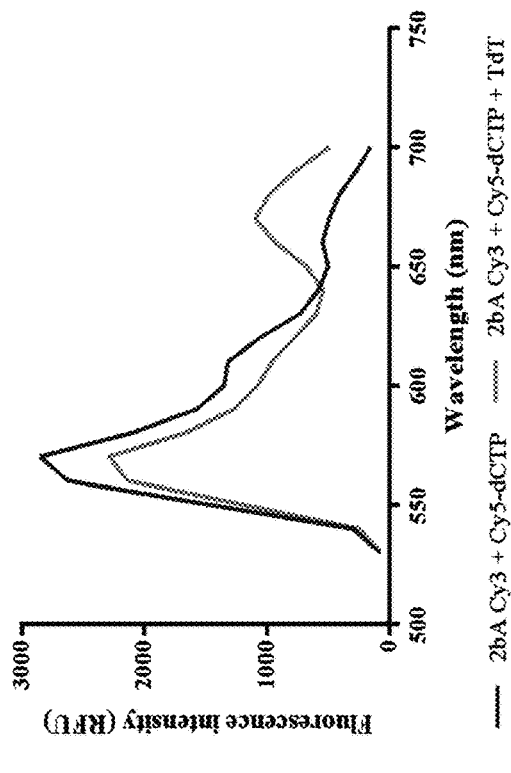

For practical high throughput screening, the assay would be best conducted with unpurified lysates, as purification steps would add time and cost burdens. However, utilizing crude cell lysate was problematic, as the presence of endogenous E. coli nucleases could mask TdT activity (FIG. 3C, top row). One potential way to overcome this problem was to dilute the cell lysate. Without being bound by any particular theory, diluting the cell lysate might diminish nuclease activity disproportionately compared to TdT, for example if TdT were to have a higher binding affinity to oligo substrate, or if overexpression of TdT leads to higher concentration of TdT compared to nucleases after cell lysate dilution (FIG. 3C, bottom row). To determine the validity of this hypothesis, cell lysates expressing SUMO-TdT were diluted 5, 50, 500 and 5000 times, and the incorporation reaction was then analyzed on polyacrylamide gels. Bands corresponding to +1 and more were observed for 50- and 500-fold diluted cell lysates, while nuclease activity predominated at 5-fold dilution (FIG. 3D). A 50× dilution factor was selected for the thermostability screen along with the FAM-Cy5 FRET pair seen above.

To determine the robustness of the resulting plate-based FRET assay, colonies expressing either SUMO-TdT or an 3E). Based on this result, a workflow for a 96 well plate-based FRET assay to screen for potentially thermostable TdT mutants was established, as depicted in FIG. 6. This includes an initial heat shock step to distinguish between thermostable and thermosensitive mutants. Note that selection pressure can be tuned by changing the temperature and duration of the heat shock step.

Discovery of Thermostable TdT3-2

Figure 7A:
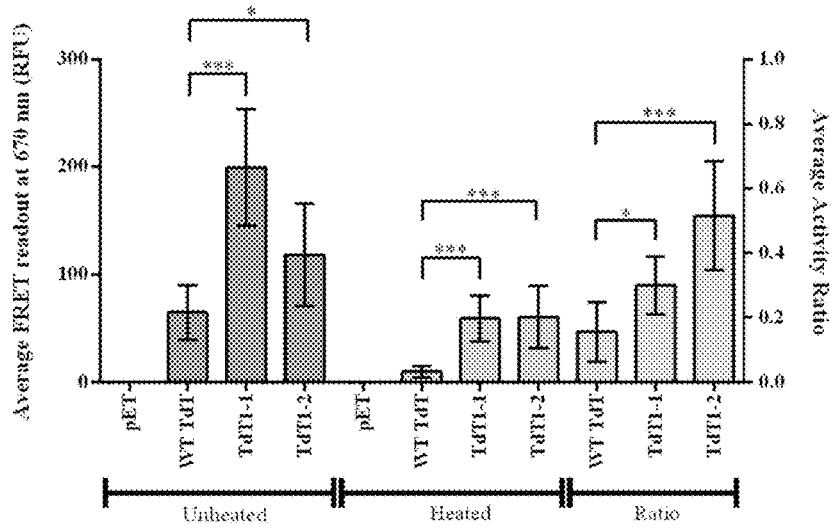
FIGS. 7A-7D show FRET readout of TdT variants across the three rounds of thermostability screen.

Mutant libraries were generated via random mutagenesis. The first mutant library used SUMO-TdT (i.e., a TdT of bovine origin that has the N-terminal 138 amino acids deleted and contains an N-terminal SUMO-tag) as the parent template. A library of 2790 mutants was screened with heat treatment at 47° C. for 1 min. This round identified thermostable mutants TdT1-1 and TdT1-2 as thermostable (FIG. 2 and Tables 4A and 4B). TdT1-1 and TdT1-2 have significantly higher FRET readout without and with heat treatment as compared to SUMO-TdT (FIG. 7A). Also, TdT1-1 and TdT1-2 retained a larger proportion of their activity after heat treatment (FIG. 7A).

TABLE 4A

Summary table of TdT variants from thermostability screen. The positions of the substitution mutations are the positions in the SUMO-TdT (and TdT variants thereof). See FIG. 1 for the positions of the substitution mutations in SUMO-TdT (and TdT variants thereof) and corresponding positions in Bos taurus TdT.

| Screening Round | Temperature [d] (° C.) | Parent template[g] | Library size | Positive TdT variants[e] | Mutations[f] |
|---|---|---|---|---|---|
| 1[a] | 47 | SUMO-TdT | 2790 | TdT1-1 | E175V |
|  |  |  |  | TdT1-2 | D226Y |
| 2[b] | 50 | TdT1-1 | 7636 | TdT2-1 | M283K |
|  |  |  |  | TdT2-2 | K271E, T326S |
|  |  |  |  | TdT2-3 | E178G, F280L, H405P |
|  |  |  |  | TdT2-4 | K177N |
| 3[c] | 55 | TdT1-1 | 736 | TdT3-1 | K177N, E178G, K271E, F280L, M283K |
|  | 58 | TdT1-3[h] | 736 | TdT3-2 | K177N, E178G, K271E, F280L, M283K, H405P |

[a]Mutant library for Round 1 was created by random mutagenesis via error-prone PCR
[b]Mutant library for Round 2 was created by random mutagenesis via error-prone PCR
[c]Mutant library for Round 3 were created by combining the mutations identified from TdT2-1, TdT2-2, TdT2-3 and TdT2-4
[d]Temperature that crude cell lysate was subjected to during the screen
[e]Positive TdT variants identified from each rounds of screening
[f]Mutations found in positive TdT variants in [e] when compared to parent template stated in [g]
[h]TdT1-3 is derived from the combination of mutations E175V and D226Y from TdT1-1 and TdT1-2

TABLE 4B

Summary table of TdT variants from thermostability screen. Some mutants discovered from round 1, round 2 and round 3 are shown. Some mutations discovered from round 1 and round 2 are shown in the left-hand side column. No mutations are listed for round 3 because round 3 did not generate new mutations; round 3 mutants were generated by recombining round 2 mutations from different mutants. A checked box indicates the presence of the particular mutation from the left-hand side column in that mutant. The lowest row "Others" indicates mutations that occur serendipitously in round 2 (Del in an area not targeted for mutagenesis) or round 3. The positions of the substitution mutations are the positions in the SUMO-TdT (and TdT variants thereof).

|  |  | Mutants | | | | | | | | | |
|---|---|---|---|---|---|---|---|---|---|---|---|
|  |  | Round 1 | | Round 2 | | | | Round 3 | | | |
| Mutations | | C44 (TdT1-1) | C67 (TdT1-2) | M3 (TdT2-1) | M5 (TdT2-2) | M10 (TdT2-3) | M11 (TdT2-4) | CM1 (TdT3-1) | CM2 | CM3 | CM5 | CM12 (TdT3-2) |
| Round 1 | E175V | X |  | X | X | X | X | X | X | X | X | X |
|  | D226Y |  | X |  |  |  |  |  |  |  |  | X |
| Round 2 | K177N |  |  |  |  |  | X | X | X | X | X | X |
|  | E178G |  |  |  |  | X |  | X | X | X | X | X |
|  | K271E |  |  |  | X |  |  | X | X | X | X | X |
|  | F280L |  |  |  |  | X |  | X | X |  |  | X |
|  | M283K |  |  | X |  |  |  | X | X | X | X | X |
|  | T326S |  |  |  | X |  |  |  |  |  |  |  |
|  | H405P |  |  |  |  | X |  |  | X |  |  | X |
| Others |  |  |  | Del. 18G |  |  |  |  |  | M81I |  |  |

|  |  | Mutants Round 3 | | | | | | |
|---|---|---|---|---|---|---|---|---|
|  | Mutations | CM14 | CM15 | CM16 | CM19 | CM20 | CM24 | CM25 |
| Round 1 | E175V | X | X | X | X | X | X | X |
|  | D226Y | X | X | X | X | X | X | X |
| Round 2 | K177N | X | X | X | X | X | X | X |
|  | E178G | X | X | X |  | X | X | X |
|  | K271E | X | X | X | X | X | X | X |
|  | F280L | X |  | X | X | X | X |  |
|  | M283K | X | X | X | X | X |  | X |
|  | T326S | X |  |  |  |  |  |  |
|  | H405P |  |  |  | X |  |  | X |
|  | Others |  | N361K |  | K233G |  |  |  |

Figure 7B:
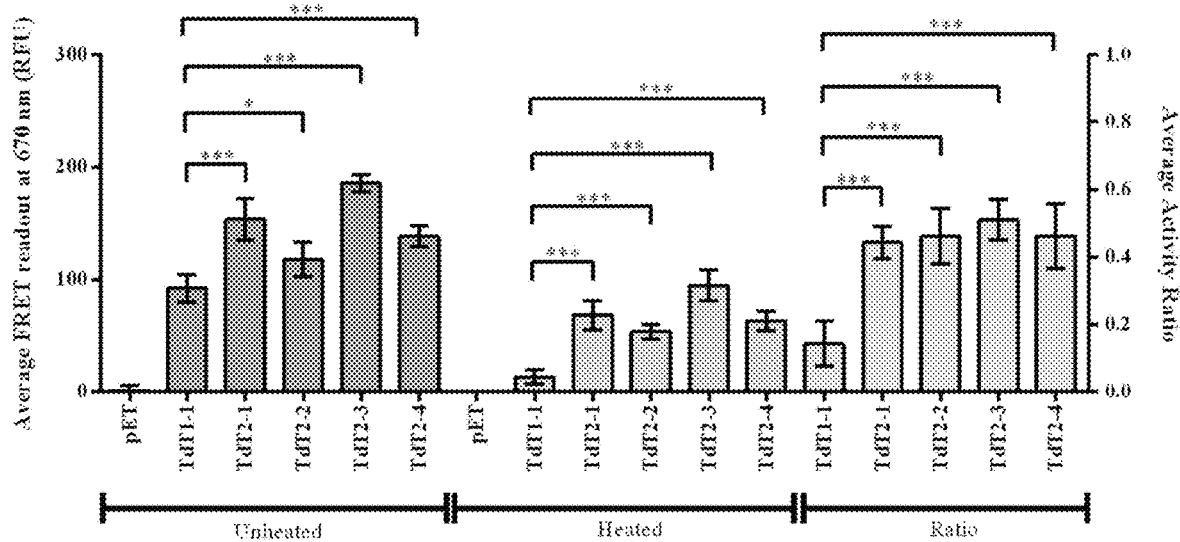

For the second round of screening, a library size of 7636 was generated using TdT1-1 as parent. TdT1-1 was selected as the parent template as TdT1-1 and higher FRET readout without heat treatment as compared to TdT1-2. The second round of screening was conducted with heat treatment of 50° C. for 1 min and four thermostable mutants were identified (TdT2-1, TdT2-2, TdT2-3, TdT2-4) (Tables 4A and 4B). The four mutants have significantly higher FRET readouts than TdT1-1 under both no heat treatment and heat treatment conditions (FIG. 7B). All four mutants also retained much higher proportion of their activity after being subjected to 50° C. for 1 min (FIG. 7B).

Figure 7C:
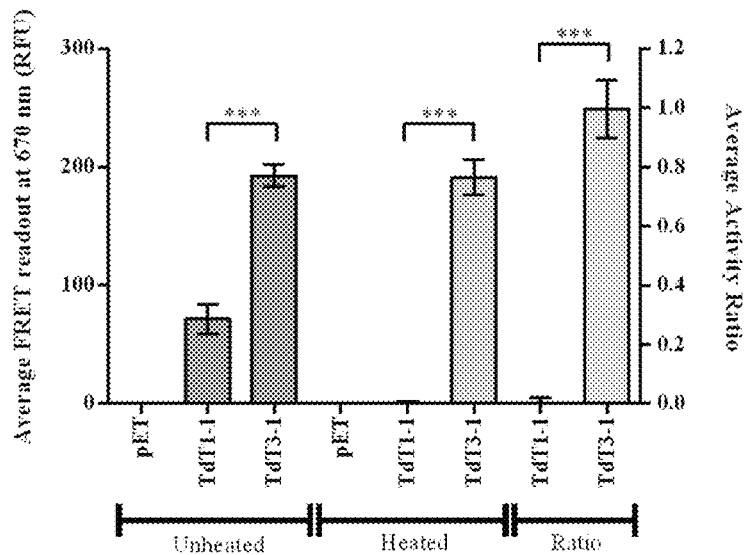
Figure 7D:
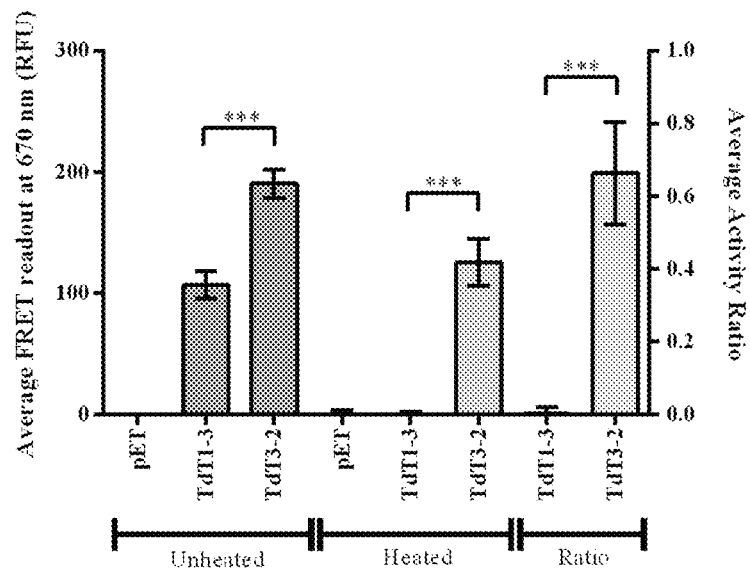

A combination of mutations identified from TdT2-1, TdT2-2, TdT2-3 and TdT2-4 was speculated to give a synergistic increase in thermostability. For the third round of the thermostability screen, two mutant libraries were generated. One of the mutant libraries was based on TdT1-1 template with different combinations of the mutations found in TdT2-1, TdT2-2, TdT2-3 and TdT2-4. The other mutant library was created similarly, except utilizing TdT1-3 as the parent template. TdT1-3 comprised of a combination of mutations in TdT1-1 and TdT1-2 (Tables 4A and 4B). The TdT1-1-based mutant library was screened with a 1 min heat shock at 55° C. TdT3-1, which was identified as the top mutant from this library (Tables 4A and 4B), had a much higher FRET readout both without and with heat-shock, and retained a higher fraction of its FRET activity after heat-shock (FIG. 7C). Screening of the TdT1-3-based mutant library with heat treatment at 58° C. for 1 min led to the discovery of TdT3-2 with significantly higher FRET readout under both room temperature and heat-shock treatment (FIG. 7D and Tables 4A and 4B). TdT3-2 retained at least half of its FRET activity after being subjected to 58° C. for 1 min (FIG. 7D). This suggests that TdT3-2 is significantly more active and thermostable than TdT1-3. As shown in Tables 4A and 4B, TdT3-2 carries most of the mutations identified from the top mutants from each round of screen, except T326S.

Figure 8A:
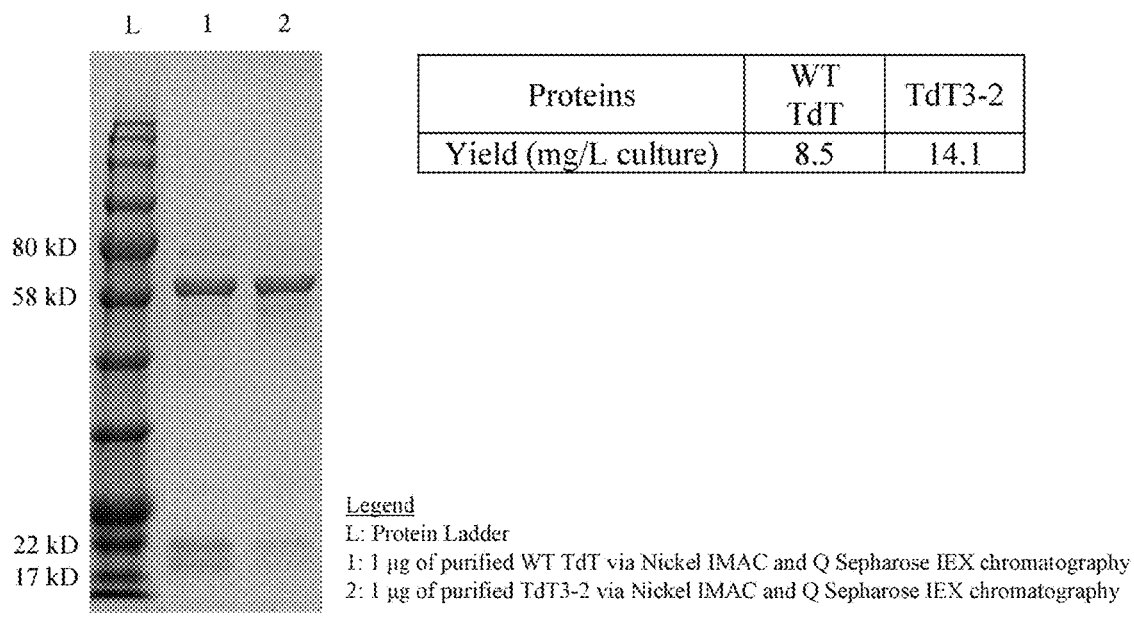
FIGS. 8A-8B show purification of SUMO-TdT and TdT3-2 and verification of nucleases contamination in purified TdTs.
Figure 8B:
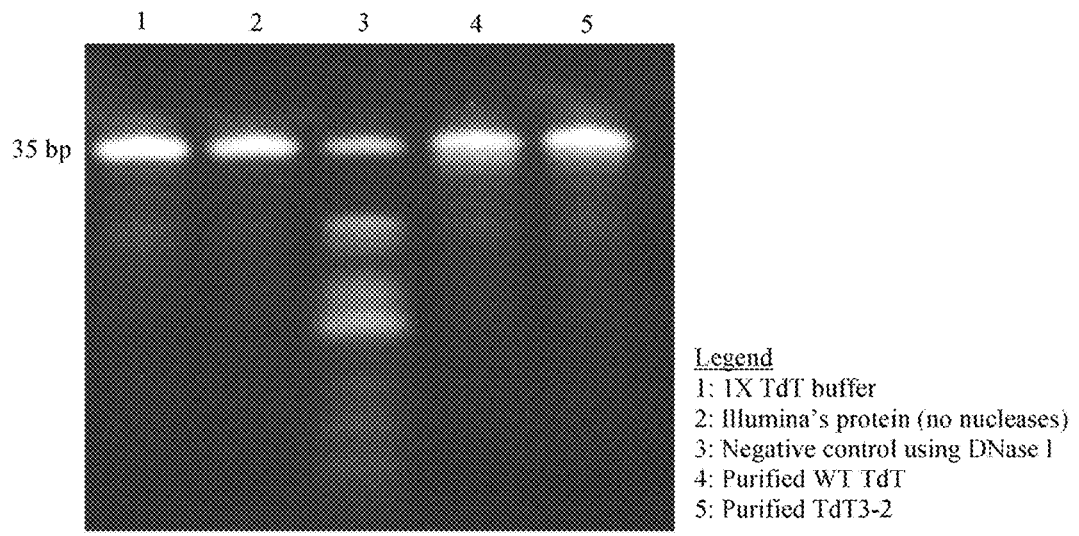

After identifying TdT3-2 as the optimally thermostable mutant, expression and purification processes were optimized to successfully obtain SUMO-TdT and TdT3-2 with minimum nuclease contamination (FIG. 8). It is important that purified SUMO-TdT and TdT3-2 have minimal nuclease activity, as nucleases would interfere with downstream characterization studies.

Verifying Thermostability of TdT3-2

Figure 9A:
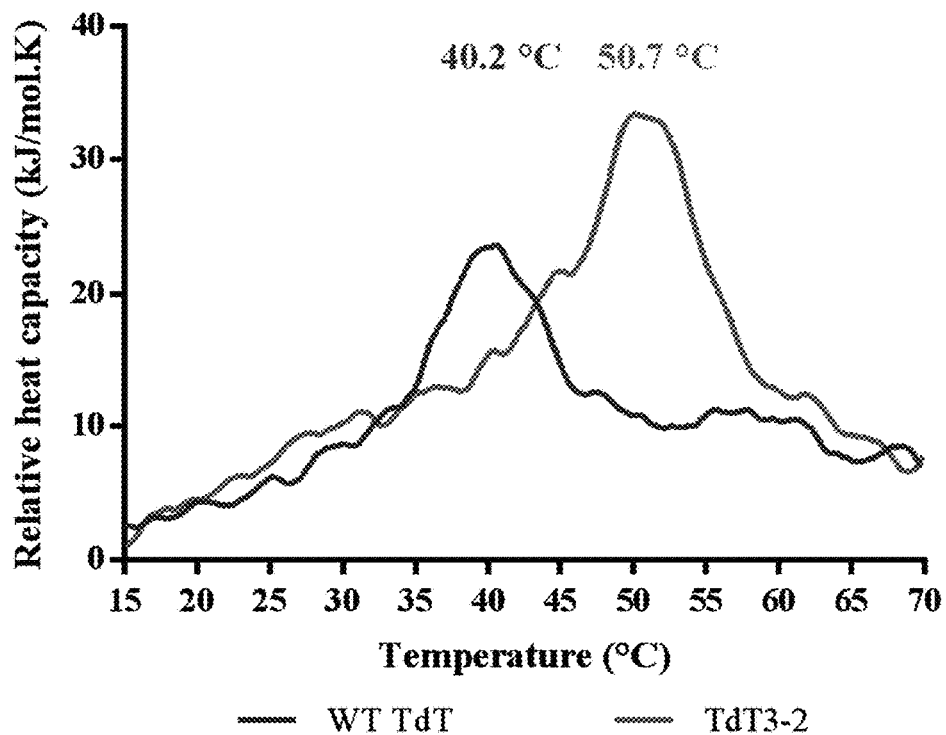
FIGS 9A-9D show $T_m$ measurement of purified SUMO-TdTand TdT3-2.
Figure 9B:
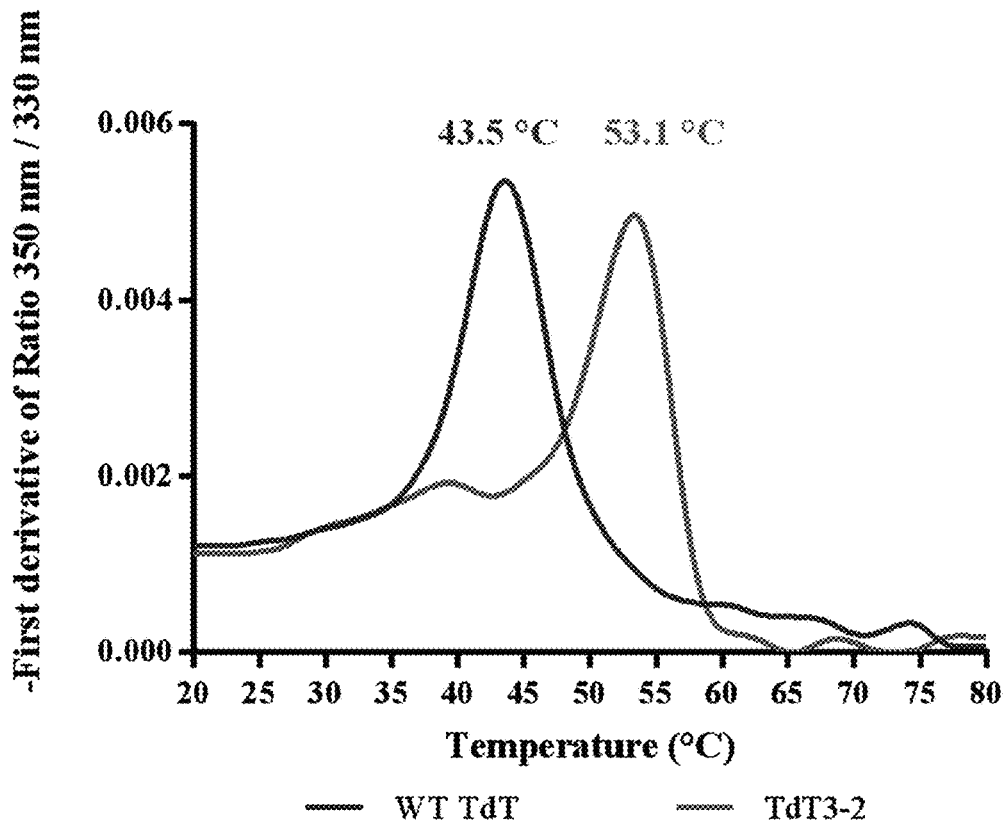
Figure 9C:
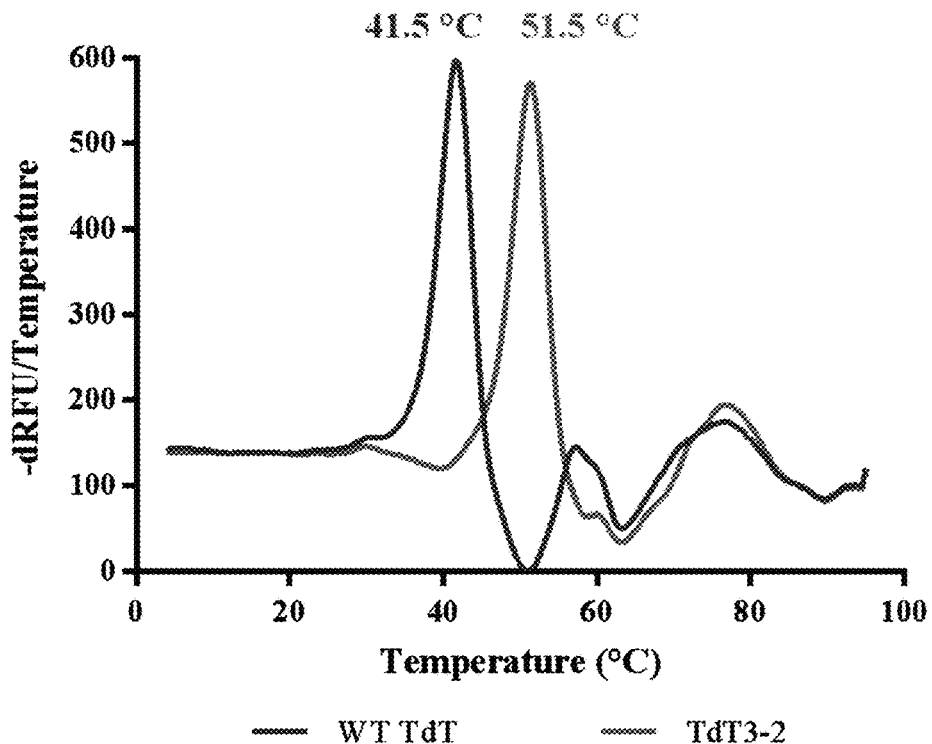
Figure 9D:
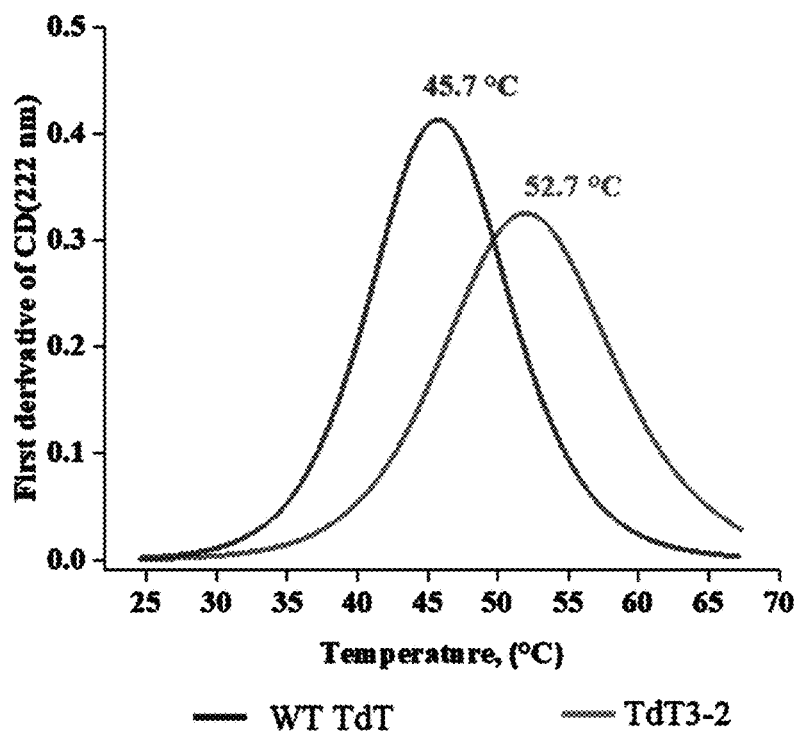

Characterization of TdT3-2 thermostability was performed via differential scanning calorimetry (DSC), differential scanning fluorimetry (DSF), SYPRO Orange thermal shift assay and Circular Dichroism (CD). DSC measures the energy required to disrupt the interactions stabilizing the proteins' tertiary structures. The $T_m$ obtained from DSC for SUMO-TdT is 40.2° C. and for TdT3-2 is 50.7° C. (FIG. 9A). To further validate the $T_m$ of SUMO-TdT and TdT3-2 from DSC, the same proteins were tested by DSF. DSF measures the fluorescence shift of intrinsic tyrosine and tryptophan residues as the protein unfolds. The negative derivatives of fluorescence readings were plotted against temperature and the maximum of this derivative curve corresponds to the $T_m$ of the protein. SUMO-TdT had an observed $T_m$ of 43.5° C. while TdT3-2 has $T_m$ of 53.1° C. (FIG. 9B). The $T_m$ of SUMO-TdT and TdT3-2 was further validated by SYPRO Orange thermal shift assay. SYPRO Orange dye binds non-specifically to hydrophobic regions exposed during protein unfolding. The derivative of the change in fluorescence signal corresponds to the $T_m$ of the protein. A $T_m$ of 41.5° C. was recorded for SUMO-TdT while 51.5° C. was observed for TdT3-2 (FIG. 9C). Circular Dichroism (CD) is a spectroscopic technique for following the unfolding of proteins as a function of temperature. CD measures characteristic spectral bands that can be attributed to α-helices and β-sheets. The changes in CD as a function of temperature, at characteristic wavelengths, can be used to determine the midpoint of the unfolding transition ($T_m$) for a protein. The first derivative values of CD at 222 nm wavelength were plotted against temperature with the maximum set as $T_m$. SUMO-TdT had an observed $T_m$ of 45.7° C. and TdT3-2 has $T_m$ of 52.5° C. (FIG. 9D).

CD measurements of $T_m$ transitions for both proteins were slightly higher when compared to other techniques. The higher melting temperature may be associated with the instrument set-up. The sample cuvette was in the contact with the Peltier holder via a metal adaptor that led to a small heat dissipation and may led to small overestimation of a sample temperature by 1-2° C. Nevertheless, the CD data was in a good agreement with the other experimental techniques showing the same stability trend between the two proteins. The data confirmed TdT3-2 to be ~10° C. more thermostable than SUMO-TdT.

Figure 10A:
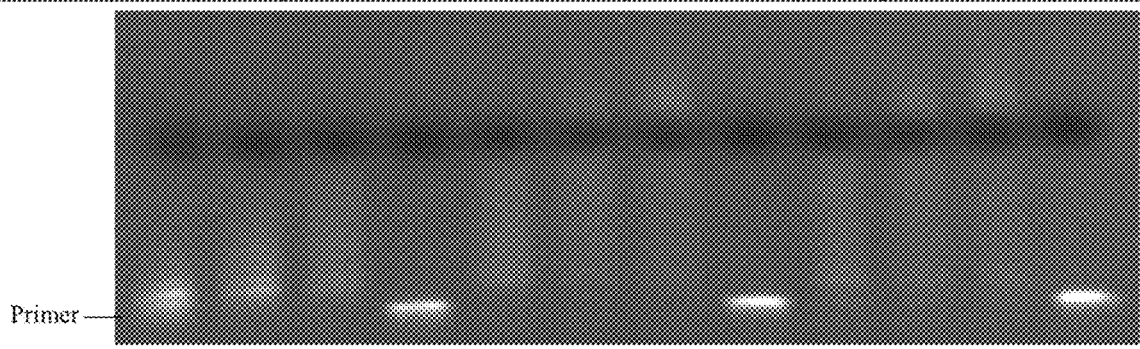
FIGS. 10A-10D are non-limiting exemplary gel images showing observations of commercial (NEB) TdT, SUMO-TdT and TdT3-2 activities at different temperatures. All TdTs were active at (FIG. 10A) 25° C.
Figure 10B:
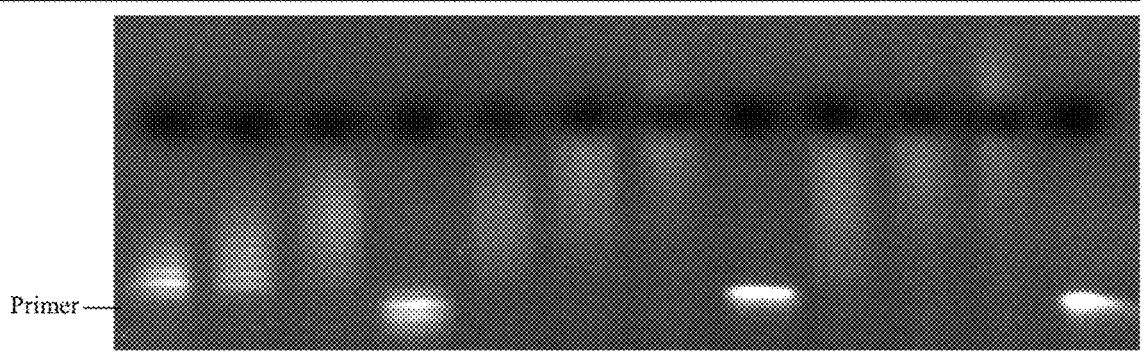
Figure 10C:
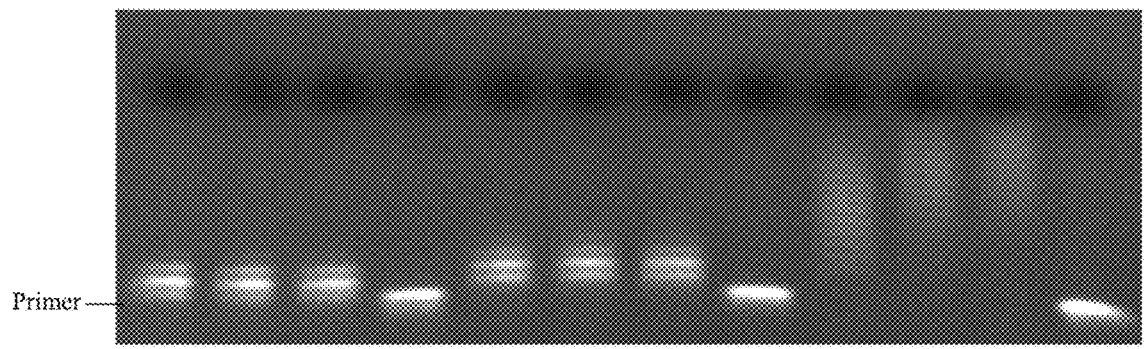
Figure 10D:
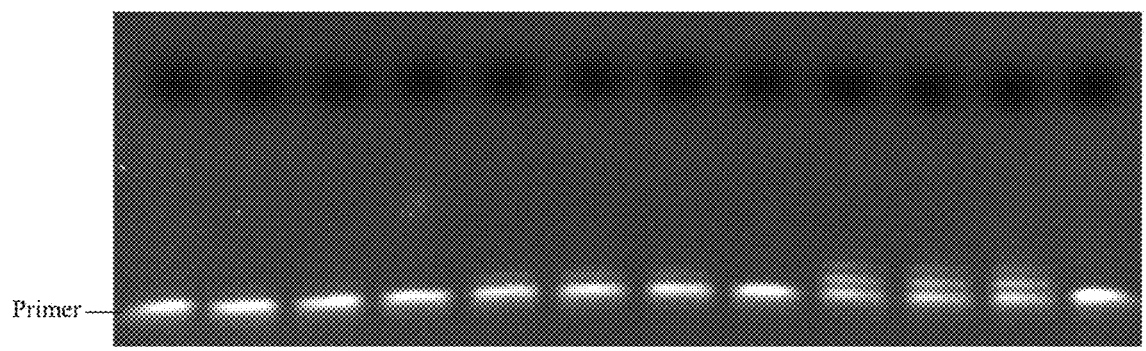

Primer extension reactions were carried out with commercial (NEB) TdT, SUMO-TdT, and TdT3-2 to determine if TdT3-2 incorporates nucleotides at elevated temperature. Reactions were carried out at 25° C., 36° C., 47° C. and 58° C. and the DNA products were visualized on TBE-Urea gel. All three enzymes are active at 25° C. and 36° C. (FIGS. 10A and 10B). At 47° C., commercial TdT and SUMO-TdT were denatured within 5 min as the intensities of the bands with incorporations remained the same for 5 min, 10 min and 20 min. In contrast, TdT3-2 was active for 20 min, as more incorporations could be seen for the 20 min reaction (FIG. 10C). At 58° C., commercial TdT and SUMO-TdT were not active, while TdT3-2 was denatured within 5 min as the intensity of the bands remains the same thereafter (FIG. 10D). This observation strongly confirms that TdT3-2 is more thermostable than SUMO-TdT, and that TdT3-2 remains active at higher temperature.

Figure 11:
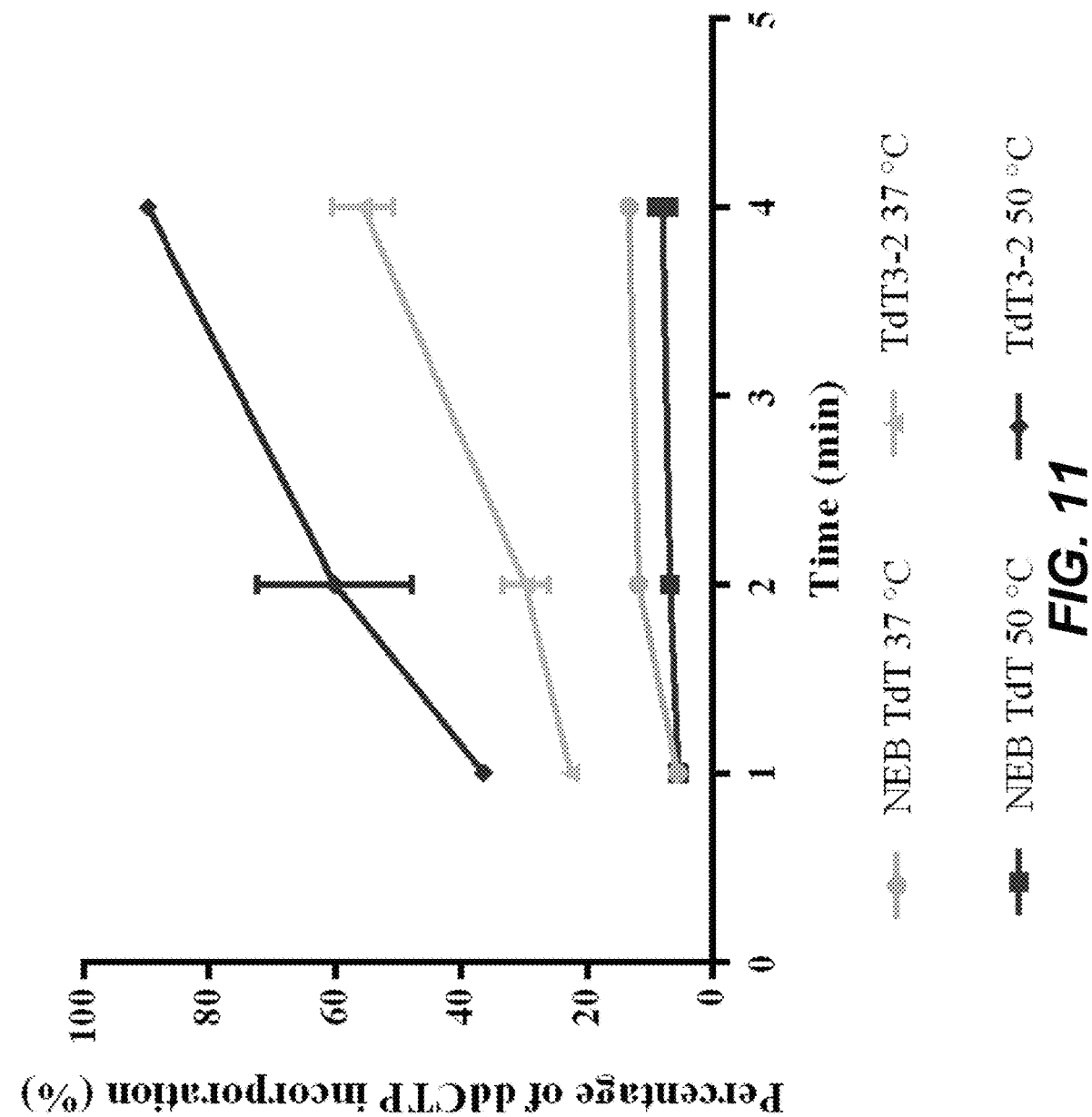
FIG. 11 is a non-limiting exemplary plot examining commercial TdT (NEB TdT) and TdT3-2 activities on ds blunt end DNA substrates. TdT3-2 was capable of incorporating higher amount of ddCTP onto ds blunt end DNA substrate at both 37° C. and 50° C. The percentage was increased at 50° C. At 37° C. for 4 min, the percentage of primer with ddCTP incorporated by NEB TdT was about 13.4% while TdT3-2 is 55.7%. For the same duration at 50° C., the percentage of incorporation of ddCTP onto the primer by NEB TdT was about 8% while TdT3-2 is about 89.9%.

TdT has been used in library preparation to elongate dsDNA samples before amplification. As TdT adds nucleotides to ssDNA, ds blunt end DNA will rely on transiently melted DNA at 3' end of primer for TdT to incorporate the first few nucleotides. DNA samples with high GC content might pose difficulty for TdT to elongate due to higher $T_m$. By increasing the temperature during library preparation using TdT, it would increase the proportion of dsDNA transiently melted to ssDNA at 3' end of primer for TdT to incorporate nucleotides. However, the TdT used in library preparation are not thermostable. We tested TdT3-2 on blunt end dsDNA, containing four GC base pairs at 3' of primer, to demonstrate its potential in improving the library preparation process. Comparing the percentage of incorporation of ddCTP between commercial TdT and TdT3-2, TdT3-2 performs better than commercial TdT at both 37° C. and 50° C. In addition, the elongation of the primer is higher for TdT3-2 at 50° C. (FIG. 11 and FIG. 12). This suggests potential performance of TdT3-2 in improving the current library preparation.

Kinetic Characterization of SUMO-TdT and TdT3-2

In order to determine more precisely whether the thermostabilized TdT variant maintained its terminal transferase activity, its steady-state activity was compared with that of SUMO-TdT. Steady-state assays were set up with an excess of DNA such that multiple turnovers could be observed even if distinguishing the number of incorporation events per enzyme turnover was not possible. Reactions at 37° C. with a titration of dCTP concentrations were each quenched at 15 seconds and the amount of product was quantified on Urea-PAGE, which allowed a total turnover in micromolar dCTP per second to be roughly estimated (see Materials and Methods, raw data in Table 5 and Table 6). When this rate was plotted against the dCTP concentration, a hyperbolic relationship was observed which consistent with Michaelis-Menten kinetics, allowing estimation of the maximal elongation rate and the Michaelis constant ($K_M$). TdT3-2 exhibited comparable activity to the SUMO-TdT, with a slightly elevated elongation rate and a lower $K_M$, suggesting this enzyme had slightly improved catalytic activity (Table 7). A kinetics study of SUMO-TdT and TdT3-2 at elevated temperature of 47° C. was performed. The same analysis method was adopted and estimated total turnover in micromolar dCTP per second was obtained (Tables 8 and 9). TdT3-2 had comparable activity at both 37° C. and 47° C., while SUMO-TdT had much lower activity at 47° C. as saturation could not be attained (Table 7).

TABLE 5

Data recorded from incorporation reaction of SUMO-TdT at 37° C. Incorporation reaction includes 200 nM FAM oligo and varying concentrations of dCTP. Samples were analyzed on TBE-Urea gel.

| dCTP conc. added (µM) | Band Percentage (%) | Band Percentage | FAM oligo amt. (nM) | No. of incorporations | Bandwise Turnover (nM) | Total Turnover (nM) | Total Turnover (µM) | Time taken (s) | Enzyme activity rate (µM dCTP/s) |
|---|---|---|---|---|---|---|---|---|---|
| 0 | 100 | 1 | 200 | 0 | 0 | 0 | 0 | 15 | 0 |
| 1 | 1.7 | 0.017 | 3.4 | 3 | 10.2 | 134.2 | 0.1342 | 15 | 0.00895 |
|  | 11.7 | 0.117 | 23.4 | 2 | 46.8 |  |  |  |  |
|  | 38.6 | 0.386 | 77.2 | 1 | 77.2 |  |  |  |  |
|  | 48 | 0.48 | 96 | 0 | 0 |  |  |  |  |
| 5 | 2.6 | 0.026 | 5.2 | 4 | 20.8 | 262.8 | 0.2628 | 15 | 0.01752 |
|  | 8.4 | 0.084 | 16.8 | 3 | 50.4 |  |  |  |  |
|  | 29.1 | 0.291 | 58.2 | 2 | 116.4 |  |  |  |  |
|  | 37.6 | 0.376 | 75.2 | 1 | 75.2 |  |  |  |  |
|  | 22.3 | 0.223 | 44.6 | 0 | 0 |  |  |  |  |
| 10 | 5.8 | 0.058 | 11.6 | 6 | 69.6 | 469.2 | 0.4692 | 15 | 0.03128 |
|  | 6.1 | 0.061 | 12.2 | 5 | 61 |  |  |  |  |
|  | 9.7 | 0.097 | 19.4 | 4 | 77.6 |  |  |  |  |
|  | 15.2 | 0.152 | 30.4 | 3 | 91.2 |  |  |  |  |
|  | 31.9 | 0.319 | 63.8 | 2 | 127.6 |  |  |  |  |
|  | 21.1 | 0.211 | 42.2 | 1 | 42.2 |  |  |  |  |
|  | 10.2 | 0.102 | 20.4 | 0 | 0 |  |  |  |  |
| 25 | 5.4 | 0.054 | 10.8 | 6 | 64.8 | 573 | 0.573 | 15 | 0.03820 |
|  | 15.3 | 0.153 | 30.6 | 5 | 153 |  |  |  |  |
|  | 15.3 | 0.153 | 30.6 | 4 | 122.4 |  |  |  |  |
|  | 16.8 | 0.168 | 33.6 | 3 | 100.8 |  |  |  |  |
|  | 27.7 | 0.277 | 55.4 | 2 | 110.8 |  |  |  |  |
|  | 10.6 | 0.106 | 21.2 | 1 | 21.2 |  |  |  |  |
|  | 8.9 | 0.089 | 17.8 | 0 | 0 |  |  |  |  |
| 75 | 11.8 | 0.118 | 23.6 | 9 | 212.4 | 1049.4 | 1.0494 | 15 | 0.06996 |
|  | 11.2 | 0.112 | 22.4 | 8 | 179.2 |  |  |  |  |
|  | 10.4 | 0.104 | 20.8 | 7 | 145.6 |  |  |  |  |
|  | 14.7 | 0.147 | 29.4 | 6 | 176.4 |  |  |  |  |
|  | 16.7 | 0.167 | 33.4 | 5 | 167 |  |  |  |  |
|  | 8.5 | 0.085 | 17 | 4 | 68 |  |  |  |  |
|  | 10.9 | 0.109 | 21.8 | 3 | 65.4 |  |  |  |  |
|  | 6.5 | 0.065 | 13 | 2 | 26 |  |  |  |  |
|  | 4.7 | 0.047 | 9.4 | 1 | 9.4 |  |  |  |  |
|  | 4.6 | 0.046 | 9.2 | 0 | 0 |  |  |  |  |
| 100 | 10.7 | 0.107 | 21.4 | 9 | 192.6 | 924.4 | 0.9244 | 15 | 0.06163 |
|  | 7.2 | 0.072 | 14.4 | 8 | 115.2 |  |  |  |  |
|  | 6.8 | 0.068 | 13.6 | 7 | 95.2 |  |  |  |  |
|  | 12.1 | 0.121 | 24.2 | 6 | 145.2 |  |  |  |  |
|  | 14 | 0.14 | 28 | 5 | 140 |  |  |  |  |
|  | 7.3 | 0.073 | 14.6 | 4 | 58.4 |  |  |  |  |
|  | 21.5 | 0.215 | 43 | 3 | 129 |  |  |  |  |
|  | 8.8 | 0.088 | 17.6 | 2 | 35.2 |  |  |  |  |
|  | 6.8 | 0.068 | 13.6 | 1 | 13.6 |  |  |  |  |
|  | 4.8 | 0.048 | 9.6 | 0 | 0 |  |  |  |  |

TABLE 6

Data recorded from incorporation reaction of TdT3-2 at 37° C.
Incorporation reaction included 200 nM FAM oligo and varying
concentrations of dCTP. Samples were analyzed on TBE-Urea gel.

| dCTP conc. added (µM) | Band Percentage (%) | Band Percentage | FAM oligo amt. (nM) | No. of incorporations | Bandwise Turnover (nM) | Total Turnover (nM) | Total Turnover (µM) | Time taken (s) | Enzyme activity rate (µM dCTP/s) |
|---|---|---|---|---|---|---|---|---|---|
| 0 | 100 | 1 | 200 | 0 | 0 | 0 | 0 | 15 | 0 |
| 1 | 0.9 | 0.009 | 1.8 | 3 | 5.4 | 102.4 | 0.1024 | 15 | 0.00683 |
|   | 12.7 | 0.127 | 25.4 | 2 | 50.8 |   |   |   |   |
|   | 23.1 | 0.231 | 46.2 | 1 | 46.2 |   |   |   |   |
|   | 63.3 | 0.633 | 126.6 | 0 | 0 |   |   |   |   |
| 5 | 6.1 | 0.061 | 12.2 | 7 | 85.4 | 487.8 | 0.4878 | 15 | 0.03252 |
|   | 5.3 | 0.053 | 10.6 | 6 | 63.6 |   |   |   |   |
|   | 7.1 | 0.071 | 14.2 | 5 | 71 |   |   |   |   |
|   | 8.5 | 0.085 | 17 | 4 | 68 |   |   |   |   |
|   | 12.4 | 0.124 | 24.8 | 3 | 74.4 |   |   |   |   |
|   | 23.4 | 0.234 | 46.8 | 2 | 93.6 |   |   |   |   |
|   | 15.9 | 0.159 | 31.8 | 1 | 31.8 |   |   |   |   |
|   | 21.3 | 0.213 | 42.6 | 0 | 0 |   |   |   |   |
| 10 | 4.1 | 0.041 | 8.2 | 12 | 98.4 | 1058.2 | 1.0582 | 15 | 0.07055 |
|   | 5.3 | 0.053 | 10.6 | 11 | 116.6 |   |   |   |   |
|   | 6.6 | 0.066 | 13.2 | 10 | 132 |   |   |   |   |
|   | 6.9 | 0.069 | 13.8 | 9 | 124.2 |   |   |   |   |
|   | 6.7 | 0.067 | 13.4 | 8 | 107.2 |   |   |   |   |
|   | 7.7 | 0.077 | 15.4 | 7 | 107.8 |   |   |   |   |
|   | 8 | 0.08 | 16 | 6 | 96 |   |   |   |   |
|   | 8.7 | 0.087 | 17.4 | 5 | 87 |   |   |   |   |
|   | 8.1 | 0.081 | 16.2 | 4 | 64.8 |   |   |   |   |
|   | 9.4 | 0.094 | 18.8 | 3 | 56.4 |   |   |   |   |
|   | 14.5 | 0.145 | 29 | 2 | 58 |   |   |   |   |
|   | 4.9 | 0.049 | 9.8 | 1 | 9.8 |   |   |   |   |
|   | 9.1 | 0.091 | 18.2 | 0 | 0 |   |   |   |   |
| 25 | 6.1 | 0.061 | 12.2 | 12 | 146.4 | 1076.8 | 1.0768 | 15 | 0.07179 |
|   | 5.4 | 0.054 | 10.8 | 11 | 118.8 |   |   |   |   |
|   | 6.5 | 0.065 | 13 | 10 | 130 |   |   |   |   |
|   | 6.6 | 0.066 | 13.2 | 9 | 118.8 |   |   |   |   |
|   | 6.6 | 0.066 | 13.2 | 8 | 105.6 |   |   |   |   |
|   | 7.3 | 0.073 | 14.6 | 7 | 102.2 |   |   |   |   |
|   | 8.1 | 0.081 | 16.2 | 6 | 97.2 |   |   |   |   |
|   | 8 | 0.08 | 16 | 5 | 80 |   |   |   |   |
|   | 7.2 | 0.072 | 14.4 | 4 | 57.6 |   |   |   |   |
|   | 8 | 0.08 | 16 | 3 | 48 |   |   |   |   |
|   | 14.7 | 0.147 | 29.4 | 2 | 58.8 |   |   |   |   |
|   | 6.7 | 0.067 | 13.4 | 1 | 13.4 |   |   |   |   |
|   | 8.8 | 0.088 | 17.6 | 0 | 0 |   |   |   |   |
| 75 | 15.8 | 0.158 | 31.6 | 13 | 410.8 | 1317 | 1.317 | 15 | 0.08780 |
|   | 8.9 | 0.089 | 17.8 | 12 | 213.6 |   |   |   |   |
|   | 9.7 | 0.097 | 19.4 | 11 | 213.4 |   |   |   |   |
|   | 7.1 | 0.071 | 14.2 | 10 | 142 |   |   |   |   |
|   | 5.2 | 0.052 | 10.4 | 9 | 93.6 |   |   |   |   |
|   | 2.9 | 0.029 | 5.8 | 8 | 46.4 |   |   |   |   |
|   | 1.8 | 0.018 | 3.6 | 7 | 25.2 |   |   |   |   |
|   | 2.1 | 0.021 | 4.2 | 6 | 25.2 |   |   |   |   |
|   | 2 | 0.02 | 4 | 5 | 20 |   |   |   |   |
|   | 2.3 | 0.023 | 4.6 | 4 | 18.4 |   |   |   |   |
|   | 5.7 | 0.057 | 11.4 | 3 | 34.2 |   |   |   |   |
|   | 14.7 | 0.147 | 29.4 | 2 | 58.8 |   |   |   |   |
|   | 7.7 | 0.077 | 15.4 | 1 | 15.4 |   |   |   |   |
|   | 14.1 | 0.141 | 28.2 | 0 | 0 |   |   |   |   |
| 100 | 12.7 | 0.127 | 25.4 | 14 | 355.6 | 1535.6 | 1.5356 | 15 | 0.10237 |
|   | 11.1 | 0.111 | 22.2 | 13 | 288.6 |   |   |   |   |
|   | 10.2 | 0.102 | 20.4 | 12 | 244.8 |   |   |   |   |
|   | 8.5 | 0.085 | 17 | 11 | 187 |   |   |   |   |
|   | 6.9 | 0.069 | 13.8 | 10 | 138 |   |   |   |   |
|   | 5.1 | 0.051 | 10.2 | 9 | 91.8 |   |   |   |   |
|   | 2.3 | 0.023 | 4.6 | 8 | 36.8 |   |   |   |   |
|   | 1.8 | 0.018 | 3.6 | 7 | 25.2 |   |   |   |   |
|   | 2.2 | 0.022 | 4.4 | 6 | 26.4 |   |   |   |   |
|   | 1.7 | 0.017 | 3.4 | 5 | 17 |   |   |   |   |
|   | 2.3 | 0.023 | 4.6 | 4 | 18.4 |   |   |   |   |
|   | 6.6 | 0.066 | 13.2 | 3 | 39.6 |   |   |   |   |
|   | 14.5 | 0.145 | 29 | 2 | 58 |   |   |   |   |
|   | 4.2 | 0.042 | 8.4 | 1 | 8.4 |   |   |   |   |
|   | 9.9 | 0.099 | 19.8 | 0 | 0 |   |   |   |   |

TABLE 7

Kinetic parameters of SUMO-TdT and TdT3-2.

| | SUMO-TdT | | TdT3-2 | |
|---|---|---|---|---|
| | 37° C. | 47° C. | 37° C. | 47° C. |
| $k_{cat}$ (s$^{-1}$) | $(8.93 \pm 0.87) \times 10^{-1}$ | -[a] | $1.20 \pm 0.09$ | $(9.25 \pm 1.23) \times 10^{-2}$ |
| $K_M$ (M) | $(1.76 \pm 0.55) \times 10^{-5}$ | -[a] | $(8.19 \pm 2.50) \times 10^{-6}$ | $(6.46 \pm 3.10) \times 10^{-6}$ |
| $k_{cat}/K_M$ (M$^{-1}$s$^{-1}$) | $5.07 \times 10^{4}$ | $(2.25 \pm 0.28) \times 10^{3}$ | $1.46 \times 10^{5}$ | $(1.43 \pm 0.40) \times 10^{4}$ |

[a] Saturation kinetics could not be attained

TABLE 8

Data recorded from incorporation reaction of SUMO-TdT at 47° C. Incorporation reaction included 200 nM FAM oligo and varying concentrations of dCTP. Samples were analyzed on TBE-Urea gel.

| dCTP conc. added (μM) | Band Percentage (%) | Band Percentage | FAM oligo amt. (nM) | No. of incorporations | Bandwise Turnover (nM) | Total Turnover (nM) | Total Turnover (μM) | Time taken (s) | Enzyme activity rate (μM dCTP/s) |
|---|---|---|---|---|---|---|---|---|---|
| 0 | 100 | 1 | 200 | 0 | 0 | 0 | 0 | 5 | 0 |
| 1 | 3.0 | 0.030 | 5.9 | 1 | 5.9 | 5.9 | 0.0059 | 5 | 0.00119 |
|   | 97.0 | 0.970 | 194.1 | 0 | 0 | | | | |
| 5 | 1.3 | 0.013 | 2.5 | 2 | 5.1 | 17.0 | 0.0170 | 5 | 0.00340 |
|   | 6.0 | 0.060 | 12.0 | 1 | 12.0 | | | | |
|   | 92.8 | 0.928 | 185.5 | 0 | 0 | | | | |
| 10 | 1.7 | 0.017 | 3.5 | 2 | 6.9 | 10.1 | 0.0101 | 5 | 0.00203 |
|   | 1.6 | 0.016 | 3.2 | 1 | 3.2 | | | | |
|   | 96.7 | 0.967 | 193.3 | 0 | 0 | | | | |
| 25 | 9.8 | 0.098 | 19.6 | 2 | 39.2 | 63.0 | 0.0630 | 5 | 0.01260 |
|   | 11.9 | 0.119 | 23.8 | 1 | 23.8 | | | | |
|   | 78.3 | 0.783 | 156.6 | 0 | 0 | | | | |
| 75 | 2.0 | 0.020 | 4.1 | 3 | 12.2 | 105.8 | 0.1058 | 5 | 0.02116 |
|   | 17.4 | 0.174 | 34.8 | 2 | 69.5 | | | | |
|   | 12.0 | 0.120 | 24.1 | 1 | 24.1 | | | | |
|   | 68.6 | 0.686 | 137.1 | 0 | 0 | | | | |
| 100 | 1.2 | 0.012 | 2.3 | 4 | 9.3 | 222.8 | 0.2228 | 5 | 0.04457 |
|   | 4.4 | 0.044 | 8.9 | 3 | 26.7 | | | | |
|   | 29.9 | 0.299 | 59.7 | 2 | 119.5 | | | | |
|   | 33.7 | 0.337 | 67.4 | 1 | 67.4 | | | | |
|   | 30.8 | 0.308 | 61.6 | 0 | 0 | | | | |

TABLE 9

Data recorded from incorporation reaction of TdT3-2 at 47° C. Incorporation reaction included 200 nM FAM oligo and varying concentrations of dCTP. Samples were analyzed on TBE-Urea gel.

| dCTP conc. added (μM) | Band Percentage (%) | Band Percentage | FAM oligo amt. (nM) | No. of incorporations | Bandwise Turnover (nM) | Total Turnover (nM) | Total Turnover (μM) | Time taken (s) | Enzyme activity rate (μM dCTP/s) |
|---|---|---|---|---|---|---|---|---|---|
| 0 | 100 | 1 | 200 | 0 | 0 | 0 | 0 | 5 | 0 |
| 1 | 7.3 | 0.073 | 14.7 | 1 | 14.7 | 14.7 | 0.0147 | 5 | 0.00294 |
|   | 92.7 | 0.927 | 185.3 | 0 | 0.0 | | | | |
| 5 | 5.8 | 0.058 | 11.5 | 2 | 23.1 | 46.1 | 0.0461 | 5 | 0.00921 |
|   | 11.5 | 0.115 | 23.0 | 1 | 23.0 | | | | |
|   | 82.7 | 0.827 | 165.5 | 0 | 0.0 | | | | |
| 10 | 0.4 | 0.004 | 0.8 | 3 | 2.4 | 39.8 | 0.0398 | 5 | 0.00797 |
|   | 6.3 | 0.063 | 12.7 | 2 | 25.3 | | | | |
|   | 6.0 | 0.060 | 12.1 | 1 | 12.1 | | | | |
|   | 87.2 | 0.872 | 174.4 | 0 | 0.0 | | | | |

TABLE 9-continued

Data recorded from incorporation reaction of TdT3-2 at 47° C.
Incorporation reaction included 200 nM FAM oligo and varying
concentrations of dCTP. Samples were analyzed on TBE-Urea gel.

| dCTP conc. added (µM) | Band Percentage (%) | Band Percentage | FAM oligo amt. (nM) | No. of incorporations | Bandwise Turnover (nM) | Total Turnover (nM) | Total Turnover (µM) | Time taken (s) | Enzyme activity rate (µM dCTP/s) |
|---|---|---|---|---|---|---|---|---|---|
| 25 | 1.1 | 0.011 | 2.2 | 4 | 8.7 | 54.1 | 0.0541 | 5 | 0.01081 |
|  | 0.5 | 0.005 | 1.1 | 3 | 3.2 |  |  |  |  |
|  | 7.4 | 0.074 | 14.9 | 2 | 29.7 |  |  |  |  |
|  | 6.2 | 0.062 | 12.5 | 1 | 12.5 |  |  |  |  |
|  | 84.7 | 0.847 | 169.4 | 0 | 0.0 |  |  |  |  |
| 75[a] | 0.4 | 0.004 | 0.9 | 5 | 4.3 | 127.8 | 0.1278 | 5 | 0.02555 |
|  | 2.2 | 0.022 | 4.3 | 4 | 17.4 |  |  |  |  |
|  | 2.5 | 0.025 | 5.0 | 3 | 15.1 |  |  |  |  |
|  | 18.4 | 0.184 | 36.9 | 2 | 73.8 |  |  |  |  |
|  | 8.6 | 0.086 | 17.2 | 1 | 17.2 |  |  |  |  |
|  | 67.8 | 0.678 | 135.7 | 0 | 0.0 |  |  |  |  |
| 100 | 1.0 | 0.010 | 2.0 | 5 | 9.9 | 83.3 | 0.0833 | 5 | 0.01665 |
|  | 0.6 | 0.006 | 1.2 | 4 | 4.7 |  |  |  |  |
|  | 0.6 | 0.006 | 1.1 | 3 | 3.4 |  |  |  |  |
|  | 15.3 | 0.153 | 30.6 | 2 | 61.2 |  |  |  |  |
|  | 2.1 | 0.021 | 4.1 | 1 | 4.1 |  |  |  |  |
|  | 80.5 | 0.805 | 161.0 | 0 | 0.0 |  |  |  |  |

[a]Data eliminated from Michaelis-Menten analysis model fitting to obtain best fit curve.

Figure 13:
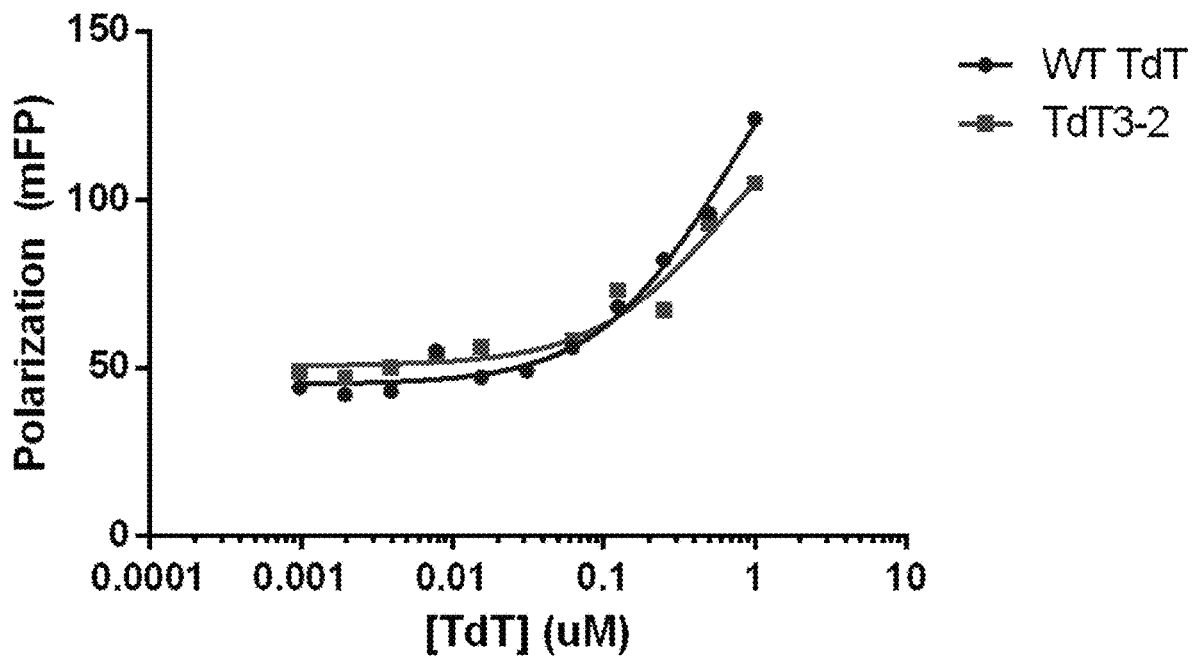
FIG. 13 shows data on binding affinity of SUMO-TdT and TdT3-2 to oligo substrate via fluorescence polarization. Various amounts of SUMO-TdT and TdT3-2 were incubated with 5 nM 5'-FAM-labelled oligo for 10 minutes at 37° C. before reading the polarization on microplate reader.

The conditions were confirmed to be steady-state by estimating the affinity of TdT3-2 to the ssDNA oligo used in the extension reactions. The fluorescence polarization of the FAM-oligo in the presence of a titration of TdT was measured, and the affinities for both our mutant and the SUMO-TdT enzyme were estimated to be greater than 1 µM (FIG. 13). The thermostabilized mutant, TdT3-2, retained the substrate binding affinities and catalytic properties of the SUMO-TdT enzyme, perhaps with slight improvements in activity.

Homology-Based Modelling of TdT3-2

Figure 14:
FIG. 14 is a non-limiting exemplary image showing a predicted protein structure of TdT3-2 using Phyre2 web portal. Amino acid residues in TdT3-2 which are different from SUMO-TdT are highlighted in a darker shading and labelled as displayed. Residues highlighted in a lighter shading (338D, 340D and 428D) corresponds to the residues that binds to divalent metal ions during incorporation reaction. The residues that binds to DNA are on a highlighted alpha helix (residues 253 to 257). Loop1 of TdT3-2 is highlighted (residues 376 to 394).

Murine TdT crystal structure was available (PDB ID 4I27). As TdT3-2 originates from a bovine source, visualizing the location of the mutations on a 3D structure could only be done by homology modelling. Based on available homologous sequence and known structures, Phyre2 server created 3D structure of TdT3-2 from its amino acid query sequence. The location of the eight mutations and other crucial residues could be visualized on the model obtained from Phyre2 (FIG. 14). However, this model could not accurately explain the effects of acquired mutations in TdT3-2 that contributes to its improved thermostability.

CONCLUSION

A thermostable TdT variant would be useful for practical applications such as minimizing presence of secondary structure during oligonucleotide synthesis by increasing the temperature. A thermostable variant from mouse TdT was able to improve the elongation rate of several GC-rich hairpin primer by increasing the temperature during incorporation reaction. The protein engineering method of discovering TdT3-2 in this example allowed the exploration of a wide sequence space. This example shows the value and significance of evolving a thermostable TdT for application in DNA synthesis.

This example establishes an adaptable plate-based FRET assay for screening of mutant libraries using E. coli cell lysate. Three rounds of screening led to the discovery of a significantly more thermostable variant TdT3-2. TdT3-2 was validated on DSC, DSF, SYPRO Orange thermal shift assay and CD and was found to have a $T_m$ about 10° C. higher than SUMO-TdT. In addition, the improvement in thermostability did not occur at the expense of enzymatic activity. TdT3-2 is a better tool for the wide range of applications that currently use SUMO-TdT owing to its improved thermostability and robust activity. Furthermore, TdT3-2 is also an ideal starting point for further engineering, to eventually evolve a TdT capable of efficiently incorporating reversibly blocked nucleotides, which would be especially useful in the nascent fields of de novo gene synthesis and information storage in DNA.

Altogether, these data indicate that the nine amino acid substitutions identified in this example, individually or in any combination, can increase the thermostability of TdT mutants containing the amino acid substitution(s) while preserving the TdT catalytic activities. Furthermore, TdT mutants identified in this example can be thermostable while preserving TdT catalytic activities.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A recombinant terminal deoxynucleotidyl transferase (TdT) comprising an amino acid sequence that is at least 90% identical to SEQ ID NO: 1, wherein the recombinant TdT comprises one or more amino acid substitution mutations at one or more positions corresponding to Glu191, Glu194, Asp242, Lys287, Met299, Thr342, and His421 in the *Bos taurus* TdT of SEQ ID NO: 12.

2. The recombinant TdT of claim 1, wherein the amino acid substitution mutation at the position corresponding to Glu191 in the *Bos taurus* TdT of SEQ ID NO: 12 is Glu191Val.

3. The recombinant TdT of claim 1, wherein the amino acid substitution mutation at the position corresponding to Glu194 in the *Bos taurus* TdT of SEQ ID NO: 12 is Glu194Gly.

4. The recombinant TdT of claim 1, wherein the amino acid substitution mutation at the position corresponding to Asp242 in the *Bos taurus* TdT of SEQ ID NO: 12 is Asp242Tyr.

5. The recombinant TdT of claim 1, wherein the amino acid substitution mutation at the position corresponding to Lys287 in the *Bos taurus* TdT of SEQ ID NO: 12 is Lys287Glu.

6. The recombinant TdT of claim 1, wherein the amino acid substitution mutation at the position corresponding to Met299 in the *Bos taurus* TdT of SEQ ID NO: 12 is Met299Lys.

7. The recombinant TdT of claim 1, wherein the amino acid substitution mutation at the position corresponding to Thr342 in the *Bos taurus* TdT of SEQ ID NO: 12 is Thr342Ser.

8. The recombinant TdT of claim 1, wherein the amino acid substitution mutation at the position corresponding to His421 in the *Bos taurus* TdT of SEQ ID NO: 12 is His421Pro.

9. The recombinant TdT of claim 1, wherein the recombinant TdT comprises two or more amino acid substitution mutations at two or more positions corresponding to Glu191, Lys193, Glu194, Asp242, Lys287, Met299, Thr342, and His421 in the *Bos taurus* TdT of SEQ ID NO: 12.

10. The recombinant TdT of claim 1, wherein the recombinant TdT comprises nine amino acid substitution mutations at positions corresponding to Glu191, Lys193, Glu194, Asp242, Lys287, Phe296, Met299, Thr342, and His421 in the *Bos taurus* TdT of SEQ ID NO: 12.

11. The recombinant TdT of claim 1, wherein the recombinant TdT comprises an amino acid sequence that is at least 95% identical to SEQ ID NO: 11.

12. The recombinant TdT of claim 1, wherein the recombinant TdT comprises an amino acid sequence that is at least 90% identical to SEQ ID NO: 12.

13. The recombinant TdT of claim 1, wherein the recombinant TdT is stable at a temperature of 47° C. or higher.

14. The recombinant TdT of claim 1, wherein the terminal deoxynucleotidyl transferase activity of the recombinant TdT is at least 80%, 85%, 90%, 95%, 100%, 105%, 110%, 115%, or 120%, of the terminal deoxynucleotidyl transferase activity of the *Bos taurus* TdT of SEQ ID NO: 12 at a same test temperature.

15. The recombinant TdT of claim 1, wherein the recombinant TdT comprises a small ubiquitin-like modifier (SUMO) fragment.

16. The recombinant TdT of claim 1, wherein the recombinant TdT comprises the SUMO fragment on the N-terminus of the recombinant TdT.

17. The recombinant TdT of claim 1, wherein the recombinant TdT comprises an amino acid sequence that is at least 95% identical to SEQ ID NO: 1.

18. The recombinant TdT of claim 1, wherein the recombinant TdT comprises an amino acid sequence that is at least 99% identical to SEQ ID NO: 1.

19. The recombinant TdT of claim 1, wherein the recombinant TdT comprises three or more amino acid substitution mutations at three or more positions corresponding to Glu191, Lys193, Glu194, Asp242, Lys287, Phe296, Met299, Thr342, and His421 in the *Bos taurus* TdT of SEQ ID NO: 12.

20. The recombinant TdT of claim 1, wherein the recombinant TdT comprises an amino acid substitution mutation at a position corresponding to Lys193 in the *Bos taurus* TdT of SEQ ID NO: 12.

21. The recombinant TdT of claim 20, wherein the amino acid substitution mutation at the position corresponding to Lys193 in the *Bos taurus* TdT of SEQ ID NO: 12 is Lys193Asn.

22. The recombinant TdT of claim 1, wherein the recombinant TdT comprises an amino acid substitution mutation at a position corresponding to Phe296 in the *Bos taurus* TdT of SEQ ID NO: 12.

23. The recombinant TdT of claim 22, wherein the amino acid substitution mutation at the position corresponding to Phe296 in the *Bos taurus* TdT of SEQ ID NO: 12 is Phe296Leu.

* * * * *

```
                        SEQUENCE LISTING

<160> NUMBER OF SEQ ID NOS: 33

<210> SEQ ID NO 1
<211> LENGTH: 382
<212> TYPE: PRT
<213> ORGANISM: Artificial Sequence
<220> FEATURE:
<223> OTHER INFORMATION: Bos taurus TdT 139-520
<220> FEATURE:
<221> NAME/KEY: NON_TER
<222> LOCATION: (1)..(1)

<400> SEQUENCE: 1

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45
```

Ala Glu Asn Ser Glu Phe Lys Glu Asn Glu Val Ser Tyr Val Thr Phe
 50                  55                  60

Met Arg Ala Ala Ser Val Leu Lys Ser Leu Pro Phe Thr Ile Ile Ser
 65                  70                  75                  80

Met Lys Asp Thr Glu Gly Ile Pro Cys Leu Gly Asp Lys Val Lys Cys
                 85                  90                  95

Ile Ile Glu Glu Ile Ile Glu Asp Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
        275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Glu Ile Phe Ala
        355                 360                 365

His Leu Gly Leu Asp Tyr Ile Glu Pro Trp Glu Arg Asn Ala
370                 375                 380

<210> SEQ ID NO 2
<211> LENGTH: 382
<212> TYPE: PRT
<213> ORGANISM: Artificial Sequence
<220> FEATURE:
<223> OTHER INFORMATION: TdT 139-520 with Glu53Val in TdT
      139-520/Glu191Val in WT
<220> FEATURE:
<221> NAME/KEY: NON_TER
<222> LOCATION: (1)..(1)

<400> SEQUENCE: 2

Arg Thr Asp Tyr Ser Ala Thr Pro Asn Pro Gly Phe Gln Lys Thr Pro
 1               5                  10                  15

Pro Leu Ala Val Lys Lys Ile Ser Gln Tyr Ala Cys Gln Arg Lys Thr
                20                  25                  30

Thr Leu Asn Asn Tyr Asn His Ile Phe Thr Asp Ala Phe Glu Ile Leu
            35                  40                  45

Ala Glu Asn Ser Val Phe Lys Glu Asn Glu Val Ser Tyr Val Thr Phe
 50                  55                  60

Met Arg Ala Ala Ser Val Leu Lys Ser Leu Pro Phe Thr Ile Ile Ser
 65                  70                  75                  80

Met Lys Asp Thr Glu Gly Ile Pro Cys Leu Gly Asp Lys Val Lys Cys
                 85                  90                  95

Ile Ile Glu Glu Ile Ile Glu Asp Gly Glu Ser Ser Val Lys Ala
                100                 105                 110

Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
            195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
            275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Glu Ile Phe Ala
            355                 360                 365

His Leu Gly Leu Asp Tyr Ile Glu Pro Trp Glu Arg Asn Ala
370                 375                 380

<210> SEQ ID NO 3
<211> LENGTH: 382
<212> TYPE: PRT
<213> ORGANISM: Artificial Sequence
<220> FEATURE:
<223> OTHER INFORMATION: TdT 139-520 with Lys55Asn in TdT
      139-520/Lys193Asn in WT
<220> FEATURE:

<221> NAME/KEY: NON_TER
<222> LOCATION: (1)..(1)

<400> SEQUENCE: 3

```
Arg Thr Asp Tyr Ser Ala Thr Pro Asn Pro Gly Phe Gln Lys Thr Pro
  1               5                  10                  15

Pro Leu Ala Val Lys Lys Ile Ser Gln Tyr Ala Cys Gln Arg Lys Thr
             20                  25                  30

Thr Leu Asn Asn Tyr Asn His Ile Phe Thr Asp Ala Phe Glu Ile Leu
         35                  40                  45

Ala Glu Asn Ser Glu Phe Asn Glu Asn Glu Val Ser Tyr Val Thr Phe
     50                  55                  60

Met Arg Ala Ala Ser Val Leu Lys Ser Leu Pro Phe Thr Ile Ile Ser
 65                  70                  75                  80

Met Lys Asp Thr Glu Gly Ile Pro Cys Leu Gly Asp Lys Val Lys Cys
                 85                  90                  95

Ile Ile Glu Glu Ile Ile Glu Asp Gly Glu Ser Ser Glu Val Lys Ala
                100                 105                 110

Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
        275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Ile Phe Ala
        355                 360                 365

His Leu Gly Leu Asp Tyr Ile Glu Pro Trp Glu Arg Asn Ala
370                 375                 380
```

<210> SEQ ID NO 4

```
<211> LENGTH: 382
<212> TYPE: PRT
<213> ORGANISM: Artificial Sequence
<220> FEATURE:
<223> OTHER INFORMATION: TdT 139-520 with Glu56Gly in TdT
      139-520/Glu194Gly in WT TdT
<220> FEATURE:
<221> NAME/KEY: NON_TER
<222> LOCATION: (1)..(1)

<400> SEQUENCE: 4

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45

Ala Glu Asn Ser Glu Phe Lys Gly Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
    130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
    210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
        275                 280                 285

Ser Ser Lys Ser Asn Gln Gln Glu Gly Lys Thr Trp Lys Ala Ile Arg
    290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Glu Ile Phe Ala
```

```
                355                 360                 365
His Leu Gly Leu Asp Tyr Ile Glu Pro Trp Glu Arg Asn Ala
    370                 375                 380

<210> SEQ ID NO 5
<211> LENGTH: 382
<212> TYPE: PRT
<213> ORGANISM: Artificial Sequence
<220> FEATURE:
<223> OTHER INFORMATION: TdT 139-520 with Asp104Tyr in TdT
      139-520/Asp242Tyr in WT TdT
<220> FEATURE:
<221> NAME/KEY: NON_TER
<222> LOCATION: (1)..(1)

<400> SEQUENCE: 5

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45

Ala Glu Asn Ser Glu Phe Lys Glu Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Tyr Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
    130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
    210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
        275                 280                 285

Ser Ser Lys Ser Asn Gln Gln Glu Gly Lys Thr Trp Lys Ala Ile Arg
    290                 295                 300

Val Asp Leu Val Met Cys Pro Tyr Glu Asn Arg Ala Phe Ala Leu Leu
305                 310                 315                 320
```

```
Gly Trp Thr Gly Ser Arg Gln Phe Glu Arg Asp Ile Arg Arg Tyr Ala
            325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Ile Phe Ala
            355                 360                 365

His Leu Gly Leu Asp Tyr Ile Glu Pro Trp Glu Arg Asn Ala
            370                 375                 380

<210> SEQ ID NO 6
<211> LENGTH: 382
<212> TYPE: PRT
<213> ORGANISM: Artificial Sequence
<220> FEATURE:
<223> OTHER INFORMATION: TdT 139-520 with Lys149Glu in TdT
      139-520/Lys287Glu in WT TdT
<220> FEATURE:
<221> NAME/KEY: NON_TER
<222> LOCATION: (1)..(1)

<400> SEQUENCE: 6

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45

Ala Glu Asn Ser Glu Phe Lys Glu Asn Glu Val Ser Tyr Val Thr Phe
    50                  55                  60

Met Arg Ala Ala Ser Val Leu Lys Ser Leu Pro Phe Thr Ile Ile Ser
65              70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
130                 135                 140

Arg Ser Leu Ser Glu Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
    210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
        275                 280                 285
```

```
Ser Ser Lys Ser Asn Gln Gln Glu Gly Lys Thr Trp Lys Ala Ile Arg
    290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
                340                 345                 350

Thr Lys Arg Val Phe Leu Lys Ala Glu Ser Glu Glu Glu Ile Phe Ala
            355                 360                 365

His Leu Gly Leu Asp Tyr Ile Glu Pro Trp Glu Arg Asn Ala
        370                 375                 380

<210> SEQ ID NO 7
<211> LENGTH: 382
<212> TYPE: PRT
<213> ORGANISM: Artificial Sequence
<220> FEATURE:
<223> OTHER INFORMATION: TdT 139-520 with Phe158Leu in TdT
      139-520/Phe296Leu in WT TdT.
<220> FEATURE:
<221> NAME/KEY: NON_TER
<222> LOCATION: (1)..(1)

<400> SEQUENCE: 7

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
                20                  25                  30

Thr Leu Asn Asn Tyr Asn His Ile Phe Thr Asp Ala Phe Glu Ile Leu
            35                  40                  45

Ala Glu Asn Ser Glu Phe Lys Glu Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
                100                 105                 110

Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
    130                 135                 140

Arg Ser Leu Ser Lys Ile Met Ser Asp Lys Thr Leu Lys Leu Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
    195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
```

```
                        245                 250                 255
Phe Glu Lys Phe Lys Leu Pro Ser Arg Gln Val Asp Thr Leu Asp His
            260                 265                 270
Phe Gln Lys Cys Phe Leu Ile Leu Lys Leu His His Gln Arg Val Asp
            275                 280                 285
Ser Ser Lys Ser Asn Gln Gln Glu Gly Lys Thr Trp Lys Ala Ile Arg
            290                 295                 300
Val Asp Leu Val Met Cys Pro Tyr Glu Asn Arg Ala Phe Ala Leu Leu
305                 310                 315                 320
Gly Trp Thr Gly Ser Arg Gln Phe Glu Arg Asp Ile Arg Arg Tyr Ala
            325                 330                 335
Thr His Glu Arg Lys Met Met Leu Asp Asn His Ala Leu Tyr Asp Lys
            340                 345                 350
Thr Lys Arg Val Phe Leu Lys Ala Glu Ser Glu Glu Ile Phe Ala
            355                 360                 365
His Leu Gly Leu Asp Tyr Ile Glu Pro Trp Glu Arg Asn Ala
            370                 375                 380

<210> SEQ ID NO 8
<211> LENGTH: 382
<212> TYPE: PRT
<213> ORGANISM: Artificial Sequence
<220> FEATURE:
<223> OTHER INFORMATION: TdT 139-520 with Met161Lys in TdT
      139-520/Met299Lys in WT TdT
<220> FEATURE:
<221> NAME/KEY: NON_TER
<222> LOCATION: (1)..(1)

<400> SEQUENCE: 8

Arg Thr Asp Tyr Ser Ala Thr Pro Asn Pro Gly Phe Gln Lys Thr Pro
1               5                   10                  15
Pro Leu Ala Val Lys Lys Ile Ser Gln Tyr Ala Cys Gln Arg Lys Thr
            20                  25                  30
Thr Leu Asn Asn Tyr Asn His Ile Phe Thr Asp Ala Phe Glu Ile Leu
            35                  40                  45
Ala Glu Asn Ser Glu Phe Lys Glu Asn Glu Val Ser Tyr Val Thr Phe
        50                  55                  60
Met Arg Ala Ala Ser Val Leu Lys Ser Leu Pro Phe Thr Ile Ile Ser
65                  70                  75                  80
Met Lys Asp Thr Glu Gly Ile Pro Cys Leu Gly Asp Lys Val Lys Cys
                85                  90                  95
Ile Ile Glu Glu Ile Ile Glu Asp Gly Glu Ser Ser Glu Val Lys Ala
            100                 105                 110
Val Leu Asn Asp Glu Arg Tyr Gln Ser Phe Lys Leu Phe Thr Ser Val
            115                 120                 125
Phe Gly Val Gly Leu Lys Thr Ser Glu Lys Trp Phe Arg Met Gly Phe
    130                 135                 140
Arg Ser Leu Ser Lys Ile Met Ser Asp Lys Thr Leu Lys Phe Thr Lys
145                 150                 155                 160
Lys Gln Lys Ala Gly Phe Leu Tyr Tyr Glu Asp Leu Val Ser Cys Val
                165                 170                 175
Thr Arg Ala Glu Ala Glu Ala Val Gly Val Leu Val Lys Glu Ala Val
            180                 185                 190
Trp Ala Phe Leu Pro Asp Ala Phe Val Thr Met Thr Gly Gly Phe Arg
            195                 200                 205
```

```
Arg Gly Lys Lys Ile Gly His Asp Val Asp Phe Leu Ile Thr Ser Pro
    210                 215                 220
Gly Ser Ala Glu Asp Glu Glu Gln Leu Leu Pro Lys Val Ile Asn Leu
225                 230                 235                 240
Trp Glu Lys Lys Gly Leu Leu Leu Tyr Tyr Asp Leu Val Glu Ser Thr
                245                 250                 255
Phe Glu Lys Phe Lys Leu Pro Ser Arg Gln Val Asp Thr Leu Asp His
            260                 265                 270
Phe Gln Lys Cys Phe Leu Ile Leu Lys Leu His His Gln Arg Val Asp
        275                 280                 285
Ser Ser Lys Ser Asn Gln Gln Glu Gly Lys Thr Trp Lys Ala Ile Arg
290                 295                 300
Val Asp Leu Val Met Cys Pro Tyr Glu Asn Arg Ala Phe Ala Leu Leu
305                 310                 315                 320
Gly Trp Thr Gly Ser Arg Gln Phe Glu Arg Asp Ile Arg Arg Tyr Ala
                325                 330                 335
Thr His Glu Arg Lys Met Met Leu Asp Asn His Ala Leu Tyr Asp Lys
            340                 345                 350
Thr Lys Arg Val Phe Leu Lys Ala Glu Ser Glu Glu Ile Phe Ala
        355                 360                 365
His Leu Gly Leu Asp Tyr Ile Glu Pro Trp Glu Arg Asn Ala
370                 375                 380

<210> SEQ ID NO 9
<211> LENGTH: 382
<212> TYPE: PRT
<213> ORGANISM: Artificial Sequence
<220> FEATURE:
<223> OTHER INFORMATION: TdT 139-520 with Thr204Ser in TdT
      139-520/Thr342Ser in WT TdT
<220> FEATURE:
<221> NAME/KEY: NON_TER
<222> LOCATION: (1)..(1)

<400> SEQUENCE: 9

Arg Thr Asp Tyr Ser Ala Thr Pro Asn Pro Gly Phe Gln Lys Thr Pro
1               5                   10                  15
Pro Leu Ala Val Lys Lys Ile Ser Gln Tyr Ala Cys Gln Arg Lys Thr
                20                  25                  30
Thr Leu Asn Asn Tyr Asn His Ile Phe Thr Asp Ala Phe Glu Ile Leu
            35                  40                  45
Ala Glu Asn Ser Glu Phe Lys Glu Asn Glu Val Ser Tyr Val Thr Phe
50                  55                  60
Met Arg Ala Ala Ser Val Leu Lys Ser Leu Pro Phe Thr Ile Ile Ser
65                  70                  75                  80
Met Lys Asp Thr Glu Gly Ile Pro Cys Leu Gly Asp Lys Val Lys Cys
                85                  90                  95
Ile Ile Glu Glu Ile Ile Glu Asp Gly Glu Ser Ser Glu Val Lys Ala
            100                 105                 110
Val Leu Asn Asp Glu Arg Tyr Gln Ser Phe Lys Leu Phe Thr Ser Val
        115                 120                 125
Phe Gly Val Gly Leu Lys Thr Ser Glu Lys Trp Phe Arg Met Gly Phe
    130                 135                 140
Arg Ser Leu Ser Lys Ile Met Ser Asp Lys Thr Leu Lys Phe Thr Lys
145                 150                 155                 160
Met Gln Lys Ala Gly Phe Leu Tyr Tyr Glu Asp Leu Val Ser Cys Val
                165                 170                 175
```

```
Thr Arg Ala Glu Ala Glu Ala Val Gly Val Leu Val Lys Glu Ala Val
            180                 185                 190

Trp Ala Phe Leu Pro Asp Ala Phe Val Thr Met Ser Gly Gly Phe Arg
            195                 200                 205

Arg Gly Lys Lys Ile Gly His Asp Val Asp Phe Leu Ile Thr Ser Pro
            210                 215                 220

Gly Ser Ala Glu Asp Glu Glu Gln Leu Leu Pro Lys Val Ile Asn Leu
225                 230                 235                 240

Trp Glu Lys Lys Gly Leu Leu Tyr Tyr Asp Leu Val Glu Ser Thr
            245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
            275                 280                 285

Ser Ser Lys Ser Asn Gln Gln Glu Gly Lys Thr Trp Lys Ala Ile Arg
            290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
            325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Ile Phe Ala
            355                 360                 365

His Leu Gly Leu Asp Tyr Ile Glu Pro Trp Glu Arg Asn Ala
            370                 375                 380

<210> SEQ ID NO 10
<211> LENGTH: 382
<212> TYPE: PRT
<213> ORGANISM: Artificial Sequence
<220> FEATURE:
<223> OTHER INFORMATION: TdT 139-520 with His283Pro in TdT
      139-520/His421Pro in WT TdT
<220> FEATURE:
<221> NAME/KEY: NON_TER
<222> LOCATION: (1)..(1)

<400> SEQUENCE: 10

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45

Ala Glu Asn Ser Glu Phe Lys Glu Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
```

```
            130                 135                 140
Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
                180                 185                 190

Trp Ala Phe Leu Pro Asp Ala Phe Val Thr Met Thr Gly Gly Phe Arg
                195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
                260                 265                 270

Phe Gln Lys Cys Phe Leu Ile Leu Lys Leu Pro His Gln Arg Val Asp
                275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
                340                 345                 350

Thr Lys Arg Val Phe Leu Lys Ala Glu Ser Glu Glu Ile Phe Ala
                355                 360                 365

His Leu Gly Leu Asp Tyr Ile Glu Pro Trp Glu Arg Asn Ala
370                 375                 380

<210> SEQ ID NO 11
<211> LENGTH: 382
<212> TYPE: PRT
<213> ORGANISM: Artificial Sequence
<220> FEATURE:
<223> OTHER INFORMATION: TdT 139-520 with TdT3-2 Substitution Mutations
<220> FEATURE:
<221> NAME/KEY: NON_TER
<222> LOCATION: (1)..(1)

<400> SEQUENCE: 11

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
                20                  25                  30

Thr Leu Asn Asn Tyr Asn His Ile Phe Thr Asp Ala Phe Glu Ile Leu
                35                  40                  45

Ala Glu Asn Ser Val Phe Asn Gly Asn Glu Val Ser Tyr Val Thr Phe
                50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Tyr Gly Glu Ser Ser Glu Val Lys Ala
```

```
                100                 105                 110
Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
            130                 135                 140

Arg Ser Leu Ser Glu Ile Met Ser Asp Lys Thr Leu Lys Leu Thr Lys
145                 150                 155                 160

Lys Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
            195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu Pro His Gln Arg Val Asp
            275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Ile Phe Ala
            355                 360                 365

His Leu Gly Leu Asp Tyr Ile Glu Pro Trp Glu Arg Asn Ala
        370                 375                 380

<210> SEQ ID NO 12
<211> LENGTH: 520
<212> TYPE: PRT
<213> ORGANISM: Bos taurus

<400> SEQUENCE: 12

Met Ala Gln Gln Arg Gln His Gln Arg Leu Pro Met Asp Pro Leu Cys
1               5                   10                  15

Thr Ala Ser Ser Gly Pro Arg Lys Lys Arg Pro Arg Gln Val Gly Ala
            20                  25                  30

Ser Met Ala Ser Pro Pro His Asp Ile Lys Phe Gln Asn Leu Val Leu
        35                  40                  45

Phe Ile Leu Glu Lys Lys Met Gly Thr Thr Arg Arg Asn Phe Leu Met
    50                  55                  60

Glu Leu Ala Arg Arg Lys Gly Phe Arg Val Glu Asn Glu Leu Ser Asp
65                  70                  75                  80

Ser Val Thr His Ile Val Ala Glu Asn Asn Ser Gly Ser Glu Val Leu
                85                  90                  95
```

-continued

Glu Trp Leu Gln Val Gln Asn Ile Arg Ala Ser Ser Gln Leu Glu Leu
            100                 105                 110

Leu Asp Val Ser Trp Leu Ile Glu Ser Met Gly Ala Gly Lys Pro Val
            115                 120                 125

Glu Ile Thr Gly Lys His Gln Leu Val Val Arg Thr Asp Tyr Ser Ala
            130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
            165                 170                 175

His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
            195                 200                 205

Leu Lys Ser Leu Pro Phe Thr Ile Ile Ser Met Lys Asp Thr Glu Gly
            210                 215                 220

Ile Pro Cys Leu Gly Asp Lys Val Lys Cys Ile Ile Glu Glu Ile Ile
225                 230                 235                 240

Glu Asp Gly Glu Ser Ser Glu Val Lys Ala Val Leu Asn Asp Glu Arg
            245                 250                 255

Tyr Gln Ser Phe Lys Leu Phe Thr Ser Val Phe Gly Val Gly Leu Lys
            260                 265                 270

Thr Ser Glu Lys Trp Phe Arg Met Gly Phe Arg Ser Leu Ser Lys Ile
            275                 280                 285

Met Ser Asp Lys Thr Leu Lys Phe Thr Lys Met Gln Lys Ala Gly Phe
290                 295                 300

Leu Tyr Tyr Glu Asp Leu Val Ser Cys Val Thr Arg Ala Glu Ala Glu
305                 310                 315                 320

Ala Val Gly Val Leu Val Lys Glu Ala Val Trp Ala Phe Leu Pro Asp
            325                 330                 335

Ala Phe Val Thr Met Thr Gly Gly Phe Arg Arg Gly Lys Lys Ile Gly
            340                 345                 350

His Asp Val Asp Phe Leu Ile Thr Ser Pro Gly Ser Ala Glu Asp Glu
            355                 360                 365

Glu Gln Leu Leu Pro Lys Val Ile Asn Leu Trp Glu Lys Lys Gly Leu
            370                 375                 380

Leu Leu Tyr Tyr Asp Leu Val Glu Ser Thr Phe Glu Lys Phe Lys Leu
385                 390                 395                 400

Pro Ser Arg Gln Val Asp Thr Leu Asp His Phe Gln Lys Cys Phe Leu
            405                 410                 415

Ile Leu Lys Leu His His Gln Arg Val Asp Ser Ser Lys Ser Asn Gln
            420                 425                 430

Gln Glu Gly Lys Thr Trp Lys Ala Ile Arg Val Asp Leu Val Met Cys
            435                 440                 445

Pro Tyr Glu Asn Arg Ala Phe Ala Leu Leu Gly Trp Thr Gly Ser Arg
450                 455                 460

Gln Phe Glu Arg Asp Ile Arg Arg Tyr Ala Thr His Glu Arg Lys Met
465                 470                 475                 480

Met Leu Asp Asn His Ala Leu Tyr Asp Lys Thr Lys Arg Val Phe Leu
            485                 490                 495

Lys Ala Glu Ser Glu Glu Glu Ile Phe Ala His Leu Gly Leu Asp Tyr
            500                 505                 510

Ile Glu Pro Trp Glu Arg Asn Ala

<210> SEQ ID NO 13
<211> LENGTH: 98
<212> TYPE: PRT
<213> ORGANISM: Artificial Sequence
<220> FEATURE:
<223> OTHER INFORMATION: Saccharomyces cerevisiae SUMO 1-98
<220> FEATURE:
<221> NAME/KEY: NON_TER
<222> LOCATION: (98)..(98)

<400> SEQUENCE: 13

```
Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly
```

<210> SEQ ID NO 14
<211> LENGTH: 504
<212> TYPE: PRT
<213> ORGANISM: Artificial Sequence
<220> FEATURE:
<223> OTHER INFORMATION: HIS-SUMO-TdT 139-520

<400> SEQUENCE: 14

```
Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Glu Leu Met Arg Thr Asp Tyr Ser Ala
        115                 120                 125

Thr Pro Asn Pro Gly Phe Gln Lys Thr Pro Pro Leu Ala Val Lys Lys
    130                 135                 140

Ile Ser Gln Tyr Ala Cys Gln Arg Lys Thr Thr Leu Asn Asn Tyr Asn
145                 150                 155                 160

His Ile Phe Thr Asp Ala Phe Glu Ile Leu Ala Glu Asn Ser Glu Phe
                165                 170                 175

Lys Glu Asn Glu Val Ser Tyr Val Thr Phe Met Arg Ala Ala Ser Val
```

```
            180                 185                 190
Leu Lys Ser Leu Pro Phe Thr Ile Ser Met Lys Asp Thr Glu Gly
            195                 200                 205

Ile Pro Cys Leu Gly Asp Lys Val Lys Cys Ile Ile Glu Ile Ile
210                 215                 220

Glu Asp Gly Glu Ser Ser Glu Val Lys Ala Val Leu Asn Asp Glu Arg
225                 230                 235                 240

Tyr Gln Ser Phe Lys Leu Phe Thr Ser Val Phe Gly Val Gly Leu Lys
                245                 250                 255

Thr Ser Glu Lys Trp Phe Arg Met Gly Phe Arg Ser Leu Ser Lys Ile
            260                 265                 270

Met Ser Asp Lys Thr Leu Lys Phe Thr Lys Met Gln Lys Ala Gly Phe
        275                 280                 285

Leu Tyr Tyr Glu Asp Leu Val Ser Cys Val Thr Arg Ala Glu Ala Glu
    290                 295                 300

Ala Val Gly Val Leu Val Lys Glu Ala Val Trp Ala Phe Leu Pro Asp
305                 310                 315                 320

Ala Phe Val Thr Met Thr Gly Gly Phe Arg Arg Gly Lys Lys Ile Gly
                325                 330                 335

His Asp Val Asp Phe Leu Ile Thr Ser Pro Gly Ser Ala Glu Asp Glu
                340                 345                 350

Glu Gln Leu Leu Pro Lys Val Ile Asn Leu Trp Glu Lys Lys Gly Leu
            355                 360                 365

Leu Leu Tyr Tyr Asp Leu Val Glu Ser Thr Phe Glu Lys Phe Lys Leu
        370                 375                 380

Pro Ser Arg Gln Val Asp Thr Leu Asp His Phe Gln Lys Cys Phe Leu
385                 390                 395                 400

Ile Leu Lys Leu His His Gln Arg Val Asp Ser Ser Lys Ser Asn Gln
                405                 410                 415

Gln Glu Gly Lys Thr Trp Lys Ala Ile Arg Val Asp Leu Val Met Cys
            420                 425                 430

Pro Tyr Glu Asn Arg Ala Phe Ala Leu Leu Gly Trp Thr Gly Ser Arg
        435                 440                 445

Gln Phe Glu Arg Asp Ile Arg Arg Tyr Ala Thr His Glu Arg Lys Met
    450                 455                 460

Met Leu Asp Asn His Ala Leu Tyr Asp Lys Thr Lys Arg Val Phe Leu
465                 470                 475                 480

Lys Ala Glu Ser Glu Glu Glu Ile Phe Ala His Leu Gly Leu Asp Tyr
                485                 490                 495

Ile Glu Pro Trp Glu Arg Asn Ala
            500

<210> SEQ ID NO 15
<211> LENGTH: 504
<212> TYPE: PRT
<213> ORGANISM: Artificial Sequence
<220> FEATURE:
<223> OTHER INFORMATION: TdT3-2

<400> SEQUENCE: 15

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
```

```
                35                  40                  45
Val Ser Asp Gly Ser Ser Glu Ile Phe Phe Lys Ile Lys Thr Thr
 50                  55                  60

Pro Leu Arg Arg Leu Met Glu Ala Phe Ala Lys Arg Gln Gly Lys Glu
 65                  70                  75                  80

Met Asp Ser Leu Arg Phe Leu Tyr Asp Gly Ile Arg Ile Gln Ala Asp
                 85                  90                  95

Gln Thr Pro Glu Asp Leu Asp Met Glu Asp Asn Asp Ile Ile Glu Ala
                100                 105                 110

His Arg Glu Gln Ile Gly Gly Glu Leu Met Arg Thr Asp Tyr Ser Ala
                115                 120                 125

Thr Pro Asn Pro Gly Phe Gln Lys Thr Pro Leu Ala Val Lys Lys
130                 135                 140

Ile Ser Gln Tyr Ala Cys Gln Arg Lys Thr Thr Leu Asn Asn Tyr Asn
145                 150                 155                 160

His Ile Phe Thr Asp Ala Phe Glu Ile Leu Ala Glu Asn Ser Val Phe
                165                 170                 175

Asn Gly Asn Glu Val Ser Tyr Val Thr Phe Met Arg Ala Ala Ser Val
                180                 185                 190

Leu Lys Ser Leu Pro Phe Thr Ile Ser Met Lys Asp Thr Glu Gly
                195                 200                 205

Ile Pro Cys Leu Gly Asp Lys Val Lys Cys Ile Ile Glu Glu Ile Ile
210                 215                 220

Glu Tyr Gly Glu Ser Ser Glu Val Lys Ala Val Leu Asn Asp Glu Arg
225                 230                 235                 240

Tyr Gln Ser Phe Lys Leu Phe Thr Ser Val Phe Gly Val Gly Leu Lys
                245                 250                 255

Thr Ser Glu Lys Trp Phe Arg Met Gly Phe Arg Ser Leu Ser Glu Ile
                260                 265                 270

Met Ser Asp Lys Thr Leu Lys Leu Thr Lys Lys Gln Lys Ala Gly Phe
                275                 280                 285

Leu Tyr Tyr Glu Asp Leu Val Ser Cys Val Thr Arg Ala Glu Ala Glu
290                 295                 300

Ala Val Gly Val Leu Val Lys Glu Ala Val Trp Ala Phe Leu Pro Asp
305                 310                 315                 320

Ala Phe Val Thr Met Thr Gly Gly Phe Arg Arg Gly Lys Lys Ile Gly
                325                 330                 335

His Asp Val Asp Phe Leu Ile Thr Ser Pro Gly Ser Ala Glu Asp Glu
                340                 345                 350

Glu Gln Leu Leu Pro Lys Val Ile Asn Leu Trp Glu Lys Lys Gly Leu
                355                 360                 365

Leu Leu Tyr Tyr Asp Leu Val Glu Ser Thr Phe Glu Lys Phe Lys Leu
                370                 375                 380

Pro Ser Arg Gln Val Asp Thr Leu Asp His Phe Gln Lys Cys Phe Leu
385                 390                 395                 400

Ile Leu Lys Leu Pro His Gln Arg Val Asp Ser Ser Lys Ser Asn Gln
                405                 410                 415

Gln Glu Gly Lys Thr Trp Lys Ala Ile Arg Val Asp Leu Val Met Cys
                420                 425                 430

Pro Tyr Glu Asn Arg Ala Phe Ala Leu Leu Gly Trp Thr Gly Ser Arg
                435                 440                 445

Gln Phe Glu Arg Asp Ile Arg Arg Tyr Ala Thr His Glu Arg Lys Met
                450                 455                 460
```

```
Met Leu Asp Asn His Ala Leu Tyr Asp Lys Thr Lys Arg Val Phe Leu
465                 470                 475                 480

Lys Ala Glu Ser Glu Glu Ile Phe Ala His Leu Gly Leu Asp Tyr
            485                 490                 495

Ile Glu Pro Trp Glu Arg Asn Ala
            500
```

```
<210> SEQ ID NO 16
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (19)..(19)
<223> OTHER INFORMATION: Fluorescein T

<400> SEQUENCE: 16
cgcttgcaca ggtgcgtttc a                                          21

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_difference
<222> LOCATION: (1)..(1)
<223> OTHER INFORMATION: 5' 6-Fluorescein

<400> SEQUENCE: 17
cgcttgcaca ggtgcgttcg                                            20

<210> SEQ ID NO 18
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 18
aaaaaacacc tgcggcctgg tgccgcgcgg cagcgctagc atg                  43

<210> SEQ ID NO 19
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 19
aaaaaacacc tgcgggatcc ggtaccgcgg ccgccta                         37

<210> SEQ ID NO 20
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 20
attctgtgtt taawgraaat gaagtctctt atgtg                           35
```

```
<210> SEQ ID NO 21
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 21
agatctctga gtraaataat gtcagacaaa accctgaa                                38

<210> SEQ ID NO 22
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 22
agacaaaacc ctgaaattma caaaaawgca gaaagcagga t                            41

<210> SEQ ID NO 23
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 23
tttgtcacca tgwcaggagg attccgcag                                          29

<210> SEQ ID NO 24
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 24
gattttaaaa ttgcmccatc agagagtaga cagt                                    34

<210> SEQ ID NO 25
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 25
tctagagccc gcctaatcag cgggcttttt tttat                                   35

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_difference
<222> LOCATION: (1)..(1)
<223> OTHER INFORMATION: 5' 6-Fluorescein

<400> SEQUENCE: 26
attcaggacg agcctcagac c                                                  21

<210> SEQ ID NO 27
<211> LENGTH: 22
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_difference
<222> LOCATION: (1)..(1)
<223> OTHER INFORMATION: 5' 6-Fluorescein

<400> SEQUENCE: 27
tttcggtggt cgccgtatcc gc                                          22

<210> SEQ ID NO 28
<211> LENGTH: 35
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_difference
<222> LOCATION: (35)..(35)
<223> OTHER INFORMATION: 3' Phosphate

<400> SEQUENCE: 28
gcggatacgg cgaccaccga gatctacact ctgag                            35

<210> SEQ ID NO 29
<211> LENGTH: 38
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_difference
<222> LOCATION: (38)..(38)
<223> OTHER INFORMATION: 3' Phosphate

<400> SEQUENCE: 29
tttctcagag tgtagatctc ggtggtcgcc gtatccgc                         38

<210> SEQ ID NO 30
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (20)..(20)
<223> OTHER INFORMATION: Fluorescein T

<400> SEQUENCE: 30
cgcttgcaca ggtgcgttct a                                           21

<210> SEQ ID NO 31
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (16)..(16)
<223> OTHER INFORMATION: Fluorescein T

<400> SEQUENCE: 31
cgcttgcaca ggtgctgttc a                                           21

<210> SEQ ID NO 32
<211> LENGTH: 21
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (11)..(11)
<223> OTHER INFORMATION: Fluorescein T

<400> SEQUENCE: 32
cgcttgcaca tggtgcgttc a                                         21

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_difference
<222> LOCATION: (17)..(18)
<223> OTHER INFORMATION: T Cy3 T

<400> SEQUENCE: 33
cgcttgcaca ggtgcgttca                                           20
```

UNITED STATES PATENT AND TRADEMARK OFFICE
CERTIFICATE OF CORRECTION

PATENT NO. : 12,110,516 B2  
APPLICATION NO. : 17/317721  
DATED : October 8, 2024  
INVENTOR(S) : Saurabh Rajendra Nirantar et al.

Page 1 of 1

It is certified that error appears in the above-identified patent and that said Letters Patent is hereby corrected as shown below:

In the Claims

Column 92, Line 28:
In Claim 9, delete "Glu191, Lys193," and insert -- Glu191, --.

Column 92, Line 42:
In Claim 13, delete "C.or" and insert -- C. or --.

Column 92, Line 48:
In Claim 14, delete "a" and insert -- the --.

Signed and Sealed this
Twenty-fifth Day of March, 2025

Coke Morgan Stewart
*Acting Director of the United States Patent and Trademark Office*